(12) United States Patent
Allen

(10) Patent No.: US 10,667,822 B2
(45) Date of Patent: *Jun. 2, 2020

(54) DEVICES AND METHODS FOR LOW PRESSURE TUMOR EMBOLIZATION

(71) Applicant: Embolx, Inc., Sunnyvale, CA (US)

(72) Inventor: Michael P. Allen, Los Altos, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,389

(22) Filed: Dec. 15, 2017

(65) Prior Publication Data

US 2018/0125502 A1 May 10, 2018

Related U.S. Application Data

(60) Continuation of application No. 15/202,391, filed on Jul. 5, 2016, now Pat. No. 9,844,383, which is a (Continued)

(51) Int. Cl.
*A61M 31/00* (2006.01)
*A61B 17/12* (2006.01)
(Continued)

(52) U.S. Cl.
CPC .... *A61B 17/12186* (2013.01); *A61B 17/1204* (2013.01); *A61B 17/12109* (2013.01); (Continued)

(58) Field of Classification Search
CPC .... A61B 17/12136; A61M 2005/1726; A61M 2025/0001; A61M 2025/0002; (Continued)

(56) References Cited

U.S. PATENT DOCUMENTS 4,581,017 A 4/1986 Sahota
4,737,153 A 4/1988 Shimamura et al.
(Continued)

FOREIGN PATENT DOCUMENTS

CN 101400400 A 4/2009
CN 102802698 A 11/2012
(Continued)

OTHER PUBLICATIONS

Angiodynamics; Soft-vu angiographic catheters; 2 pages; retrieved from the internet (http://www.angiodynamics.com/products/soft-vu) on Aug. 17, 2018.
(Continued)

*Primary Examiner* — Rebecca E Eisenberg
(74) *Attorney, Agent, or Firm* — Shay Glenn LLP

(57) ABSTRACT

A method of transarterial embolization agent delivery at a low pressure is provided. The method comprises advancing a delivery device with an occlusion structure in a retracted non-occlusive configuration through a supply artery to a vascular position in the supply artery that is in the vicinity of a target anatomical structure, the target structure having terminal capillary beds, expanding the occlusion structure from the retracted non-occlusive configuration to an expanded occlusive configuration, lowering a mean arterial pressure in a vascular space distal to the expanded occlusion structure, redirecting fluid flow from the collateral vessels toward the lowered pressure vascular space and into the target anatomical structure, injecting an embolization agent through the delivery device and into the lowered pressure vascular space, and delivering the embolization agent from the lowered pressure vascular space into the target anatomical structure. Other catheter assemblies and methods of use are also disclosed.

21 Claims, 54 Drawing Sheets

Related U.S. Application Data continuation-in-part of application No. 14/954,699, filed on Nov. 30, 2015, now Pat. No. 10,130,762, which is a division of application No. 14/273,445, filed on May 8, 2014, now Pat. No. 9,205,226.

(60) Provisional application No. 61/821,058, filed on May 8, 2013, provisional application No. 61/915,425, filed on Dec. 12, 2013, provisional application No. 61/917,131, filed on Dec. 17, 2013.

(51) Int. Cl.
*A61M 25/10* (2013.01)
*A61M 25/00* (2006.01)
*A61M 5/172* (2006.01)

(52) U.S. Cl.
CPC ... *A61B 17/12136* (2013.01); *A61M 25/0068* (2013.01); *A61M 25/0069* (2013.01); *A61M 25/10* (2013.01); *A61B 2017/1205* (2013.01); *A61M 25/1002* (2013.01); *A61M 2005/1726* (2013.01); *A61M 2025/0003* (2013.01); *A61M 2025/0076* (2013.01); *A61M 2025/1052* (2013.01); *A61M 2025/1061* (2013.01); *A61M 2025/1081* (2013.01); *A61M 2025/1093* (2013.01); *A61M 2025/1097* (2013.01); *A61M 2210/1433* (2013.01); *A61M 2210/166* (2013.01); *A61M 2230/30* (2013.01)

(58) Field of Classification Search
CPC .... A61M 2025/0076; A61M 2025/105; A61M 2025/1052; A61M 2025/109; A61M 2025/1097

See application file for complete search history.

(56) References Cited

U.S. PATENT DOCUMENTS

| | | |
|---|---|---|
| 4,748,982 A | 6/1988 | Horzewski et al. |
| 4,892,519 A | 1/1990 | Songer et al. |
| 4,896,669 A | 1/1990 | Bhate et al. |
| 4,909,252 A * | 3/1990 | Goldberger ....... A61M 25/1002 604/103.1 |
| 4,944,745 A | 7/1990 | Sogard et al. |
| 4,976,690 A | 12/1990 | Solar et al. |
| 4,990,143 A | 2/1991 | Sheridan |
| 5,000,734 A | 3/1991 | Boussignac et al. |
| 5,040,548 A | 8/1991 | Yock |
| 5,047,045 A | 9/1991 | Arney et al. |
| 5,078,685 A | 1/1992 | Colliver |
| 5,090,958 A | 2/1992 | Sahota |
| 5,137,513 A | 8/1992 | Mcinnes et al. |
| 5,156,594 A | 10/1992 | Keith et al. |
| 5,217,434 A | 6/1993 | Arney |
| 5,279,562 A | 1/1994 | Sirhan et al. |
| 5,334,154 A | 8/1994 | Samson et al. |
| 5,342,386 A | 8/1994 | Trotta |
| 5,356,388 A | 10/1994 | Sepetka et al. |
| 5,370,655 A | 12/1994 | Burns |
| 5,423,754 A | 6/1995 | Cornelius et al. |
| 5,423,829 A | 6/1995 | Pham et al. |
| 5,429,605 A | 7/1995 | Richling |
| 5,454,795 A | 10/1995 | Samson |
| 5,470,314 A | 11/1995 | Walinsky |
| 5,484,409 A | 1/1996 | Atkinson et al. |
| 5,498,251 A | 3/1996 | Dalton |
| 5,501,667 A | 3/1996 | Verduin |
| 5,509,910 A | 4/1996 | Lunn |
| 5,556,383 A | 9/1996 | Wang et al. |
| 5,582,619 A | 12/1996 | Ken |
| 5,588,442 A | 12/1996 | Scovil et al. |
| 5,599,326 A | 2/1997 | Carter |
| 5,624,449 A | 4/1997 | Pham et al. |
| 5,643,254 A | 7/1997 | Scheldrup et al. |
| 5,647,198 A | 7/1997 | Mihailovic |
| 5,649,949 A | 7/1997 | Wallace et al. |
| 5,669,905 A | 9/1997 | Scheldrup et al. |
| 5,674,198 A | 10/1997 | Leone |
| 5,690,666 A | 11/1997 | Berenstein et al. |
| 5,690,667 A | 11/1997 | Gia |
| 5,718,711 A | 2/1998 | Berenstein et al. |
| 5,722,424 A | 3/1998 | Engelson |
| 5,749,837 A | 5/1998 | Palermo et al. |
| 5,766,192 A | 6/1998 | Zacca |
| 5,769,830 A | 6/1998 | Parker |
| 5,792,300 A | 8/1998 | Inderbitzen et al. |
| 5,797,874 A | 8/1998 | Spears |
| 5,800,454 A | 9/1998 | Jacobsen et al. |
| 5,807,355 A | 9/1998 | Ramzipoor et al. |
| 5,830,182 A | 11/1998 | Wang et al. |
| 5,833,705 A | 11/1998 | Ken et al. |
| 5,843,032 A | 12/1998 | Kastenhofer |
| 5,843,050 A | 12/1998 | Jones et al. |
| 5,851,203 A | 12/1998 | Van Muiden |
| 5,853,418 A | 12/1998 | Ken et al. |
| 5,891,128 A | 4/1999 | Gia et al. |
| 5,911,717 A | 6/1999 | Jacobsen et al. |
| 5,951,539 A | 9/1999 | Nita et al. |
| 5,951,929 A | 9/1999 | Wilson |
| 5,984,878 A | 11/1999 | Engelson |
| 5,984,929 A | 11/1999 | Bashiri et al. |
| 6,013,084 A | 1/2000 | Ken et al. |
| 6,014,919 A | 1/2000 | Jacobsen et al. |
| 6,019,757 A | 2/2000 | Scheldrup |
| 6,022,340 A | 2/2000 | Sepetka et al. |
| 6,036,670 A | 3/2000 | Wijeratne et al. |
| 6,066,157 A | 5/2000 | Barbere |
| 6,071,286 A | 6/2000 | Mawad |
| 6,090,099 A | 7/2000 | Samson et al. |
| 6,123,714 A | 9/2000 | Gia et al. |
| 6,156,061 A | 12/2000 | Wallace et al. |
| 6,165,163 A | 12/2000 | Chien et al. |
| 6,187,027 B1 | 2/2001 | Mariant et al. |
| 6,190,358 B1 | 2/2001 | Fitzmaurice et al. |
| 6,203,547 B1 | 3/2001 | Nguyen et al. |
| 6,258,080 B1 | 7/2001 | Samson |
| 6,270,495 B1 | 8/2001 | Palermo |
| 6,280,457 B1 | 8/2001 | Wallace et al. |
| 6,287,301 B1 | 9/2001 | Thompson et al. |
| 6,319,228 B1 | 11/2001 | Kastenhofer |
| 6,344,041 B1 | 2/2002 | Kupiecki et al. |
| 6,397,850 B1 | 6/2002 | Scheldrup et al. |
| 6,423,085 B1 | 7/2002 | Murayama et al. |
| 6,428,489 B1 | 8/2002 | Jacobsen et al. |
| 6,440,088 B1 | 8/2002 | Jacobsen et al. |
| 6,468,266 B1 | 10/2002 | Bashiri et al. |
| 6,471,673 B1 | 10/2002 | Kastenhofer |
| 6,508,804 B2 | 1/2003 | Serge et al. |
| 6,553,880 B2 | 4/2003 | Jacobsen et al. |
| 6,575,959 B1 | 6/2003 | Sarge et al. |
| 6,579,246 B2 | 6/2003 | Jacobsen et al. |
| 6,635,069 B1 | 10/2003 | Teoh et al. |
| 6,638,245 B2 | 10/2003 | Miller et al. |
| 6,652,508 B2 | 11/2003 | Griffin et al. |
| 6,656,550 B1 | 12/2003 | Zamore |
| 6,702,782 B2 | 3/2004 | Miller et al. |
| 6,702,802 B1 | 3/2004 | Hancock et al. |
| 6,706,025 B2 | 3/2004 | Engelson et al. |
| 6,766,720 B1 | 7/2004 | Jacobsen et al. |
| 6,780,181 B2 | 8/2004 | Kroll et al. |
| 6,835,189 B2 | 12/2004 | Musbach et al. |
| 6,860,893 B2 | 3/2005 | Wallace et al. |
| 6,860,899 B1 | 3/2005 | Rivelli |
| 6,878,151 B2 | 4/2005 | Carrison et al. |
| 6,921,410 B2 | 7/2005 | Porter |
| 6,936,055 B1 | 8/2005 | Ken et al. |
| 6,997,937 B2 | 2/2006 | Jacobsen et al. |
| 7,004,962 B2 | 2/2006 | Stinson |
| 7,037,330 B1 | 5/2006 | Rivelli et al. |
| 7,060,083 B2 | 6/2006 | Gerberding |
| 7,070,607 B2 | 7/2006 | Murayama et al. |
| 7,144,407 B1 | 12/2006 | Lasersohn |

(56) References Cited

U.S. PATENT DOCUMENTS

| | | |
|---|---|---|
| 7,153,323 B1 | 12/2006 | Teoh et al. |
| 7,166,122 B2 | 1/2007 | Aganon et al. |
| 7,294,137 B2 | 11/2007 | Rivelli et al. |
| 7,332,689 B2 | 2/2008 | Mertens et al. |
| 7,412,285 B2 | 8/2008 | Schroeppel et al. |
| 7,468,070 B2 | 12/2008 | Henry et al. |
| 7,481,800 B2 | 1/2009 | Jacques |
| 7,621,904 B2 | 11/2009 | McFerran et al. |
| 7,645,259 B2 | 1/2010 | Goldman |
| 7,654,979 B2 | 2/2010 | Simpson |
| 7,742,811 B2 | 6/2010 | Schroeppel et al. |
| 7,780,626 B2 | 8/2010 | Wu et al. |
| 7,942,847 B2 | 5/2011 | Stupecky et al. |
| 7,998,165 B2 | 8/2011 | Huffmaster |
| 8,066,667 B2 * | 11/2011 | Hayman .......... A61B 17/00491 604/103.01 |
| 8,092,508 B2 | 1/2012 | Leynov et al. |
| 8,202,292 B2 | 6/2012 | Kellett |
| 8,206,373 B2 | 6/2012 | Zhou |
| 8,348,890 B2 | 1/2013 | Gerrans et al. |
| 8,961,550 B2 | 2/2015 | Lenker et al. |
| 9,174,020 B2 | 11/2015 | Allen et al. |
| 9,205,226 B2 | 12/2015 | Allen et al. |
| 9,427,550 B2 | 8/2016 | Dakin et al. |
| 9,550,046 B1 | 1/2017 | Allen |
| 9,555,165 B2 | 1/2017 | Phan |
| 9,844,383 B2 | 12/2017 | Allen |
| 2001/0041862 A1 | 11/2001 | Glickman |
| 2002/0032457 A1 | 3/2002 | Sirhan et al. |
| 2003/0050600 A1 | 3/2003 | Ressemann et al. |
| 2003/0114878 A1 | 6/2003 | Diederich et al. |
| 2003/0199914 A1 | 10/2003 | Diaz |
| 2005/0131453 A1 * | 6/2005 | Parodi ................... A61B 17/12 606/200 |
| 2005/0267407 A1 | 12/2005 | Goldman |
| 2006/0106413 A1 | 5/2006 | Bence et al. |
| 2006/0276886 A1 | 12/2006 | George et al. |
| 2007/0088380 A1 | 4/2007 | Hirszowicz et al. |
| 2007/0137651 A1 | 6/2007 | Glassenberg et al. |
| 2008/0045908 A1 | 2/2008 | Gould et al. |
| 2008/0208118 A1 | 8/2008 | Goldman |
| 2008/0262470 A1 | 10/2008 | Lee et al. |
| 2009/0156999 A1 | 6/2009 | Adams et al. |
| 2009/0177183 A1 | 7/2009 | Pinkernell et al. |
| 2010/0030200 A1 | 2/2010 | Strauss et al. |
| 2010/0113939 A1 | 5/2010 | Mashimo et al. |
| 2010/0249491 A1 | 9/2010 | Farnan et al. |
| 2012/0203173 A1 | 8/2012 | Davies et al. |
| 2012/0253447 A1 | 10/2012 | Hayasaka et al. |
| 2013/0131610 A1 | 5/2013 | Dewaele et al. |
| 2014/0163421 A1 | 6/2014 | Van Hoven |
| 2014/0371709 A1 | 12/2014 | Allen et al. |
| 2014/0371718 A1 | 12/2014 | Alvarez et al. |
| 2015/0351729 A1 | 12/2015 | Chin et al. |
| 2016/0008585 A1 | 1/2016 | Tano |
| 2016/0096002 A1 | 4/2016 | Di Caprio et al. |
| 2016/0158439 A1 | 6/2016 | Allen |
| 2016/0213893 A1 | 7/2016 | Franklin |
| 2017/0049495 A1 | 2/2017 | Yu et al. |
| 2017/0095646 A1 | 4/2017 | Norman et al. |
| 2019/0083705 A1 | 3/2019 | Allen |

FOREIGN PATENT DOCUMENTS

| | | |
|---|---|---|
| CN | 102805893 A | 12/2012 |
| EP | 1131126 B1 | 8/2004 |
| EP | 2389968 A2 | 11/2011 |
| JP | 2003500121 A | 1/2003 |
| WO | WO89/08471 A1 | 9/1989 |
| WO | WO2004/107965 A2 | 12/2004 |
| WO | WO2012/009486 A2 | 1/2012 |
| WO | WO2012/099979 A1 | 7/2012 |
| WO | WO2014/008489 A1 | 1/2014 |

OTHER PUBLICATIONS

BMI ESPICOM Pharmaceutical and Medical Device News; Business Monitor Online: Vascular solutions expands complex intervention offerings with turnpike LP catheter; newsletter; 2pages; retrieved from the internet (https://dialog.proquest.com/professional/docview/1753127273?accountid=157282) on Apr. 18, 2018 (Abstract Only).

Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.

Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.

Vante Plasticweld Systems; Bonds and welds; 13 pages; retrieved from the internet (https://cathetertipping.com/home/our-products/bonding/) on Aug. 17, 2018.

Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).

Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.

Halstead et al.; U.S. Appl. No. 16/004,247 entitled "High torque catheter and methods of manufacture," filed Jun. 8, 2018.

Halstead et al.; U.S. Appl. No. 16/047,922 entitled "Shaped catheter tip for tracking over a guidewire through turns in the vasculature," filed Jul. 27, 2018.

Cook Medical; Flexor technology; 16 pages; retrieved from the Internet (https:cookmedical.com/data/resources/PI-BM-KCF-EN-201302_WEB.pdf) on May 5, 2019.

Cliffton et al.; Technique for visualization and perfusion of bronchial arteries: suggested clinical and diagnostic applications; Cancer; 16; pp. 444-452; Apr. 1963.

Rousselot et al.; Selective concentration of anticancer drugs in the liver: Hepatic-artery infusion and induced hepatic outflow block; JAMA; 191(9); pp. 707-710; Mar. 1965.

Allen et al.; U.S. Appl. No. 15/413,262 entitled "Balloon catheter and methods of fabrication and use," filed Jan. 23, 2017.

\* cited by examiner

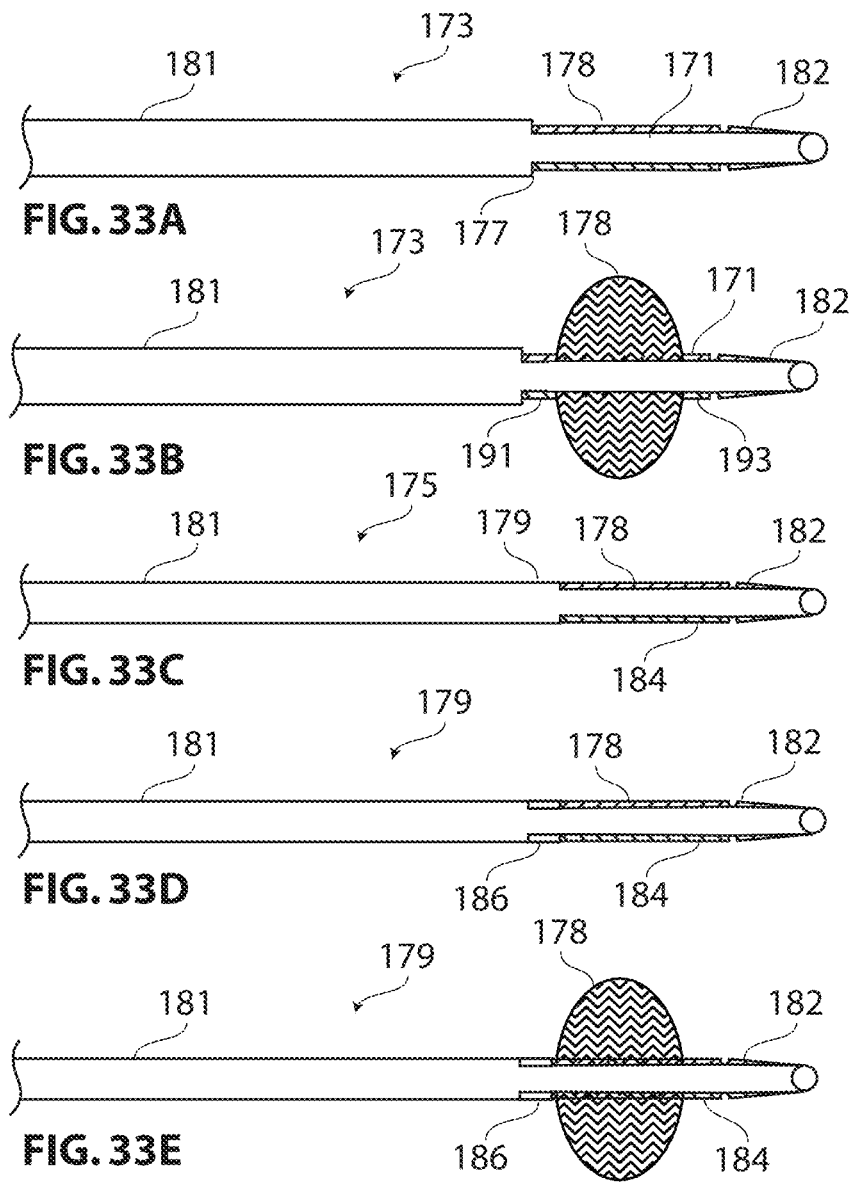

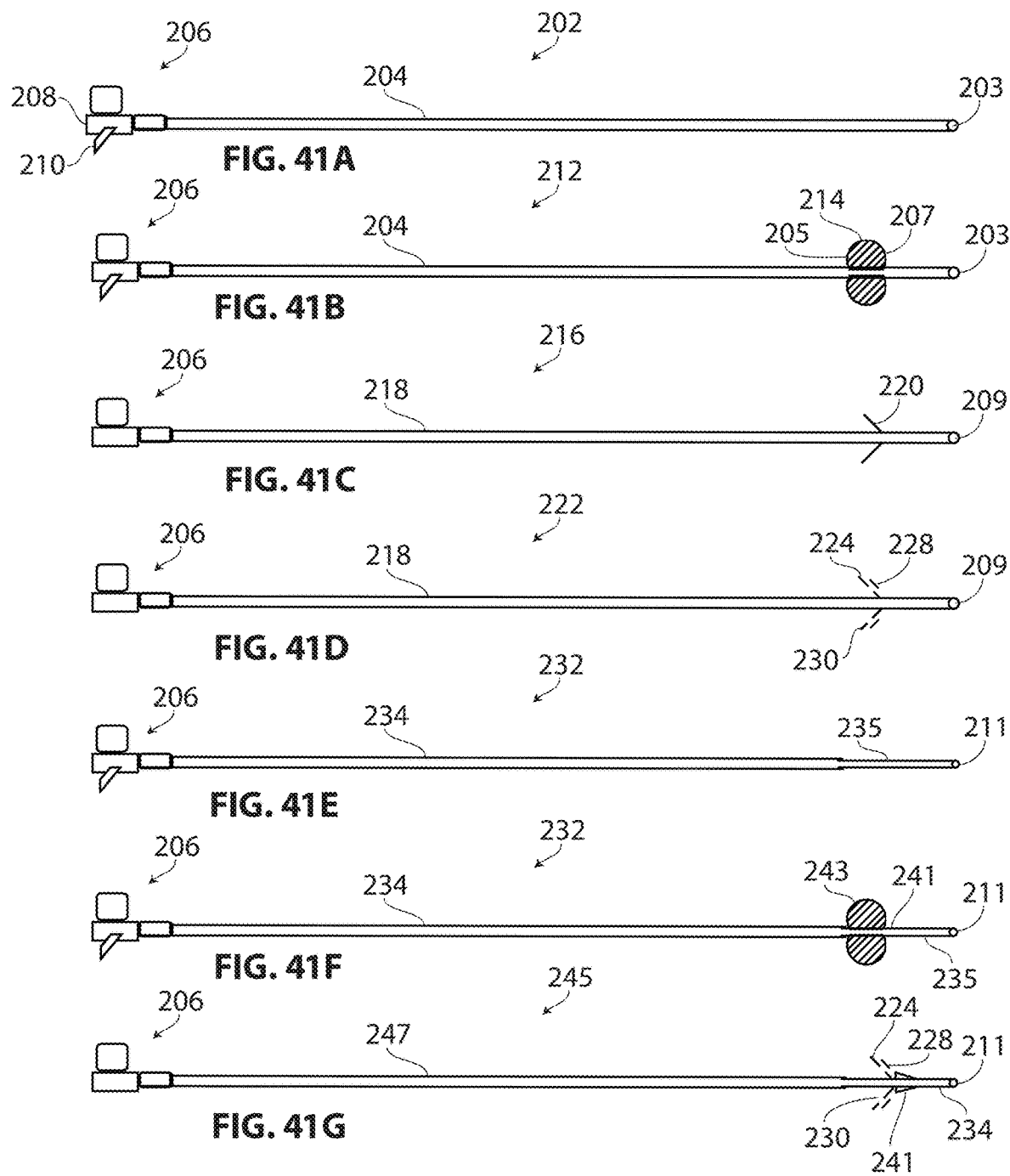

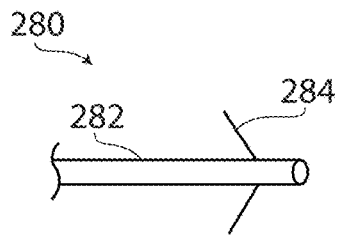
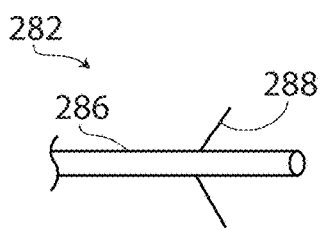
FIG. 45A     FIG. 45B
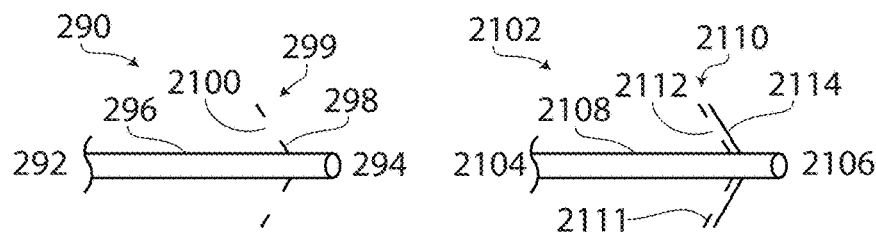
FIG. 46A     FIG. 46B
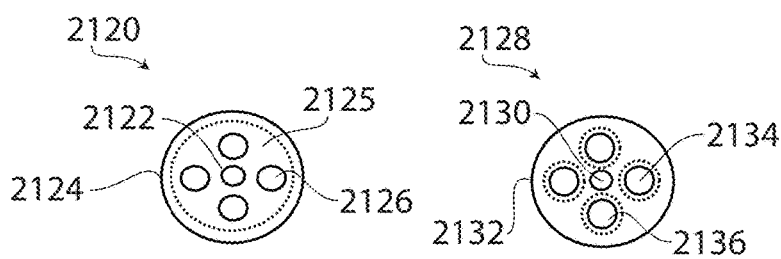
FIG. 47A     FIG. 47B
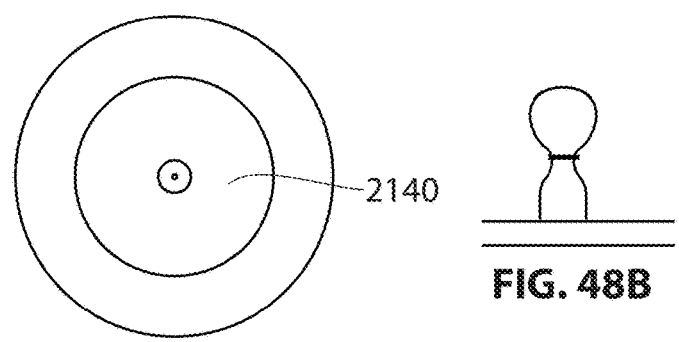
FIG. 48A     FIG. 48B

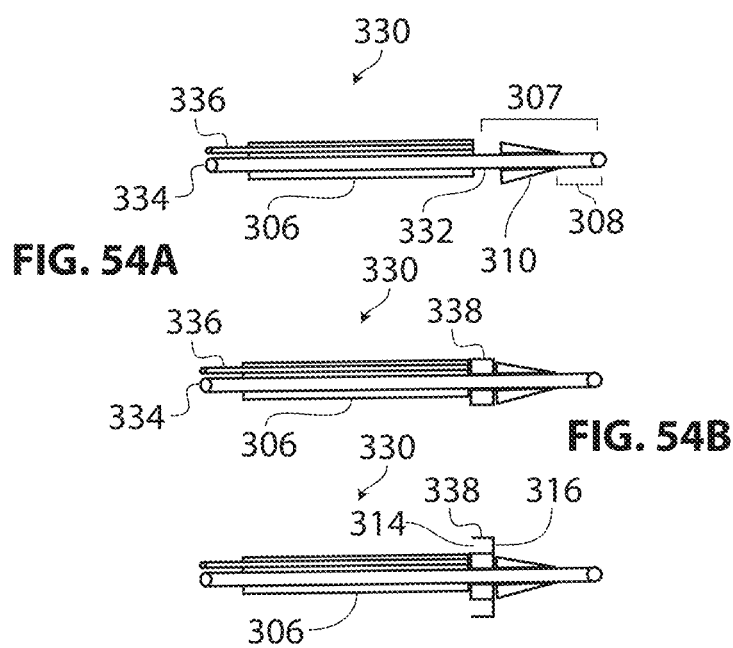
FIG. 54A
FIG. 54B
FIG. 54C
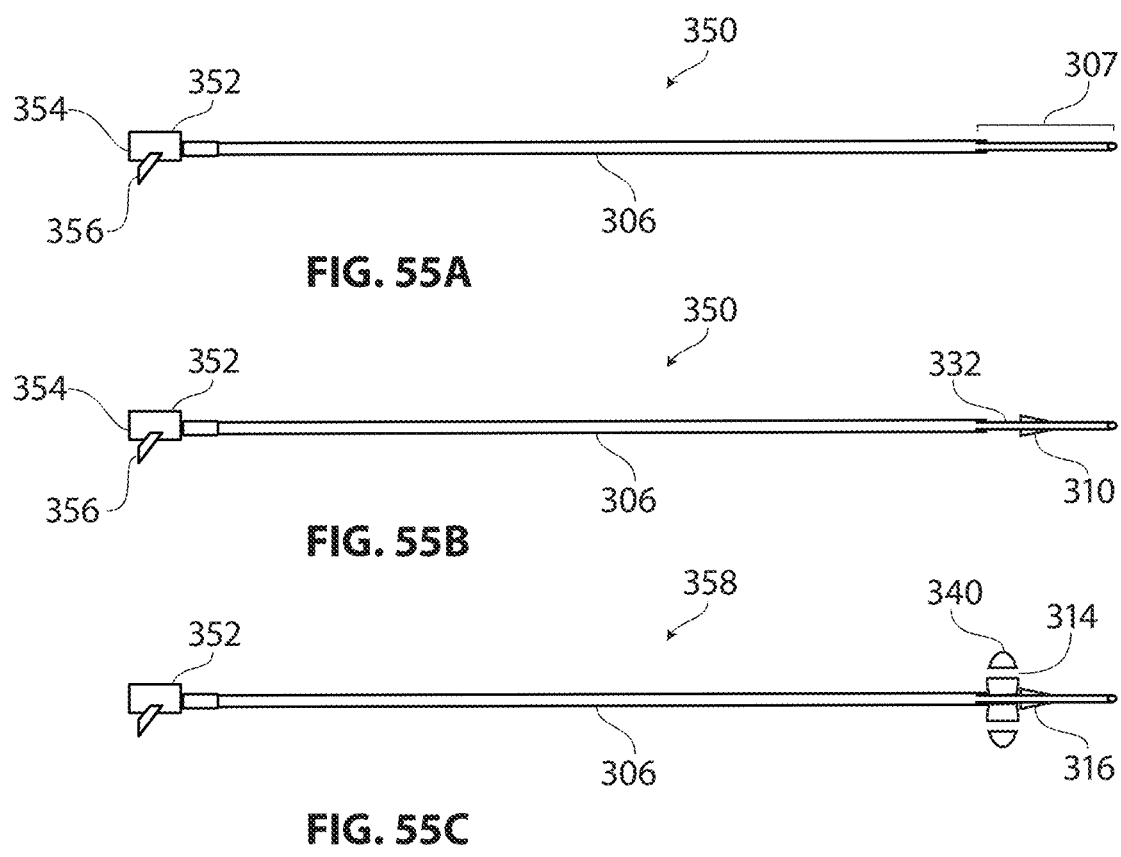
FIG. 55A
FIG. 55B
FIG. 55C

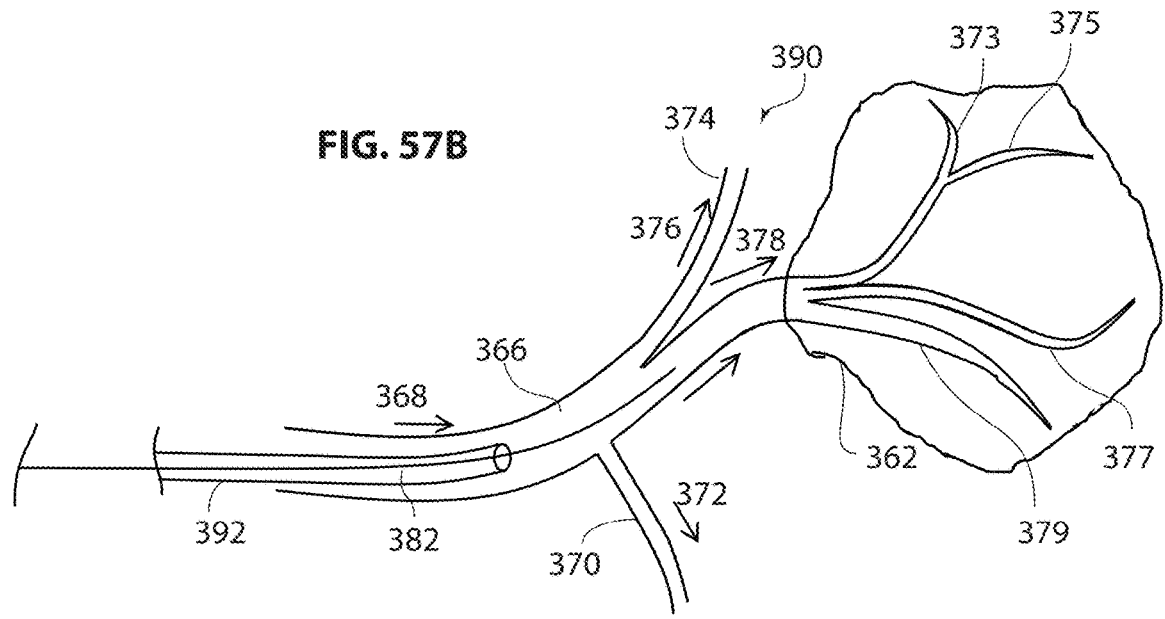
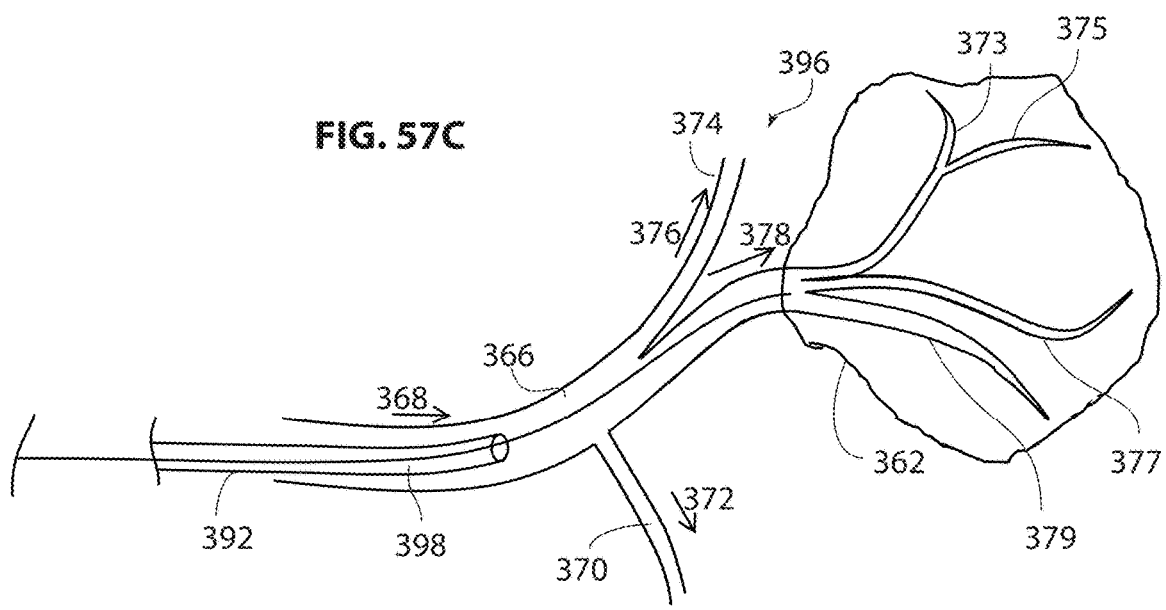

A

B

C

D

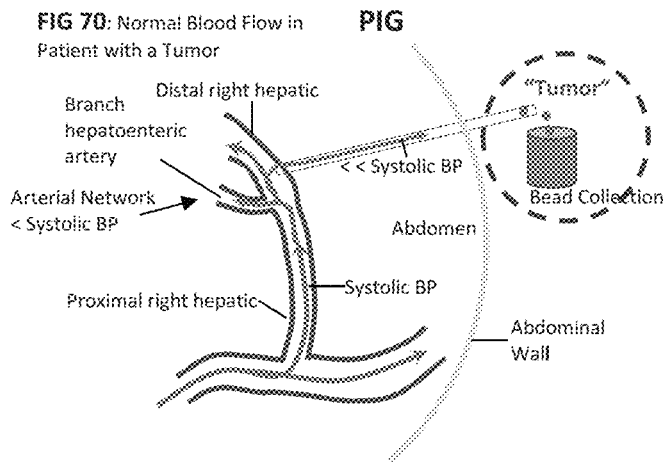
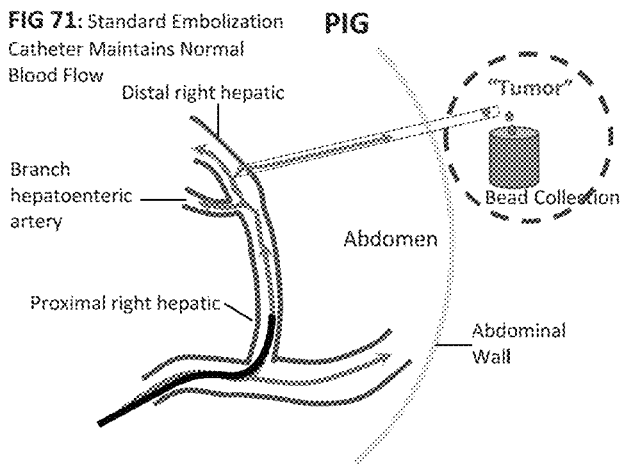
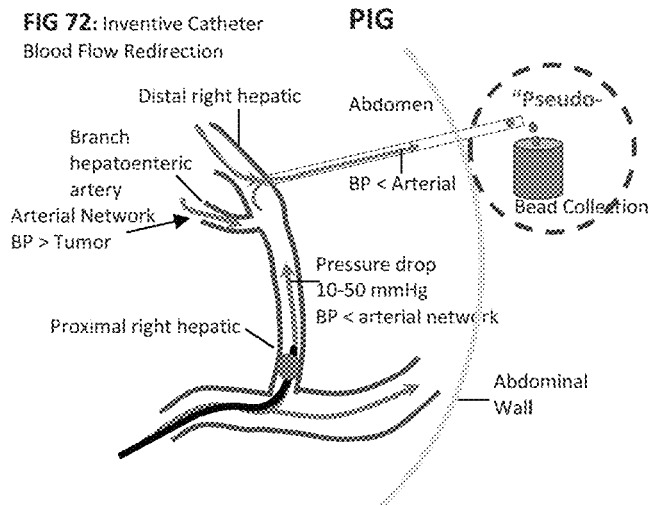

FIG. 73

| | | Bead Collection | | | |
|---|---|---|---|---|---|
| Date | Placement Position | Bead Size (μm) | Balloon Inflated | Balloon Deflated | Multiplier Improvement |
| October 14, 2015 | | | | | |
| Pig 1 | 1 | | | | |
| | 2 | No data, Pig vascular anatomy abnormal | | | |
| Pig 2 | 1 | 250 | 70667 | 17917 | 3.94 |
| | 1 | 400 | 12367 | 8333 | 1.48 |
| | 2 | 400 | 14367 | 9000 | 1.60 |
| Pig 3 | 1 | 250 | 54000 | 21583 | 2.50 |
| | 2 | 250 | 16000 | 9417 | 1.70 |
| | 2 | 400 | 11800 | 4533 | 2.60 |
| October 21, 2015 | | | | | |
| Pig 1 | 2 | 250 | 43833 | 23417 | 1.87 |
| Pig 2 | 1 | 250 | 17333 | 10833 | 1.60 |
| | 2 | 250 | 46083 | 12167 | 3.79 |
| | 2 | 400 | 14533 | 10100 | 1.44 |
| Pig 3 | 1 | 250 | 15750 | 11667 | 1.35 |
| | 1 | 400 | 13167 | 2900 | 4.54 |

DEVICES AND METHODS FOR LOW PRESSURE TUMOR EMBOLIZATION

CROSS REFERENCE TO RELATED APPLICATIONS

This application is a continuation of U.S. application Ser. No. 15/202,391, filed Jul. 5, 2016, which is a continuation-in-part of U.S. application Ser. No. 14/954,699, filed Nov. 30, 2015, which is a divisional of U.S. application Ser. No. 14/273,445, filed May 8, 2014, now U.S. Pat. No. 9,205,226, which claims the benefit of U.S. Provisional Application No. 61/821,058, filed May 8, 2013, U.S. Provisional Application No. 61/915,425, filed Dec. 12, 2013, and U.S. Provisional Application No. 61/917,131, filed Dec. 17, 2013, each of which is herein incorporated by reference in its entirety.

GOVERNMENT RIGHTS

This invention was made with Government support under Grant No. 1417279 awarded by the National Science Foundation. The Government has certain rights in this invention.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to medical methods and devices. More specifically, the present application discloses various embodiments of occlusion devices adapted to a catheter, and methods for their use in delivering fluids, embolic materials and other therapeutic agents to sites within the body.

BACKGROUND

There are over one million cases of cancer diagnosed each year in the United States and numerous approaches of therapy including systemic chemotherapy, radiation and surgical resection. Given that systemic chemotherapy and radiation interact with healthy tissue, complications and toxicity often result. Targeted drugs are now being used and produce a lower rate of complications. Ablative approaches, including microwave, radiofrequency and cryogenic therapies have been used; however, these methods are often not selective and tissues and organs surrounding or below the tumor can be affected.

According to the National Institute of Health, 30,640 people were diagnosed with primary liver cancer (hepatocellular carcinoma, HCC) and 142,820 people were diagnosed with colorectal cancer in the U.S. in 2013. Seventy-five percent of these will metastasize to the liver. Liver resection and transplant are the only curative means; however, only small numbers of patients are eligible. Systemic chemotherapy for primary and metastatic tumors in the liver is ineffective, having a response rate of about 20% and a survival benefit of 10.7 months vs. 7.9 months over symptomatic care.

Catheters are commonly used in medicine for delivery of fluids, therapeutics, and implants, and in sampling tissues and bodily fluids. Catheters can be constructed with balloons or other tools to dilate tissue, block fluid flow or isolate segments of the anatomy, such as in treatment of the cancers described above.

Transvascular fluid delivery via arteries or veins is typically used to distribute materials throughout the body and without consideration of a specific target tissue or organ. One notable exception to this is the use of compounds, such as anti-cancer agents that are conjugated to antibodies that target a specific binding site. Anti-tumor agents can also be fashioned to bind to specific cell receptors and block cellular functions of cancer cells. In this way, cytotoxic therapies seek out cancer cells and avoid healthy tissues, reducing systemic toxicity.

However, most drugs are not conjugated or otherwise contrived to seek out a target and drugs that are injected are distributed throughout the body, even though the beneficial effect is limited to one or several target sites. Delivery of drug to non-target sites can cause complications and result in considerable morbidity.

Trans-Arterial Embolization therapy is the transvascular injection of drug and/or embolic agents directly into the tumor vasculature using a microcatheter. Embolization therapy causes a shutdown of blood flow and, when drug or radioactivity is present, simultaneous release of high concentrations of drug or radioactivity. The technique is also noted for its very low level of toxicity.

In the early 1980's, transarterial chemoembolization (TACE) began to be used as a selective cancer therapy. In this method, chemotherapeutic and embolic agents are injected directly into the vasculature of the tumor, a technique that is most common for the treatment of hepatocellular carcinoma. More recently, transarterial radioembolization (TARE) has been used clinically. In this method, radioactive embolic particles, typically yttrium-90 (y90), are injected rather than chemotherapeutic agents. Although the liver is a common target for TACE and TARE, other organs, including, but not limited to, the pancreas, lung, kidney, prostate, stomach, colon and head and neck have been treated using these methods. Chemoembolization was established as a standard of care for intermediate stage hepatocellular carcinoma in 2006.

Numerous studies have demonstrated transarterial embolization to be effective on a number of primary cancers and to have better performance than chemotherapy for both HCC and metastatic colorectal cancers in the liver; however, studies show inconsistent outcomes with reported tumor responses from 15% to 85%. Although anatomical and individual differences are clearly of significance in between-patient variation, clinical studies, each of which include numerous patients, show very different outcomes, indicating that the procedure is not reproducible and that there is little procedural optimization or standardization.

The above procedures are accomplished by inserting a small catheter into the femoral artery at the groin or radial artery of the forearm and navigating it into the liver vasculature, typically the hepatic artery, then into the right or left lobe of the liver or more selectively into particular segments of the liver or super-selectively directly into or adjacent to the tumor. Typically, the tip of the microcatheter is positioned in a supply artery that is proximal to the tumor feeder artery and collateral arteries that branch from the supply artery and flow toward healthy tissues. In this instance, blood flows over the catheter tip and into the tumor and collateral arteries that feed healthy tissues. Injection of embolic agents will follow blood flow and deposit into both the tumor and healthy tissues (non-target embolization). Presently, standard microcatheters, typically at or about 3 Fr, are used to inject antitumor agents into the target vasculature. These standard microcatheters rely on normal blood flow as the means by which the embolic agent moves into the tumor and systolic and/or mean arterial pressure as the packing force. However, as the tumor begins to become embolized, it cannot accept the normal rate of blood flow and intra-tumor pressure rises to a point where the tumor can no longer accept the blood flow and the blood begins to reflux into the tumor feeder and supply artery. At this point tumor embolization can no longer proceed since embolization agents are refluxing out of the tumor along with the blood, even though the tumor is only partially filled with embolic agents. Under these conditions, further injection of embolic agents results in high pressures in the supply artery and a concomitant increase in non-target flow of embolic agents to healthy tissues and reflux backwards over the catheter. This situation also results in loss of an unknown amount of drug which, at least in part, explains the irreproducibility of the technique.

The endpoint of the above procedures is determined by physicians' visual observation of contrast flow and therefore the amount of dose delivered is highly variable. Reflux, non-target embolization in antegrade and retrograde directions, distribution of embolic agents, packing and quantity of dose delivered are variables that can be highly dependent on the rate and pressure of injection, the selection of the type of endpoint, the patient's systolic and/or mean arterial pressure, anatomy and the operator. As such, clinical trials using TACE to treat hepatocellular carcinoma have demonstrated wide variations in tumor response. The most significant clinical problems that occur with the current means of delivery and methods of embolization therapy include inconsistent efficacy and complications from non-target embolization.

Using standard straight-tip catheters, non-target embolization in the retrograde and antegrade directions can be caused when the pressure of injection exceeds the mean arterial blood pressure whereby embolic agents flow into healthy tissues causing complications.

Antegrade

When therapeutic agents are delivered into the vasculature of a target structure using the normal antegrade blood flow to carry the therapy to the target, antegrade non-target flow is unavoidable and injection rate of therapeutic agents must be carefully controlled in relation to the then present flow volume and pressure of blood to avoid an increased amount of antegrade non-target flow and reflux of drug backward over the catheter and into healthy tissues. In particular, when injecting embolic agents into the vasculature of a tumor, pressure distal to the catheter tip continues to increase as embolization progresses, causing a resistance that prevents embolic agents from filling the target vasculature and the possibility of reflux and non-target flow and embolization. It would be desirable to eliminate this antegrade non-target flow and reflux, and the inconsistent dosages that are delivered to targets with current state of the art procedures. It would be further desirable to eliminate the low levels of particle distribution and density throughout the target vasculature. It would be still further desirable to replace current delivery devices that are not always capable of fully isolating the target vasculature and often do not allow the operator to control pressure, flow rate and other parameters associated with therapeutic delivery.

The present state-of-the-art embolization therapy using standard straight-tip microcathetes for tumors in the liver relies on high volume forward flow from the hepatic artery (supply artery) to deliver embolization agents into the tumor. However, as tumor embolization proceeds, larger arterioles and capillaries are filled first, this substantially stopping flow in these vessels which causes: (1) high intra-tumor vascular pressure, (2) high pressure in arteries feeding the tumor, (3) high pressure in the supply artery, (4) reflux over the delivery catheter, (4) increased antegrade non-target flow into hepatoenteric arteries and (5) poor filling and distribution of embolic agents in the tumor. This situation results in an uncontrollable and irreproducible number of particles entering the tumor and high procedural variability.

Problems with the current method of embolization therapy that cause inconsistent outcomes include: high flow rates into the tumor, variable procedural endpoints, unknown quantity of dose delivered, reflux of embolization agents, antegrade non-target flow of embolization particles into branch arteries, rising intra-tumor arterial pressures during the initial stages of embolization, catheter movement during injection, catheter tip position and the catheter not being centered in the blood vessel. The current delivery catheters are unable to control many of the above mentioned variables, producing inconsistent outcomes and making any standardization of the current procedures difficult or impossible to achieve.

The following patents and published patent applications provide some examples of the current state of this art. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) Cancer 16:444-452 describes a two balloon catheter for the treatment of lung carcinoma. The four lumen catheter includes a lumen for independent injection in the space between the balloons. Rousselot et al. (1965) JAMA 191: 707-710 describes a balloon catheter device for delivering anticancer drugs into the Liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

What is needed, and not provided by the prior art, are delivery devices and methods that enable exclusive delivery of drug to a target area of the anatomy and elimination or reduction of the flow of drug outside of the target area.

SUMMARY OF THE DISCLOSURE

According to aspects of the present disclosure, devices and methods are provided for full or partial occlusion that are designed to be adapted to a catheter for delivery of therapeutic agents to a target site within the body. Such delivery devices may be intended for any medical purpose, but the embodiments described herein are focused on devices intended for performing transarterial delivery of therapeutic agents to a target site within the body. The entry point for the delivery catheter can be any arterial access point, typically the femoral artery located at the groin or the radial artery in the forearm. The target can be any structure;

however, of particular interest are tumors, primary or metastatic, of any organ or tissue that is accessible by a microcatheter through the arterial system. Cancers of particular interest include, but are not limited to, primary and metastatic cancers in the liver, pancreas, colon, rectum, kidney, stomach, lung, bladder, head and neck, prostate and uterus. Procedures that can benefit from the access and delivery methods and devices of the present disclosure include, but are not limited to, transarterial chemoembolization using drug eluting beads (DEB TACE), transarterial chemoembolization using Lipiodol (Lipiodol TACE), transarterial radioembolization (TARE) and transarterial embolization (TAE). Other procedures which can benefit from methods and devices of the present disclosure include direct delivery of chemotherapy or targeted drugs to the site of the cancer, the general delivery of drugs, venous or arterial embolization or other substances to specific regions of the body and drainage or aspiration of fluid or tissue. Of particular interest are embolization of the prostate, as a therapy for benign prostatic hyperplasia (BPH), and embolization of the uterus, as a therapy for uterine fibroids.

The occlusion device of the present disclosure causes an immediate pressure drop in the vascular area distal to the occlusion, creating a low pressure zone in the distal artery and surrounding tissue. Since fluid will flow from high pressure to low pressure, blood flow will redistribute in favor of the low pressure zone. When a tumor or other structure with terminal capillary beds is within, or in the vicinity of, the low pressure zone, the blood will flow toward the terminal capillaries since they empty in to veins that have very low pressure. In this instance, the anatomical structure with terminal capillaries acts as a sump that accepts blood flow from surrounding area. By way of example, embolization of tumors in the right lobe of the liver are accessed by a catheter advanced through the right hepatic artery (RHA) and to the vicinity of the tumor. Typically, the catheter tip does not enter the tumor vasculature and remains proximal to the tumor and within the right hepatic artery or branch thereof. In this example, the artery feeding the tumor is typically a branch of the RHA. However, there other distal hepatoenteric arteries that branch from the RHA and flow away from the RHA and to the liver and gastrointestinal tract. In this instance, when using a standard straight catheter, injection of embolic agents from the distal tip of the catheter results in flow of embolic agents into both the tumor and collateral arteries causing antegrade non-target embolization of the liver and gastrointestinal tract, a situation that causes toxicity and complications. The device and method of the present disclosure causes a flow redistribution whereby collateral arteries reverse flow in favor of the tumor, minimizing non-target flow and increasing the number of embolic particles that enter the tumor.

In some embodiments, the methods and devices disclosed herein include a balloon or other structure that can be expanded or activated to create a full occlusion of the target blood vessel with a concomitant reduction in pressure and flow rate in the anatomical zone distal to the full occlusion that can: (1) eliminate reflux, (2) reduce or eliminate antegrade non-target flow, (3) reduce or eliminate non-target embolization, (4) reduce flow rate and volume moving into the tumor, (5) slow the increase of intra-tumor pressure, (6) slow the onset of blood reflux from the tumor, (7) increase the time that embolic agents can enter the tumor, (8) increase the amount and distribution of embolic agents that are deposited in the tumor, (9) isolate the vascular area distal to the occlusion from the general circulation, (10) create a low pressure zone in the vicinity of the tumor and (11) cause a general inflow of blood toward the low pressure area created by the occlusion.

In other embodiments, the microcatheter methods and devices disclosed herein, include a balloon or other structure that can be expanded or activated to create a partial occlusion of the target blood vessel such as by creating channels from the proximal end of the occlusion structure to the distal end of the occlusion structure. When in the expanded configuration there is a concomitant reduction in pressure and flow rate in the anatomical zone distal to the occlusion. The device of this embodiment can: (1) provide a distal directed bypass (forward flow) of blood, (2) eliminate reflux, (2) reduce or eliminate antegrade non-target flow, (4) reduce or eliminate non-target embolization, (5) reduce flow rate and volume moving into the tumor, (6) slow the increase of intra-tumor pressure, (7) slow the onset of blood reflux from the tumor, (8) increase the time that embolic agents can enter the tumor, (9) increase the amount and distribution of embolic agents that are deposited in the tumor, (10) isolate the vascular area distal to the occlusion from the general circulation, (11) create a low pressure zone in the vicinity of the tumor and (12) cause a general inflow of blood toward the low pressure area created by the occlusion.

In some embodiments, a catheter assembly may be provided with a catheter body and an inflatable balloon. The catheter body has a proximal end, a distal end and a balloon inflation lumen. The inflatable balloon is attachable to the distal end of the catheter body. The balloon has an inner surface that at least partially defines an interior volume. The balloon is configured such that the interior volume can be in fluid communication with the inflation lumen of the catheter body to inflate the balloon. The balloon also has a proximal surface and a distal surface. The balloon is provided with a channel that extends through the balloon as in partial occlusion or the balloon is without channels as in full occlusion. If present, the channel may be configured to provide fluid communication between the proximal surface of the balloon and the distal surface of the balloon.

In some embodiments, a device for delivering a therapeutic agent to a target site within a body is provided. The device comprises a catheter body having a proximal end, a distal end, a first axial lumen and a second axial lumen. The first axial lumen extends from the proximal end of the catheter body to the distal end of the catheter body and provides fluid communication therebetween. The second axial lumen extends from the proximal end of the catheter body to a more distal location on the catheter body. The device further comprises a balloon radially disposed near the distal end of the catheter body. The balloon has a proximal balloon surface, a distal balloon surface, a radially constrained configuration and a radially expanded configuration. The balloon is in fluid communication with the second axial lumen and is a full occlusion balloon or has at least one channel, said channel extending from the proximal balloon surface to the distal balloon surface, thereby providing fluid communication therebetween.

In some embodiments, a method of embolization of a tumor is provided. The method comprises advancing a device including a catheter body and a partial occlusion structure to a supply artery in the vicinity of a target tumor site within the body, and allowing an antegrade blood flow past the partial occlusion structure. The allowed antegrade blood flow is less than a blood flow that would normally be present if the partial occlusion structure were not in place. The partial occlusion produces a pressure drop in the anatomic zone distal to the occlusion, flow redistribution of collateral arteries and capillaries associated with the supply artery and flow being directed into and through the tumor into the venous system. The method further comprises injecting an embolic substance from the device to allow the antegrade blood flow to carry the embolic substance into a vasculature of the tumor and withdrawing the device from the body.

By isolating the distal arterial space that is adjacent to the tumor from the arterial blood supply, the device of the present disclosure enables pressure measurement to be used to signal a procedural endpoint at a predetermined pressure or pressures. By way of example, the endpoint of the procedure can occur at a point when systolic pressure (120 mmHg) is first reached or at a point when systolic pressure and/or mean arterial pressure is stabilized, however any pressure, pressure profile or algorithm can be used to determine an endpoint of the procedure. Such a measurable endpoint can contribute to standardization of the procedure and improved efficacy.

The occlusion structure of the device of the present disclosure may be held within a pocket within the catheter such that the outer diameter of the radially constrained occlusion structure is approximately equal to or less than the outer diameter of the catheter as described in co-pending U.S. patent application 15/044,864 and issued U.S. Pat. No. 9,205,226. The pocket can be a longitudinal space in the catheter and can be formed as a reduction in the catheter diameter of a defined length and a depth equal to or greater than the thickness of the occlusion structure in a radially constrained configuration. Alternately, a pocket can be formed using an extension projecting distally beyond the catheter body, the distal extension having a diameter smaller than the catheter body. In this instance, the distal end of the catheter pocket is defined by the proximal end of a nose-piece. In some embodiments, the nose-piece has a diameter equal to or less than the diameter of the catheter body and is positioned over the distal extension at a defined distance from the distal end of the catheter body.

The occlusion structure of devices of the present disclosure can be advanced in a radially constrained configuration, to at least the proximity of a target within the body and then placed in its radially expanded configuration. Alternately, the device can be pre-formed in a fully expanded configuration, adapted to the distal end of a catheter and delivered to the target site. antegrade According to aspects of the present disclosure, methods of transarterial embolization agent delivery at a low pressure are provided. In some embodiments, the method comprises advancing a delivery device with an occlusion structure in a retracted non-occlusive configuration, through a supply artery having a plurality of collateral vessels that branch therefrom and being in fluid communication with a target anatomical structure, to a vascular position in the supply artery that is in the vicinity of the target anatomical structure. The target structure has terminal capillary beds. The method further comprises expanding the occlusion structure from the retracted non-occlusive configuration to an expanded occlusive configuration, lowering a mean arterial pressure in a vascular space distal to the expanded occlusion structure, and redirecting fluid flow from the collateral vessels toward the lowered pressure vascular space and into the target anatomical structure. The method further comprises injecting an embolization agent through the delivery device and into the lowered pressure vascular space, and delivering the embolization agent from the lowered pressure vascular space into the target anatomical structure.

In some embodiments, the mean arterial pressure in the lowered pressure vascular space is lowered during the lowering step to between 10% and 60% of a normal mean arterial pressure. The lowering step may comprise measuring a pressure in the vascular space after expanding the occlusion structure. The lowering step may further comprise ensuring the measured pressure is within a predetermined range before proceeding with the injecting step. In some embodiments, the lowering step comprises waiting a predetermined period of time before proceeding with the injecting step to ensure that a sufficient pressure drop has occurred.

In some embodiments, the mean arterial pressure of the lowered pressure vascular space is kept below an un-occluded starting pressure by at least 10% of the difference between the un-occluded starting pressure and a stabilized occluded pressure during the injecting step. In some embodiments, the mean arterial pressure of the lowered pressure vascular space is kept below an un-occluded starting pressure by at least 30% of the difference between the un-occluded starting pressure and a stabilized occluded pressure during the injecting step.

In some embodiments the fluid is predominantly blood or interstitial fluid. The embolization agent may be injected with a flow rate in the range of 0.25 to 6 ml/minute. The delivery device may comprise a catheter, a needle, or a cannula. In some embodiments, the occlusion structure allows a fluid flow of 5 to 25% of normal to bypass the occlusion structure after it has been expanded into the occlusive configuration. In some embodiments, the occlusion structure creates a substantially full occlusion having less than 2% bypass blood flow.

In some embodiments, the occlusion structure comprises a balloon. The balloon may be provided with a generally v-shaped channel extending along a least a portion of its length, thereby providing a fluid bypass channel when the balloon is inflated. The balloon may be provided with a spiral channel extending from a proximal end of the balloon to a distal end, thereby providing a fluid bypass channel when the balloon is inflated. In some embodiments, the delivery device is provided with a pressure transducer located distal to the occlusion structure and configured to sense fluid pressure when located in the supply artery.

In some embodiments, the target anatomical structure is a tumor, a prostate, or a uterus.

While aspects of the present disclosure will be described with particular reference to delivery of chemotherapeutic agents, radiotherapeutic agents, embolic agents or combinations thereof into the vasculature that supplies blood to a tumor, the same principles apply to the delivery or aspiration of a variety of materials into or from other locations, and through other luminal structures in the body.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 33A, 33B, 33C, 33D and 33E illustrate a cross sectional view of a sequential construction of an embodiment of the present disclosure including a balloon pocket and separate nose cone;

FIGS. 41A, 41B, 41C, 41D, 41E, 41F and 41G illustrate constructions of embodiments of the present disclosure;

FIGS. 45A and 45B illustrate embodiments of the present disclosure for complete occlusion;

FIGS. 46A and 46B illustrate an embodiment with bidirectional and unidirectional channels;

FIGS. 47A and 47B illustrate valve constructions of an embodiment of a unidirectional occlusion structure of the present disclosure;

FIGS. 48A and 48B show a prototype micro-valve;

FIGS. 54A, 54B and 54C illustrate a distal end construction including pocket, constrained balloon and expanded partial occlusion balloon with channels and valves in closed position;

FIGS. 55A, 55B and 55C illustrate a serial construction of a full length catheter device;

FIGS. 57A, 57B, 57C, 57D, 57E, 57F, 57G and 57H illustrate a tumor embolization method for a standard catheter;

FIG. 70 shows an in-vivo tumor flow model developed in Phase 1B of animal testing, in particular illustrating a normal blood flow pattern;

FIG. 71 shows the in-vivo tumor flow model of FIG. 70, with a standard embolization catheter maintaining a normal blood flow pattern;

FIG. 72 shows the in-vivo tumor flow model of FIG. 70, with an inventive embolization catheter creating blood flow redirection; and FIG. 73 is a table summarizing bead collection results of the animal testing.

DETAILED DESCRIPTION

The device of the present disclosure allows improved distribution of anti-cancer agents into target tumor vasculature by reducing arterial flow and pressure during drug and/or embolic agent injection. The present device reduces toxicity and complications by eliminating reflux of embolic materials and/or anti-cancer agents into proximal arterial branches and reduces or eliminates antegrade bypass of embolic materials and/or anticancer agents into distal arterial branches. Further, the present disclosure enables pressure measurement as a means to a quantitative endpoint of the procedure. Such a device can improve efficacy and reproducibility of the technique and reduce complications.

Figure 1:
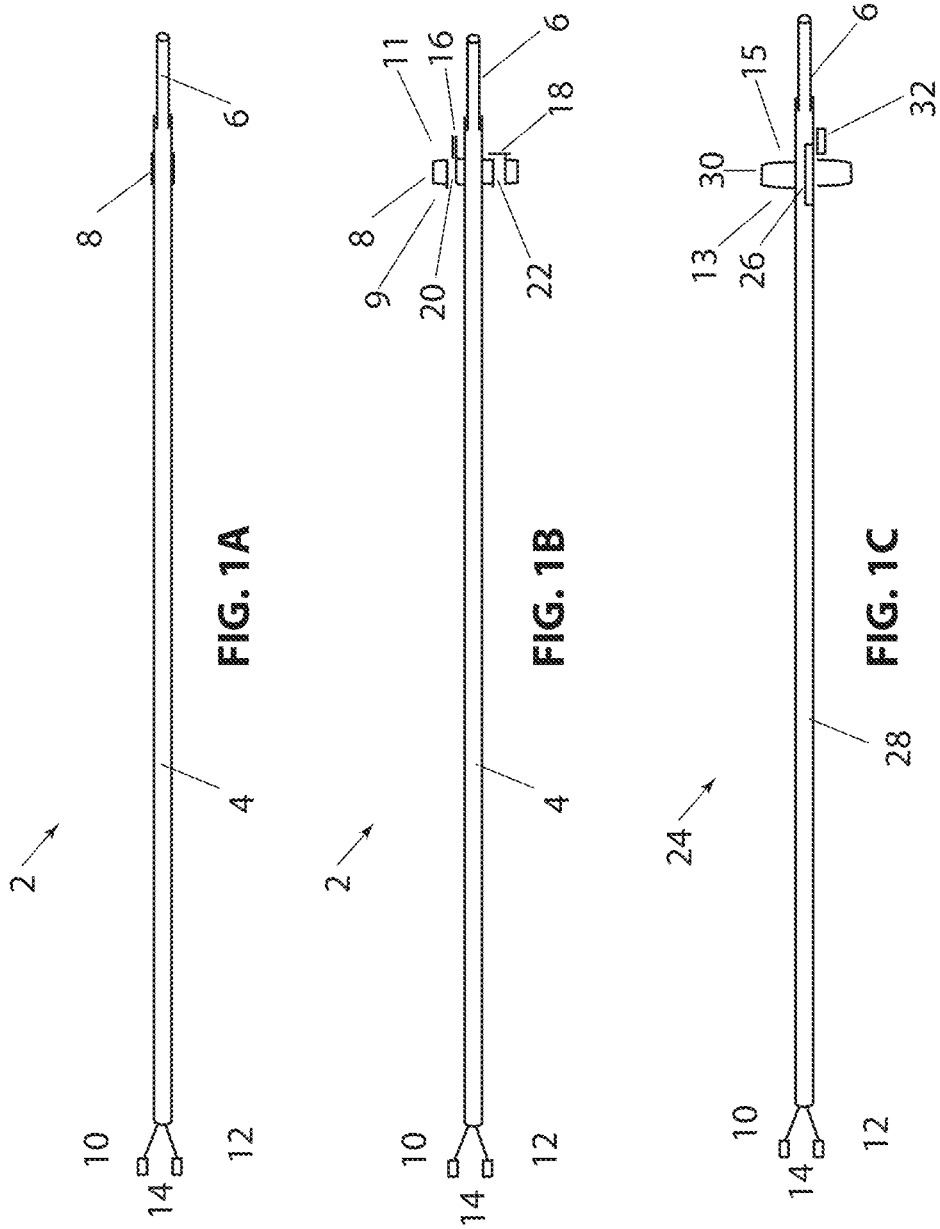
FIGS. 1A, 1B and 1C illustrate embodiments of the disclosure herein.

Referring to FIG. 1A, a longitudinal cross section of device 2 of the present disclosure is shown with catheter body 4, distal tip 6, balloon 8 (unexpanded configuration), balloon inflation tube 10, guidewire and injection tube 12 and fittings 14. Catheter body 4 can have a length of 10 cm to 400 cm, typically 60 cm to 250 cm and a diameter of 0.25 mm to 5 mm, typically 0.5 mm to 1.5 mm. Device 2 may or may not include a distal tip 6, the distal tip having a length of 1 mm to 50 mm, more typically from 5 mm to 30 mm. The balloon inflation tube 10, positioned at the proximal end of catheter body 4, is connected to, and in fluid communication with a balloon inflation lumen that runs longitudinally through the length of catheter body 4 and terminates at, and is in fluid communication with balloon 8. The guidewire and injection tube 12, positioned at the proximal end of catheter body 4, is connected to, and in fluid communication with a lumen that runs longitudinally through the length of catheter body 4 and terminates at the distal end or distal tip of catheter body 4, thereby allowing a guidewire to enter through fitting 14 and exit through the distal end of device 2 through catheter body 4. Fittings 14 are connected to each of balloon inflation tube 10 and guidewire and injection tube 12 and can connect to a syringe, inflation device or any other device or means to inject air, gas, fluid, suspensions, emulsions, contrast, therapeutic agents, embolic agents or any other material capable of being injected through balloon tube 10 or guidewire tube 12 and longitudinal lumens that run to the balloon or distal end of device 2.

Referring to FIG. 1B, a longitudinal cross section of a first embodiment of the present disclosure is shown, with device 2, balloon 8 (in the expanded configuration) having valve 16 in the open position and valve 18, in the closed position. In this embodiment flow channels 20 and 22 are constructed through balloon 8. Valves 16 and 18 allow fluid to flow in only one direction. Balloon 8 has a proximal side 9 and a distal side 11. By way of example, if fluid pressure is higher on the proximal side of balloon 8 and lower on the distal side of balloon 8, both valves 16 & 18 will open in response to the pressure difference and allow fluid to flow distally through the valves. If the pressure is higher on the distal side of balloon 8, valves 16 and 18 will close and prevent fluid from flowing proximally. Alternately, the valves can be position or constructed so that fluid can pass proximally and be prevented from flowing in the distal direction. Valves 16 and 18 are shown as a simple "flap" type valve, however, they can be any type of valve, such as a diaphragm that open and close in response to a pressure differential. Balloon 8 is shown with two channels and two valves; however there can be 1, 2, 3 or more channels and/or valves. Device 2 of this embodiment may include channels and may or may not include valves. If valves are not included, a bidirectional flow will result.

Referring to FIG. 1C, a longitudinal cross section of another embodiment of the present disclosure is shown with device 24 and channel 26 running through and within catheter body 28. Balloon 30 has a proximal side 13 and a distal side 15. Channel 26 extends from the proximal side of balloon 30 to the distal side of balloon 30. A valve 32 is illustrated over channel 26 on the distal side of balloon 30, however, if desired the valve can be positioned on the proximal side of channel 26 and balloon 30. The function and operation of valve 32 of this embodiment of the present disclosure is identical to that presented in FIG. 1A and FIG. 1B. As in this embodiment, if valve 32 is not included, a bidirectional flow will result.

Figure 2:
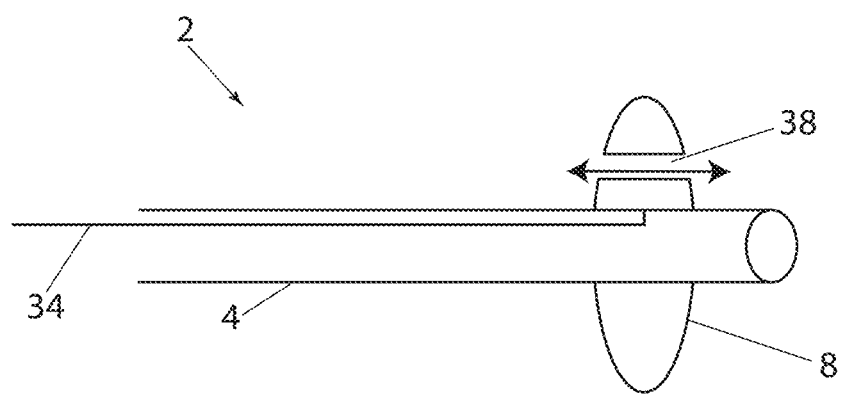
FIG. 2 illustrates a distal cross sectional view of a bidirectional embodiment.

FIG. 2 illustrates an exemplary embodiment of a longitudinal cross section of the distal end of device 2 with catheter body 4, balloon inflation lumen 34, balloon 8, and channel 38. Balloon inflation lumen 34 extends from the proximal end of catheter body 4 and exits at balloon 8. In this case, a valve in balloon 8 is not included and a bidirectional flow will result. The optimal balloon inflation lumen diameter is 0.1 mm to 0.5 mm; however this lumen can be in the range of 0.25 mm to 1 mm.

Figure 3:
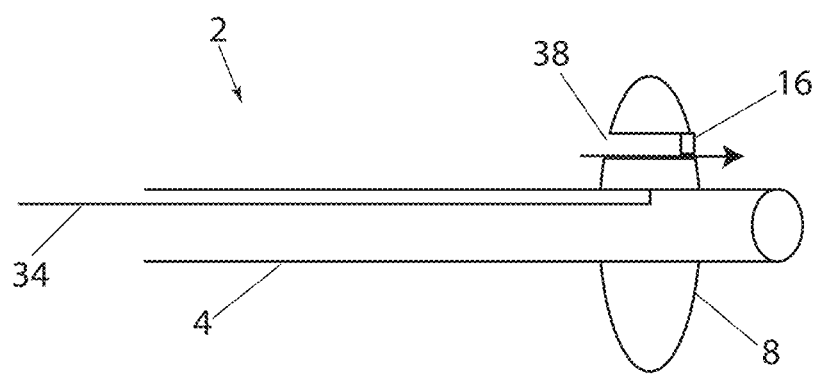
FIG. 3 illustrates a unidirectional embodiment.

FIG. 3 illustrates an example of a longitudinal cross section of the distal end of device 2 with catheter body 4, balloon inflation lumen 34, balloon 8, channel 38 and valve 16. Valve 16 is shown over the distal opening of channel 38 in the closed position, however if pressure is applied to the proximal valve surface through channel 38, the valve will allow fluid to pass distally. The valve 16 will prevent proximal flow. The valve can be positioned at the proximal or distal opening or anywhere within the cannel. Location and configuration of the valve will determine flow direction.

Figure 4:
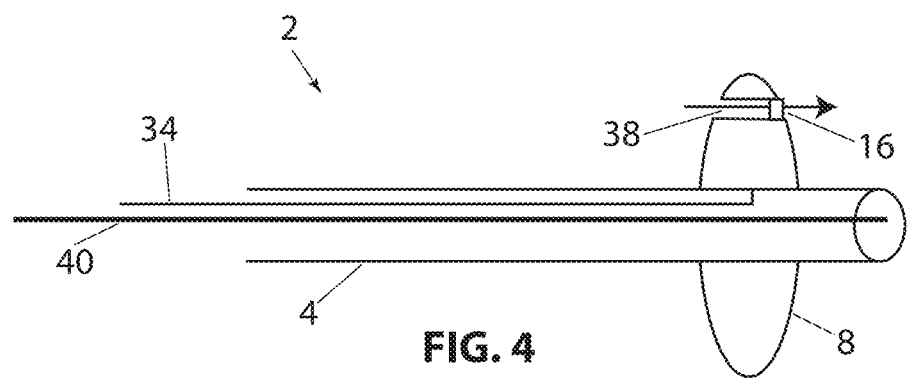
FIG. 4 illustrates a unidirectional embodiment with balloon inflation and guidewire/injection lumens.

Referring to FIG. 4, a longitudinal cross section of the distal end of device 2 is shown with catheter body 4, balloon inflation lumen 34, balloon 8, channel 38 and guidewire/injection lumen 40. Guidewire/injection lumen 40 extends from the proximal end of catheter body 4 and exits at the distal end of catheter body 4 or distal tip 6. The optimal guidewire/injection lumen diameter is 0.1 to 1.0 mm; however, this lumen can be in the range form 0.025 mm to 2 mm.

Figure 5:
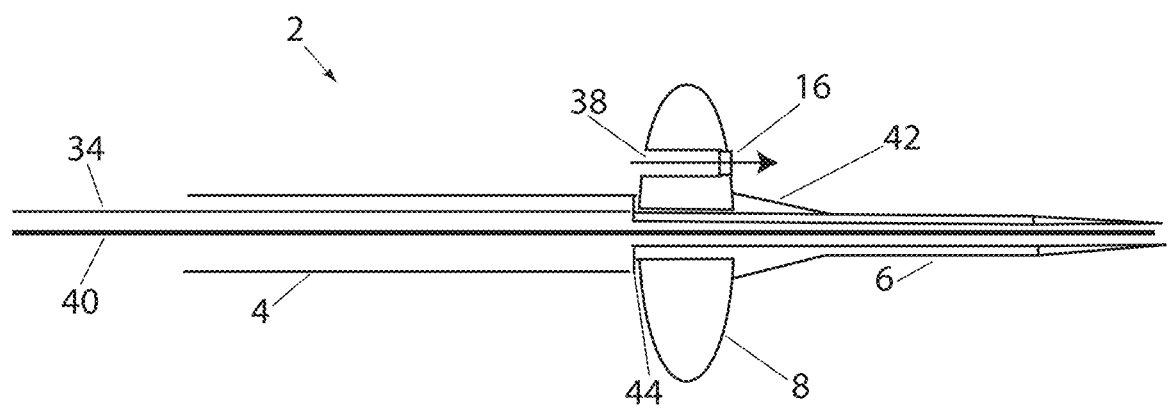
FIG. 5 illustrates an embodiment of the present disclosure including a distal tip and adapter.

Referring to FIG. 5, an example of a longitudinal cross section of the distal end of device 2 is shown with catheter body 4, balloon inflation lumen 34, balloon 8, channel 38, guidewire/injection lumen 40, adapter 42, balloon pocket 44 and distal tip 6. Distal tip 6 has an optimal diameter of 0.3 mm to 1.3 mm; however, distal tip 6 can range from 0.1 mm to 4 mm. Adapter 42 is adapted to create a smooth transition from the distal tip 6 to the catheter body 4. By way of example, if the distal tip 6 is 1 mm in diameter and the catheter body 4 is 2 mm in diameter, the adapter will taper from a diameter of 1 mm at its distal most point to 2 mm at its proximal most point to create a smooth transition from the smaller diameter distal tip to the larger diameter catheter body. As shown in FIG. 5, adapter 42 is positioned on the distal tip 6 at a location that is distal to distal end of catheter body 4, such that a balloon pocket 44 is formed between the distal end of catheter body 4 and the proximal end of adapter 42. Balloon pocket 44 holds unexpanded balloon 8 such that its unexpanded profile is minimized. Optimally balloon 8 would conform to an outer diameter that is equal to the diameter of the catheter body 4. By way of example, if the distal tip diameter is 1 mm and the catheter body is 2 mm, a balloon pocket is formed that is 0.5 mm deep. If balloon 8 is no more than 0.5 mm thick when unexpanded, it will lie equal to or below the surface of catheter body 4. This allows facilitation of the movement of the caterer within the artery or vein.

Figure 6:
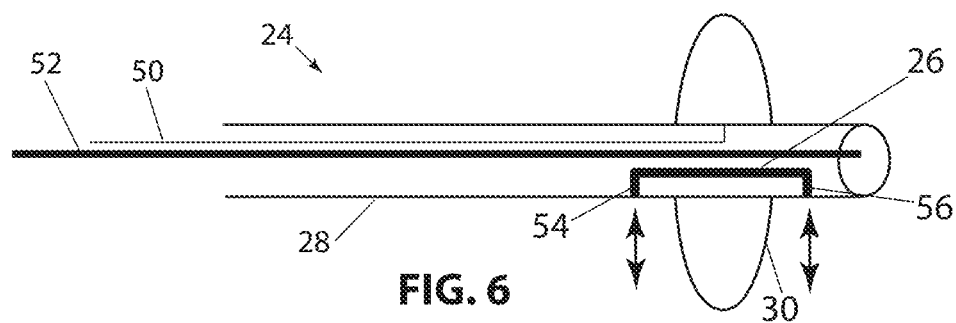
FIG. 6 illustrates an embodiment of the present disclosure with a bidirectional channel within the catheter.

Referring to FIG. 6, a longitudinal cross section of the distal end of device 24 is shown with catheter body 28, balloon inflation lumen 50, guidewire/injection lumen 52, balloon 30, and channel 26 with proximal port 54 and distal port 56. Channel 26 passes through and within catheter body 28 and extends from the proximal side of balloon 30 to the distal side of balloon 30. Port 54, at the proximal end of channel 26 is in fluid communication with the outside of the catheter body that is proximal to balloon 30 and port 56, at the distal end of channel 26, is in fluid communication with the area outside of catheter body 28 that is distal to the balloon 30. In this case, the flow through channel 26 is bidirectional. The optimal channel diameter is 0.1 mm to 1 mm; however this channel can be in the range of 0.05 mm to 2 mm.

Figure 7:
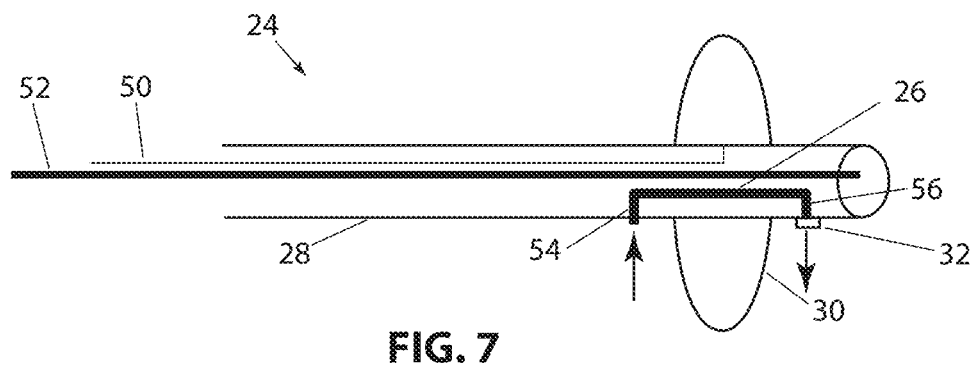
FIG. 7 illustrates an embodiment of the present disclosure with a unidirectional channel.

FIG. 7 illustrates an exemplary embodiment of a longitudinal cross section of the distal end of device 24 with catheter body 28, balloon inflation lumen 50, guidewire/injection lumen 52, balloon 30, valve 32 and channel 26 with proximal port 54 and distal port 56. Channel 26 passes through and within catheter body 28 and extends from the proximal side of balloon 30 to the distal side of balloon 30. Port 54, at the proximal end of channel 26 is in fluid communication with the outside of the catheter body that is proximal to balloon 30 and port 56, at the distal end of channel 26, is in fluid communication with the area outside of catheter body 28 that is distal to the balloon 30. Valve 32, is shown at the opening of port 56 of channel 26. Valve 32 allows flow in the distal direction and prevents flow in the proximal direction. In this case, the flow through channel 26 is unidirectional. The optimal channel diameter is 0.1 mm to 1 mm; however this channel can be in the range of 0.05 mm to 2 mm. The valve can be positioned at the proximal or distal opening or anywhere within the channel. Location and configuration of the valve will determine flow direction.

Figure 8:
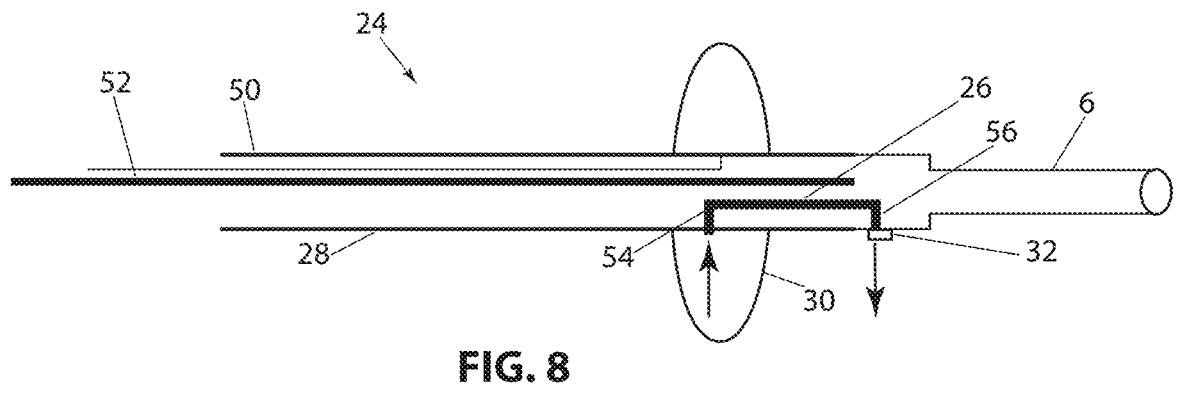
FIG. 8 illustrates a device of the present disclosure with a distal tip.
Figure 9A:
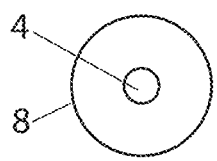
FIG. 9A shows a linear cross section through the catheter and balloon.
Figure 9B:
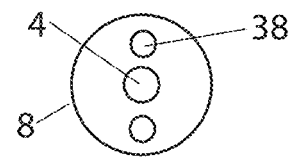
FIG. 9B shows a linear cross section through the catheter and balloon and two circular bidirectional channels.
Figure 9C:
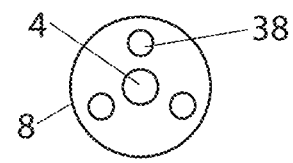
FIG. 9C shows a linear cross section through the catheter and balloon and three circular bidirectional channels.
Figure 9D:
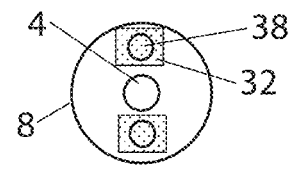
FIG. 9D shows a linear cross section through the catheter and balloon and two circular unidirectional bypass channels with individual valves on each channel.
Figure 9E:
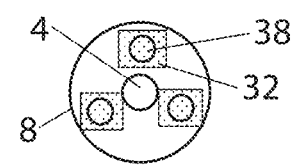
FIG. 9E shows a linear cross section through the catheter and balloon and three circular unidirectional bypass channels with individual valves on each channel.
Figure 9F:
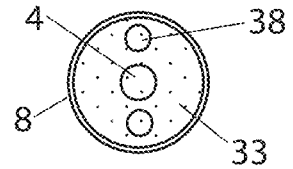
FIG. 9F shows a linear cross section through the catheter and balloon and two circular unidirectional channels with a one-piece valve covering both channels.
Figure 9G:
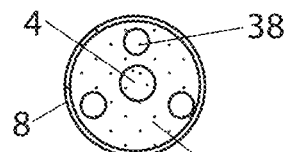
FIG. 9G shows a linear cross section through the catheter and balloon and two circular unidirectional channels with a one-piece valve covering three channels.
Figure 9H:
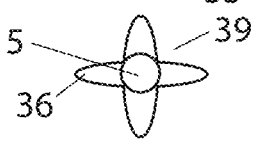
FIG. 9H shows a linear cross section through the catheter and balloon and four bidirectional bypass channels formed from pleats in the balloon.
Figure 9I:
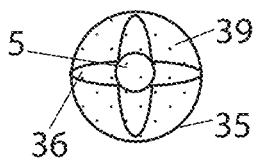
FIG. 9I shows a linear cross section through the catheter and balloon and four unidirectional bypass channels formed from pleats in the balloon and a one-piece valve covering all 4 channels.
Figure 9J:
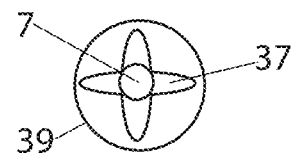
FIG. 9J shows a linear cross section through the catheter and balloon and four bidirectional channels which radiate outward from the catheter.
Figure 9K:
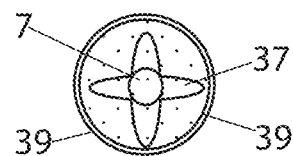
FIG. 9K shows a linear cross section through the catheter and balloon and four unidirectional channels which radiate outward from the catheter and a one-piece valve covering all four valves.
Figure 9L:
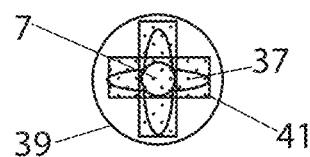
FIG. 9L shows a linear cross section through the catheter and balloon and four unidirectional channels which radiate outward from the catheter outward and a single cross shaped valve covering all four channels.

Referring to FIG. 8, a longitudinal cross section of the distal end of device 24 is shown with catheter body 28, balloon inflation lumen 50, guidewire/injection lumen 52, balloon 30, valve 32, channel 26 and distal tip 6.

Referring to FIG. 9, linear cross sections through catheter body 4 and balloon 8 are shown. FIG. 9 illustrates examples of flow channels through a balloon positioned on a catheter, however, various alternatives, modifications, and equivalents may be used. FIG. 9A shows catheter 4 and balloon 8 without a channel. FIG. 9B shows catheter 4 and balloon 8 with two channels 38 through balloon 8. In this case the flow is bidirectional. FIG. 9C shows a catheter and balloon with three bidirectional channels. FIG. 9D shows a catheter 4 with a balloon 8 with two channels, each with a one-way valve. In this case the channel flow in each channel is unidirectional. FIG. 9E shows catheter 4 with balloon 8 and three channels 38, each with an independent valve 38. The flow is unidirectional. FIG. 9F is a catheter and balloon with two channels and a single circumferential valve 33 that covers both channels 38 and allows flow in only 1 direction. FIG. 9G shows a catheter 4 and balloon 8 with three channels and a single circumferential valve 33 that covers all three channels. FIG. 9H shows a catheter 5, and four bidirectional channels 39 that are formed by pleating balloon 36 from the outer circumference of the expanded balloon, inward toward the central catheter and securing the inner apex of the balloon to the catheter, thereby forming triangular channels which radiate outward from the central catheter, forming a "V" shape. The lower point of the 'V' is positioned at the catheter surface and the open end of the "V" is positioned at the outer circumference of the circle defined by the largest diameter of the inflated balloon. FIG. 9I shows four channels 39, with a single circumferential valve 35 covering all four triangular channels. Although the figure shows four channels, the device of this disclosure can have one, two, three, four or any number of channels. FIG. 9J shows a catheter 7 and a balloon 39 with four channels 37 that are formed by pleating the balloon 39 from the inner catheter 7 toward the outer circumference of the expanded balloon 39. FIG. 9K shows four channels 37 as in FIG. 9J with a single circumferential valve 39 that covers all four channels 37. FIG. 9L shows four channels 37 as in FIG. 9J with a one piece cross-shaped flap valve 41.

While the above is a complete description of exemplary embodiments of the present disclosure, various alternatives, modifications, and equivalents may be used. Therefore, the above description should not be taken as limiting the scope of the disclosure, which is defined by the appended claims and the claims in any subsequent applications claiming priority hereto.

Figure 10:
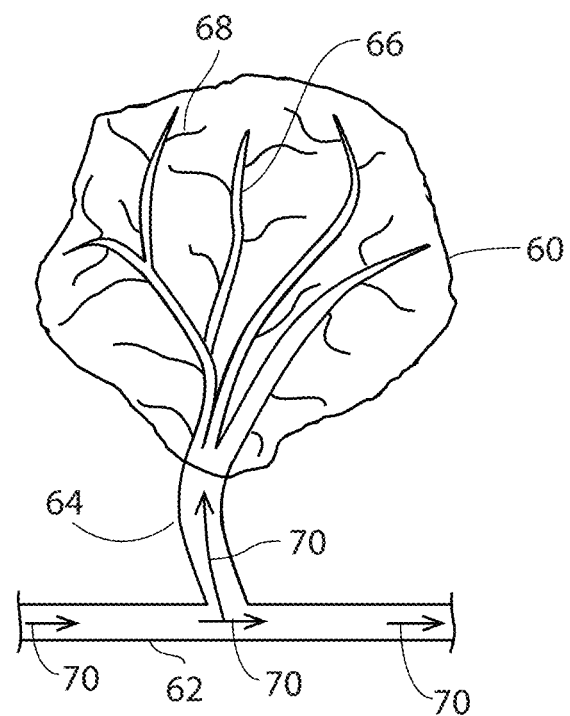
FIG. 10 shows a tumor and associated vasculature.

FIG. 10 illustrates a tumor and its associated vasculature with tumor 60, main artery 62, side branch artery 64, tumor artery 66, tumor capillary 68 and antegrade arterial flow direction illustrated by arrows 70.

Figure 11:
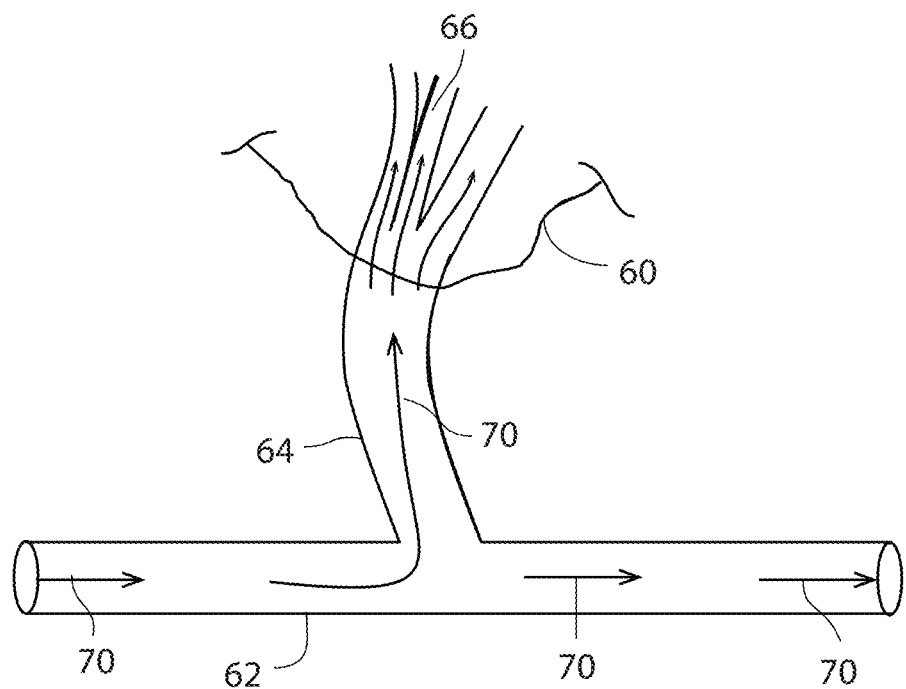
FIG. 11 shows an expanded view of a tumor and its vasculature including blood flow direction.

FIG. 11 is an expanded view of FIG. 10 with tumor 60, main artery 62, side branch artery 64, tumor artery 66 and antegrade arterial flow direction illustrated by arrows 70.

Figure 12:
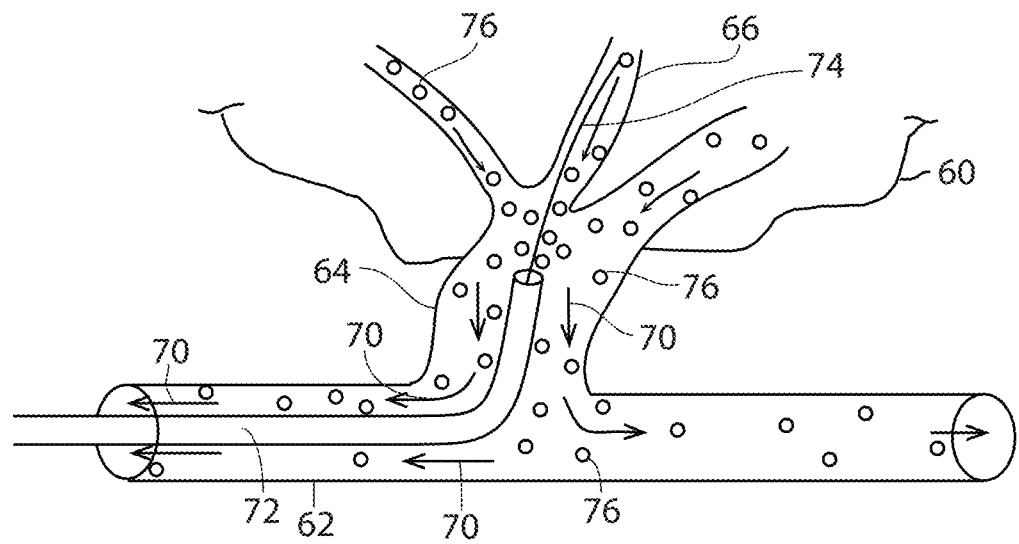
FIG. 12 illustrates a standard micro-catheter over a guidewire inside the tumor vasculature with injection.

FIG. 12 illustrates injection of fluid 76 using a standard micro-catheter 72 with tumor 60, main artery 62, side branch artery 64, tumor artery 66, guidewire 74 and retrograde arterial flow direction illustrated by arrows 70. In this instance, injection pressure and flow volume of the fluid 76 that may contain anti-cancer drugs, radioembolic substances, chemoembolic substances, embolic agents or the like, through microcatheter 72 is higher than the tumor vasculature can accept causing a reversal of fluid flow and blood flow in tumor artery 66, side branch artery 64 and main artery 62. This retrograde flow causes the injected fluid 76 to enter the main artery, flowing in both directions and into the general circulation resulting in the injected fluid traveling to non-target tissues and organs. This unintended delivery of fluid 76 to non-target sites is undesirable and must be avoided since it can cause serious complications. The present disclosure solves this problem by preventing reflux and associated non-target delivery of fluid 76.

Figure 13:
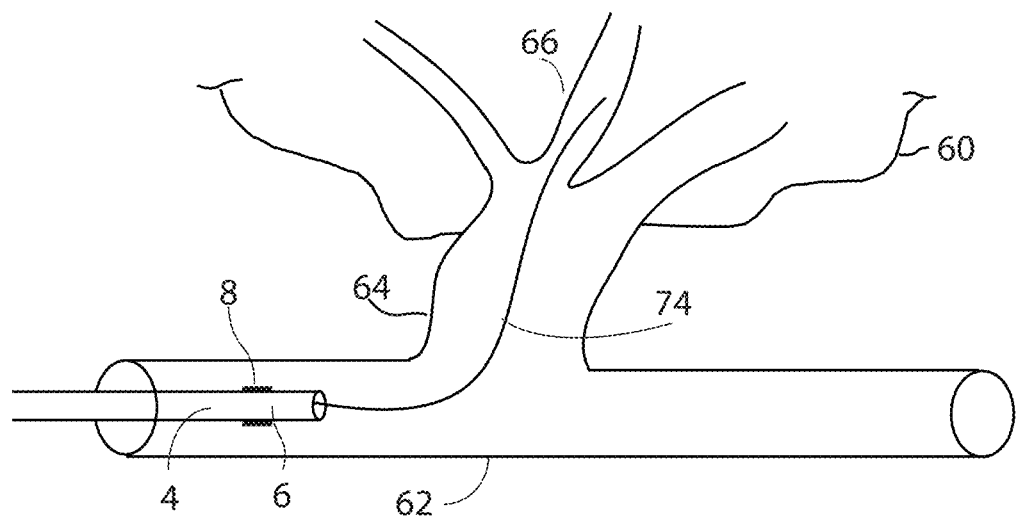
FIG. 13 illustrates a catheter of the present disclosure over a guidewire and inside a main artery

FIG. 13 illustrates catheter 4 of the present disclosure entering the main artery with balloon 8 and distal tip 6. Although the entry point from outside the body is typically through the femoral artery at the groin, any artery or vein from any location on the body can be used for access provided that it creates a pathway to the target vasculature.

Figure 14:
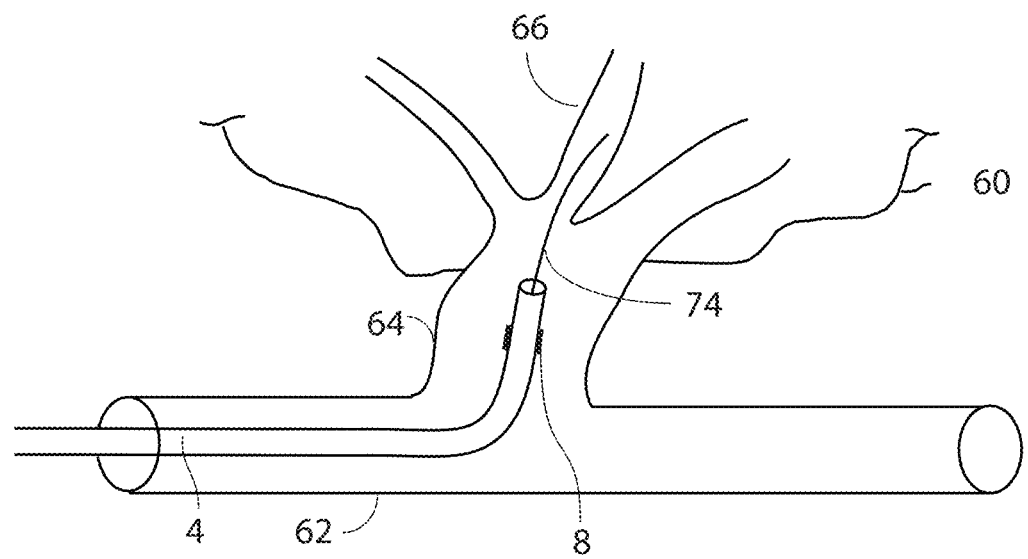
FIG. 14 illustrates a catheter of the present disclosure over a guidewire and inside the branch artery.

FIG. 14 illustrates catheter 4 with balloon 8, of the present disclosure, following guidewire 74 into side branch artery 64.

Figure 15:
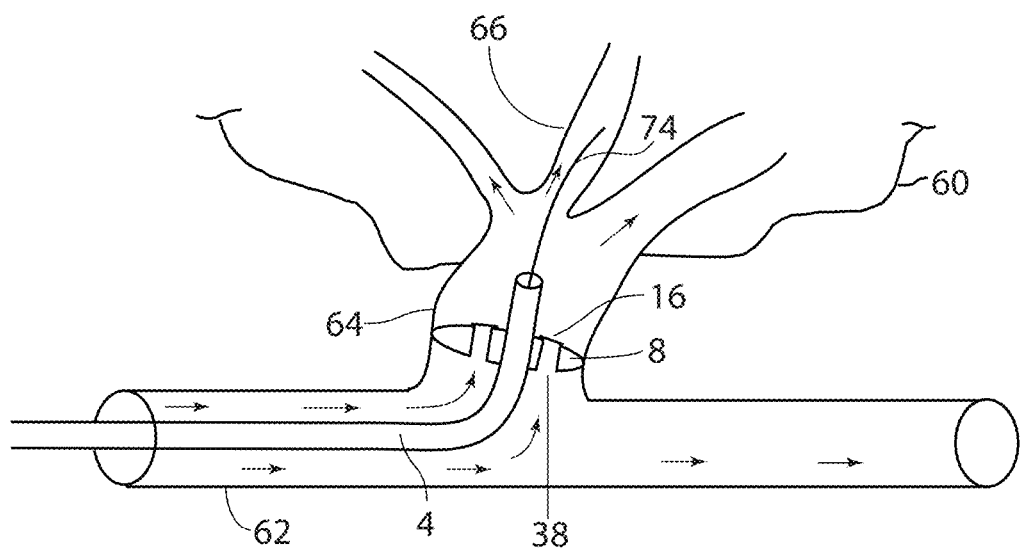
FIG. 15 illustrates a catheter of the present disclosure with inflated balloon and closed valves.

FIG. 15 illustrates catheter 4, inside the branch artery 64 with balloon 8 in the expanded configuration, channels 38 and valves 16. Valves 16 are illustrated in the closed position immediately following the inflation of balloon 8.

Figure 16:
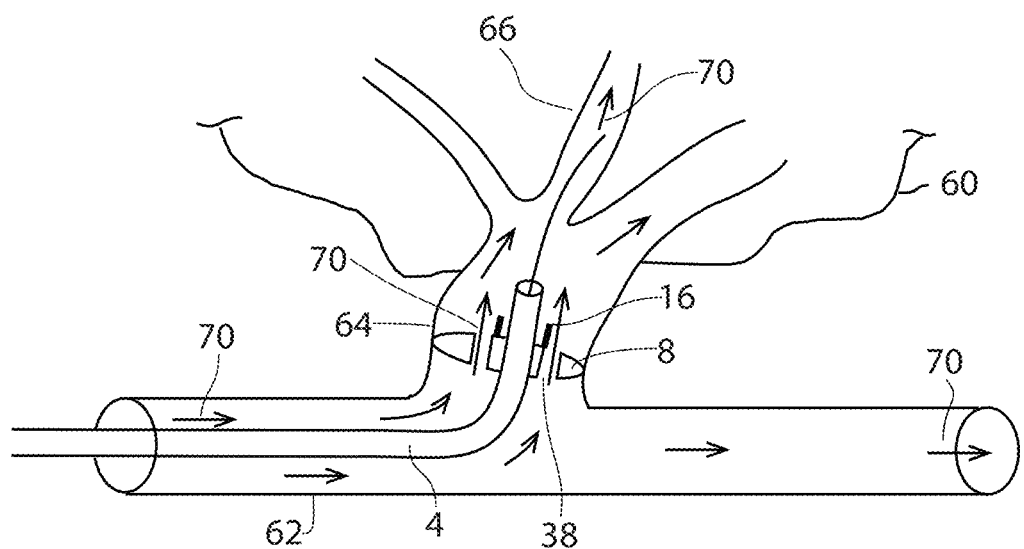
FIG. 16 illustrates a catheter of the present disclosure with inflated balloon and open valves.

FIG. 16 illustrates catheter 4, inside the branch artery 64 with balloon 8 in the expanded configuration, channels 38 and valves 16. Valves 16 are illustrated in the open position since antegrade blood flow as indicated by arrows 70 and associated blood pressure causes these valves to open and allow the blood to continue to flow in the antegrade direction and into the tumor vasculature.

Figure 17:
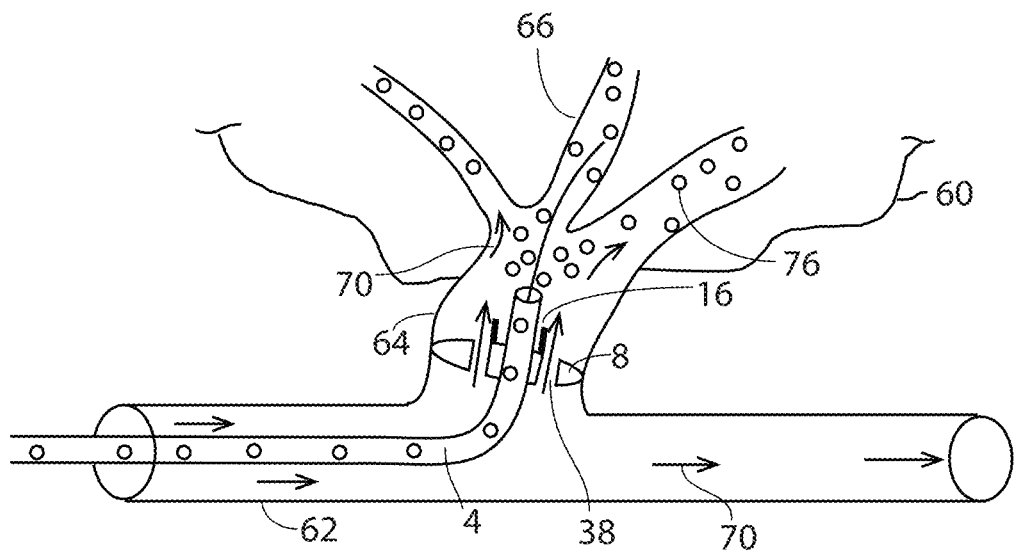
FIG. 17 illustrates a catheter of the present disclosure with inflated balloons, open valves and initiation of fluid injection.

FIG. 17 illustrates the initial injection of fluid 76 into side branch artery 64 through catheter 4, channels 38 and open valves 16. When the injection is initiated, the antegrade blood flow carries the injection fluid 76 into the tumor vasculature including tumor arteries 66, and capillaries 68.

Figure 18:
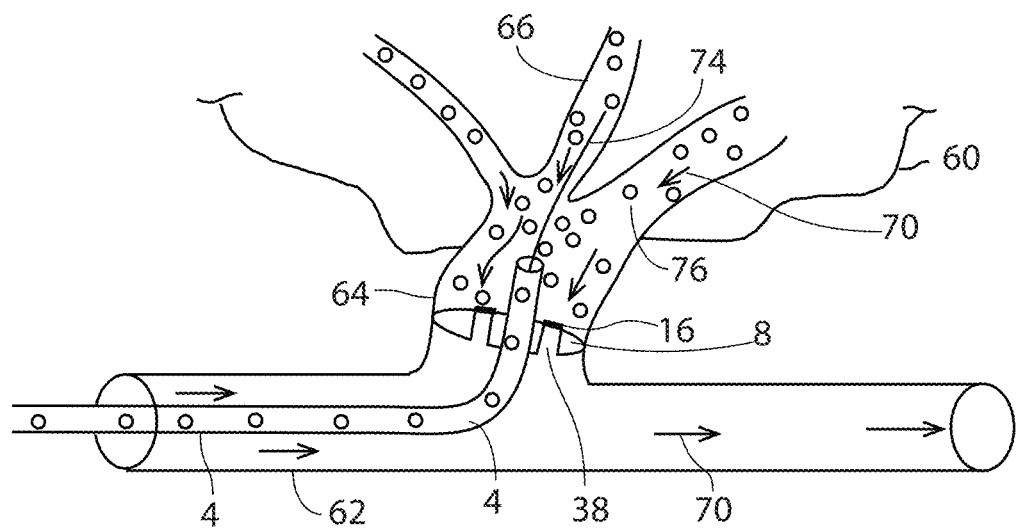
FIG. 18 illustrates a catheter of the present disclosure during injection with inflated balloons and valves closed.

FIG. 18 illustrates injection of fluid 76 at a point when fluid pressure increases within the tumor vasculature and concomitant retrograde arterial blood flow and injection fluid flow in the direction as illustrated by arrows 70. Shown in this figure are catheter 4 of the present disclosure with tumor 60, main artery 62, side branch artery 64, tumor artery 66, and guidewire 74. Injection fluid 76, may contain anti-cancer drugs, radioembolic substances, chemoembolic substances, embolic agents or the like, which can cause serious complications if delivered to non-target sites. In this case, the retrograde pressure causes valves 16 to close and prevents the reflux of injection fluid into the general circulation, thereby preventing complications associated with delivery of injection fluid to non-target sites.

Figure 19:
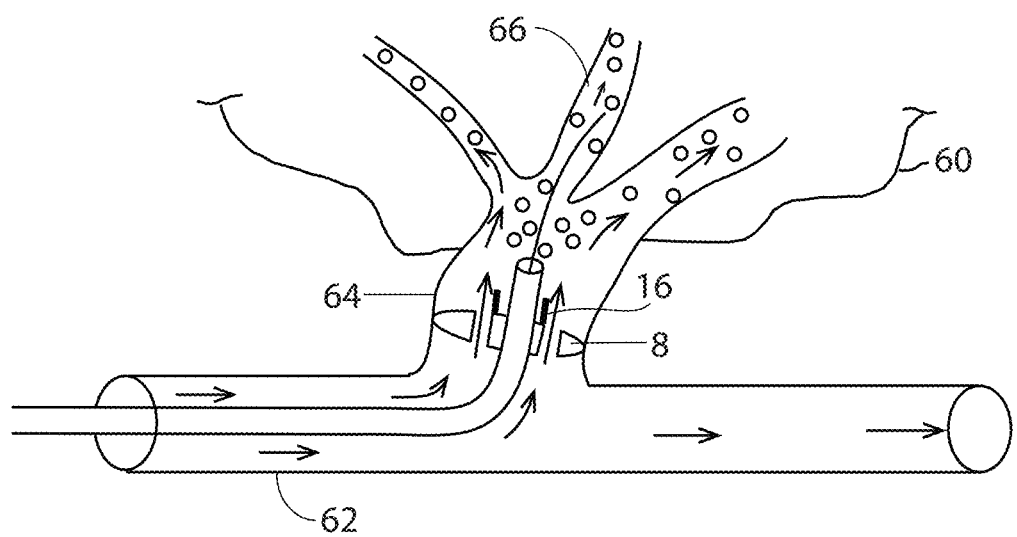
FIG. 19 illustrates a catheter of the present disclosure at a period of time following the completion of injection with inflated balloon and open valves.

FIG. 19 illustrates a point in time following the completion of fluid injection. At this point, the pressure in the vasculature that is the distal to balloon 8, including side branch 64 and tumor artery 66, is reduced below normal blood pressure due to the gradual uptake of the injected fluid into the tumor vasculature. The blood pressure on the proximal surface of balloon 8 and valves 16 cause them to open allowing antegrade blood flow to be reestablished. When this occurs, the excess fluid 76 distal to balloon 8 and within the side branch artery 64 and tumor vasculature, including tumor artery 66 and tumor capillaries 68, is flushed forward and up into the tumor vasculature, thereby enabling delivery of the entire fluid dose and eliminating fluid reflux and associated complications.

Figure 20:
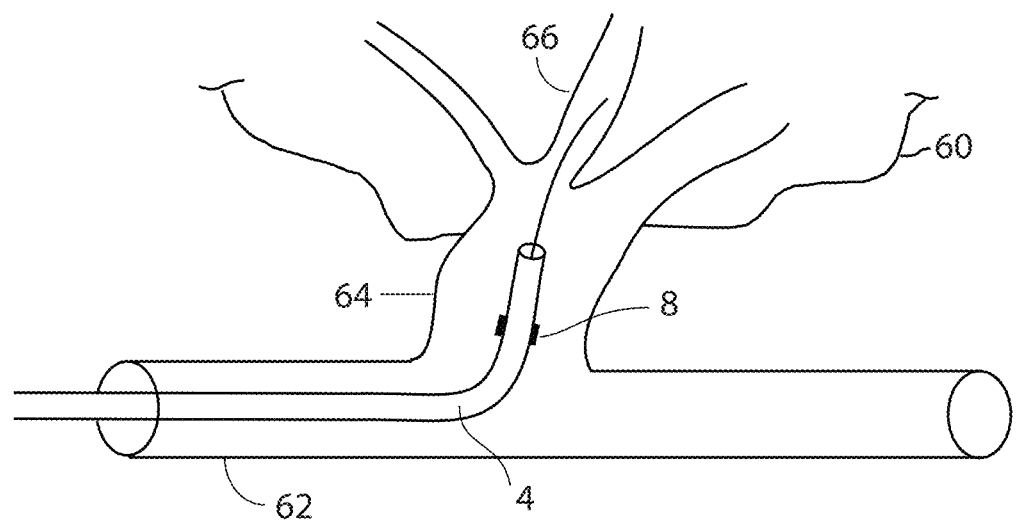
FIG. 20 shows the deflation of the balloon.

FIG. 20 illustrates the deflation of balloon 8 on catheter 4.

Figure 21:
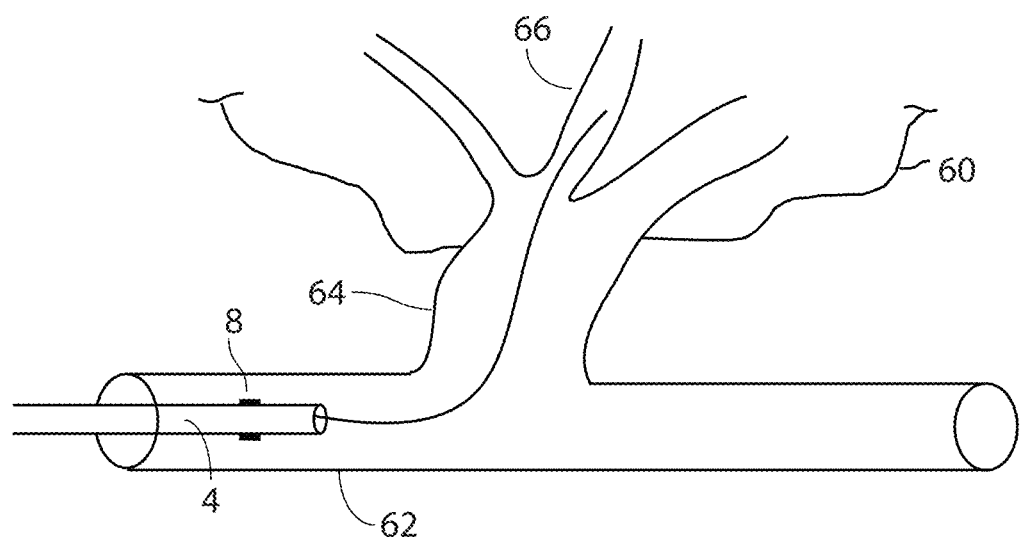
FIG. 21 shows the withdrawal of the catheter into a main artery.

FIG. 21 illustrates the withdrawal of catheter 4 into the main artery 62.

Figure 22:
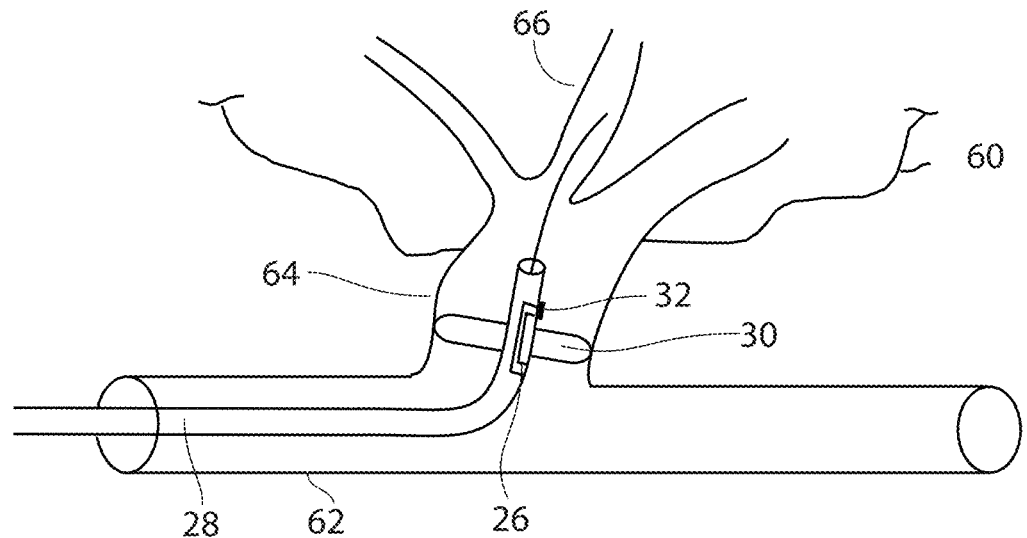
FIG. 22 shows an embodiment of the present disclosure with a channel within the catheter and closed valve.

FIG. 22 illustrates another embodiment of the present disclosure as described in FIGS. 6, 7 and 8. In this case valve 32 on the distal end of channel 26 of catheter 28 is in the closed position.

Figure 23:
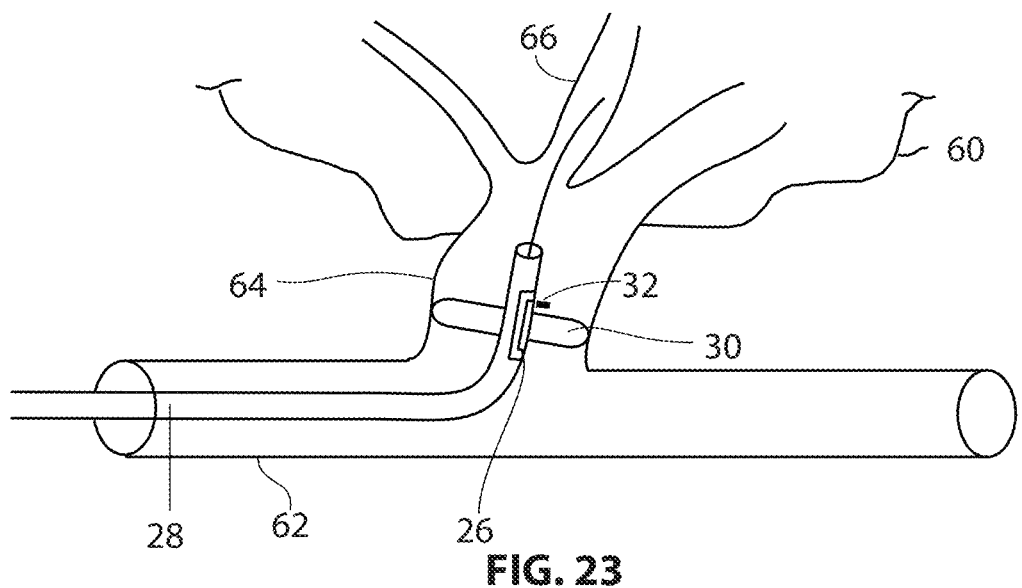
FIG. 23 shows an embodiment of the present disclosure with a channel within the catheter and open valve.

FIG. 23 illustrates an embodiment of FIG. 22 with valve 32 in the open position.

A Method, according to the present disclosure is illustrated by FIGS. 13 through 21; the method applies to both the embodiment illustrated in FIGS. 1B, 2, 3, 4 and 5 and the embodiment illustrated in FIGS. 1C, 6, 7, 8, 22 and 23.

Figure 24A:
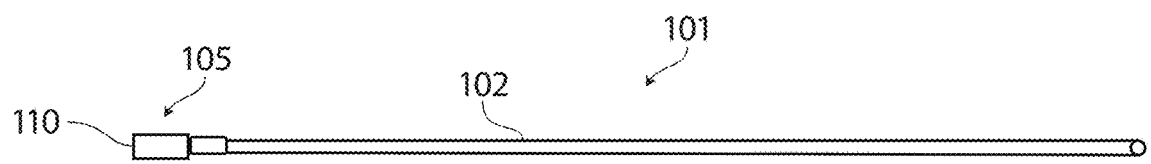
FIG. 24A illustrates a standard microcatheter.

Referring to FIG. 24A, a longitudinal cross section of a standard single lumen straight tip catheter 101, having a proximal and distal end, is shown with catheter body 102, and hub 105. Hub 105, positioned at the proximal end, further comprises guidewire/injection lumen 110, in fluid communication with a catheter lumen longitudinally oriented and extending from hub 105 and exiting at the distal end of the catheter body 102. The proximal hub connects to a syringe or other means to inject fluids via a luer fitting, thereby allowing injection of a fluid through the longitudinal lumen and exit at the distal end of catheter body 102.

Figure 24B:
FIGS. 24B, 24C, 24D and 24E illustrate a cross sectional view of a sequential construction of an embodiment of the present disclosure.
Figure 24C:
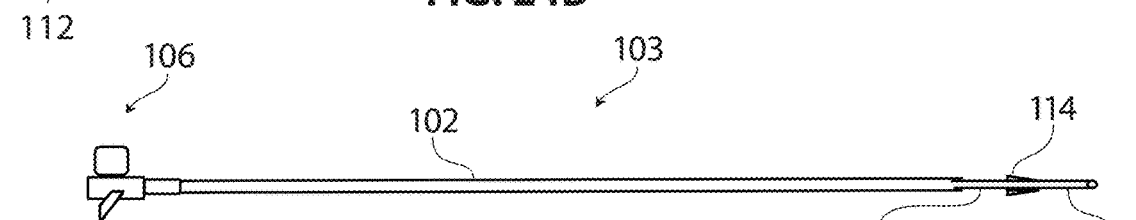
Figure 24D:
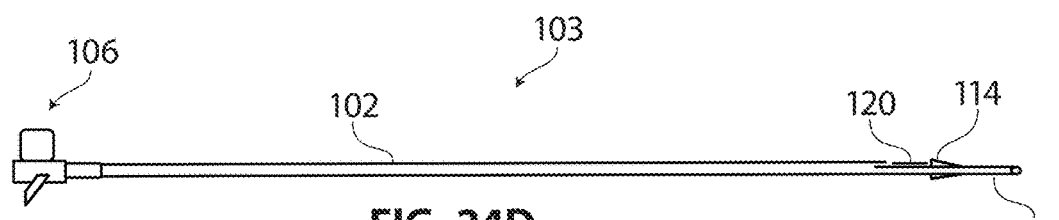
Figure 24E:
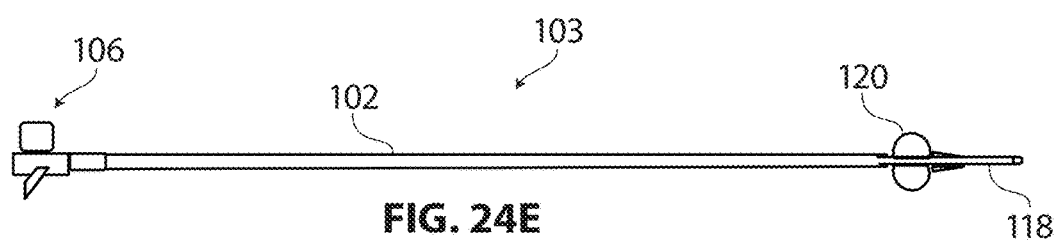

Referring to FIG. 24B through 24E, longitudinal cross-sections of a sequential assembly of a preferred embodiment of the present disclosure is shown. Referring to FIG. 24B, device 103 is shown, having a proximal and a distal end, catheter body 102, catheter extension 104 and hub 106. Hub 106 further comprises handle 109, guidewire/injection luer fitting 110 and balloon fill luer fitting 112. Luer fitting 110 is in fluid communication with a first longitudinal guidewire/ injection lumen of catheter body 102, extending to the distal end of catheter extension 104, and luer fitting 112, in fluid communication with a second longitudinal balloon fill lumen of catheter body 102, extending to a balloon fill port located near the distal end of catheter body 102. FIG. 24C further comprises nose cone 114, positioned on catheter extension 104, forming balloon pocket 116 disposed between the distal end of catheter body 102 and nose cone 114. Further, a portion of catheter extension 104 can, if desired, extend distal to nose cone 114, thereby forming distal tip 118. FIG. 24C, further illustrates occlusion balloon 120 in a radially compressed configuration and FIG. 24E illustrating balloon 120 in a radially expanded configuration. Hubs 106 can be constructed from styrene, polyurethane, polypropylene, lipid resistant polycarbonate, polycarbonate, Pebax (polyether block amide), of any durometer, or any convenient material and can have any configuration, including, but not limited to, a solid structure comprising two lumens or tubular extensions of the lumens of catheter body 102, provided that they are in fluid communication as described above. Catheter body 102 can be formed from any plastic or thermoplastic material including polyurethane, PTFE, polyimide, polypropylene, Pebax or the like, and can comprise a single section or multiple sections of different diameter, durometer, braid or coil reinforcement or any convenient construction with a diameter of between 1 Fr and 10 Fr more typically of 2 Fr to 5 Fr. Catheter extension 104 can have a diameter of 0.5 Fr to 5 Fr, more typically of 1 Fr to 3 Fr and can be absent or can be of any length, typically 2 mm to 30 mm, more typically from 5 mm to 20 mm. If the catheter extension 104 extends beyond nose cone 114, the section distal to the nose cone forms the distal tip 118. Distal tip 118 is advantageous when injecting deep into the tumor vasculature is desired and will also help tracking of device 103 over a guidewire around sharp corners and through a tortuous vasculature path. Nose cone 114 can be made from any polymer or metal or can be formed from a radiopaque marker band. Balloon pocket 116 can be of any length between 2 mm and 50 mm, more typically between 5 mm and 20 mm. Occlusion balloon 120 has a longitudinal length of 1 mm to 30 mm, more typically of 2 mm to 10 mm and a diameter of 1 mm to 50 mm, typically from 2 mm to 10 mm and can be composed of silicone, polyurethane, polyethylene, PET (polyethylene terephthalate), nylon or the like and can be of any configuration or of any length or shape and can be glued, chemically bonded, heat bonded, RF welded, sonically fused, compressed or crimped under a collar to catheter 102 or catheter extension 104.

Figure 25A:
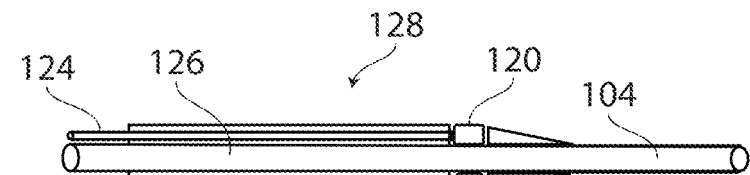
FIGS. 25A and 25B illustrate a cross sectional view of the distal portion of one embodiment of the device according to the present disclosure.
Figure 25B:
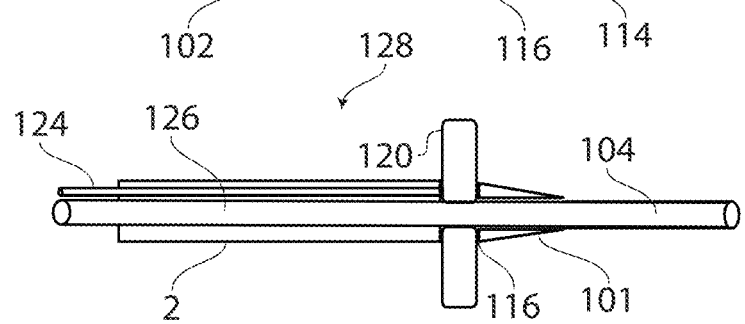

Referring to FIG. 25A, a distal section of a device 128 of a preferred embodiment of the present disclosure is shown and includes catheter body 102, catheter extension 104, nose cone 114, balloon pocket 116, balloon fill lumen 124, guidewire/injection lumen 126 and radially compressed balloon 120. Referring to FIG. 25B, balloon 120 is shown in its radially expanded configuration. Balloon fill lumen 124 can be of any convenient shape including but not limited to round, semicircular, or crescent or any shape, typically optimized to provide maximum area and flow rate. Guidewire/injection lumen 126 is typically round, having a diameter of 0.005" to 0.1", more typically from 0.01" to 0.05"; however, it can be of any desirable shape.

Figure 26A:
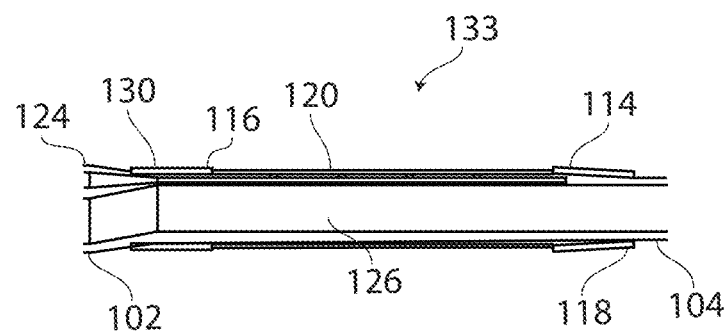
FIGS. 26A and 26B illustrate a view of an embodiment including an occlusion balloon concealed within pocket formed between proximal and distal surfaces.
Figure 26B:
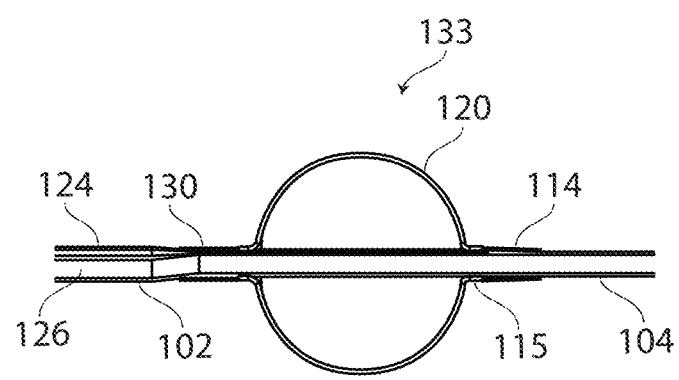

Referring to FIG. 26A, the distal end 133 of an embodiment of the present disclosure is shown with catheter body 102, catheter extension 104, nose cone 114, balloon pocket 116, balloon fill lumen 124, guidewire/injection lumen 126 and radially compressed balloon 120. In this instance, the balloon pocket 116 is formed between a proximal collar 130 and a distal collar 114, tapered forward thereby forming a nose cone. The balloon bonding tails 115 can be bonded within the pocket or compressed or bonded under collars 114 and 130. Distal collar 130 can comprise a metal, such as a radiopaque marker band or a plastic such as heat shrink tubing and can be 1 mm to 20 mm in length, more typically from 2 mm to 10 mm. Balloon fill lumen 124 is shown traveling under balloon pocket 116 and ending at its distal end. Guidewire/injection lumen 126 is shown traveling longitudinally through catheter 102 and catheter extension 104, ending at the distal end of the catheter. Balloon 120 is shown tucked into pocket 116 with outer diameter substantially no larger than the outer diameter of catheter body 102. FIG. 26B shows the same construction as FIG. 26A with balloon 120 in its radially expanded configuration.

Figure 27A:
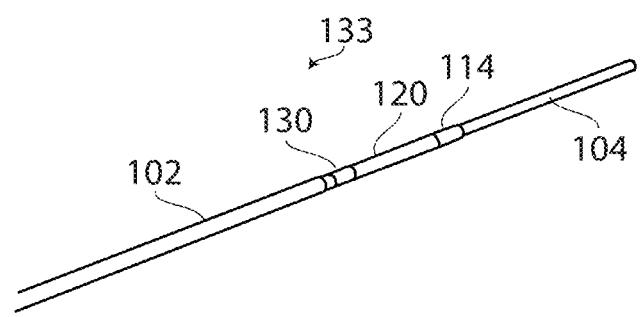
FIGS. 27A and 27B illustrate a distal catheter with and occlusion balloon unexpanded and expanded.
Figure 27B:
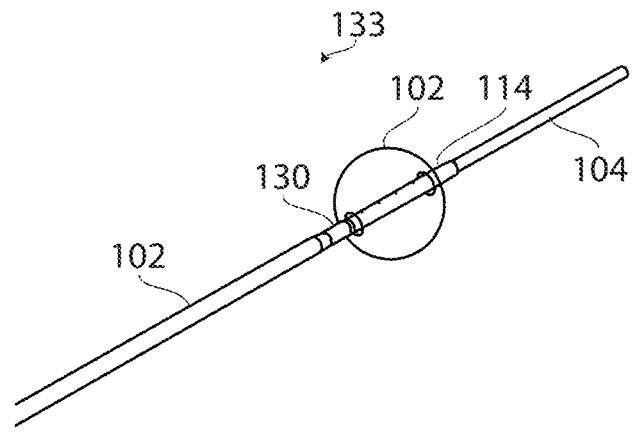

Referring to FIG. 27A, a view of distal section 133 is shown and further illustrates that the profile of a preferred embodiment of the present disclosure, including the radially compressed balloon 120, the distal collar 114 and the proximal band 130, have an outer diameter equal to or less than that of catheter body 102. FIG. 27B shows the same construction as FIG. 27A with balloon 120 expanded from pocket 116 and between collars 114 and 130.

Figure 28A:
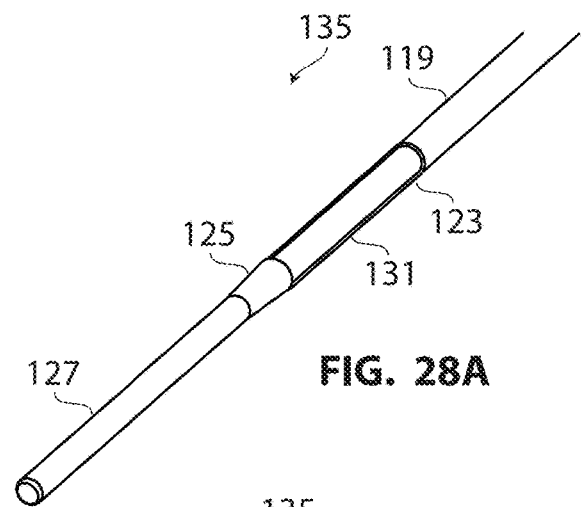
FIGS. 28A, 28B, 28C, and 28D illustrate an embodiment of the present disclosure including a two layer catheter.
Figure 28B:
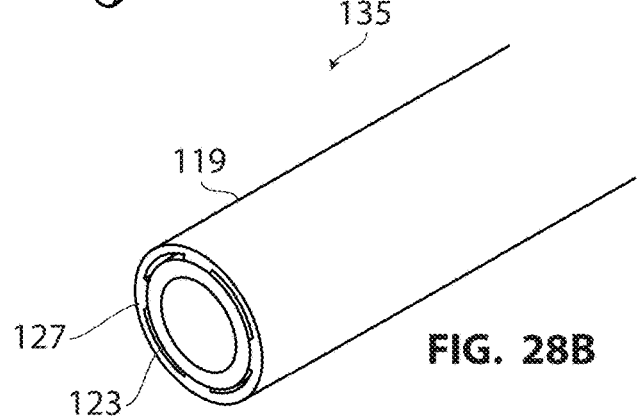
Figure 28C:
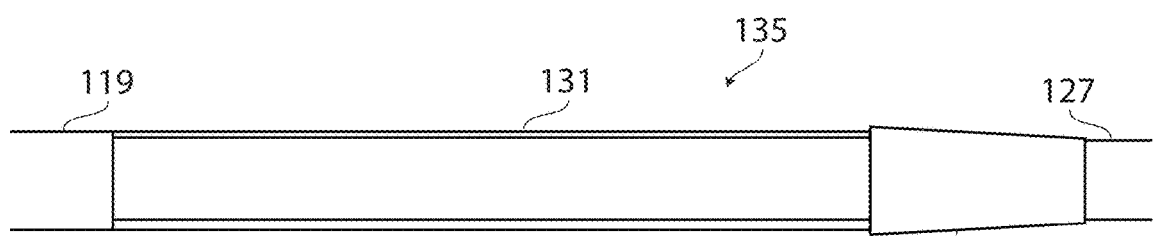
Figure 28D:
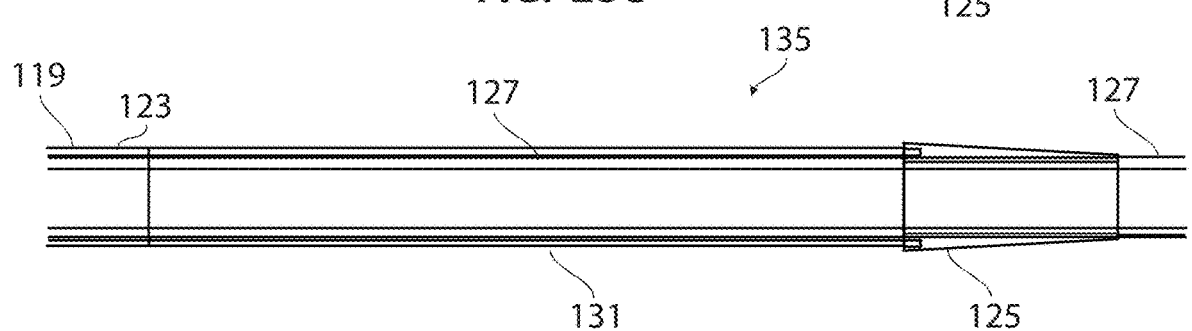

Referring to FIG. 28A, a distal section of an alternate embodiment 135 of the present disclosure is shown with outer catheter 119, inner catheter 127, nose cone 125, radially constrained balloon 131 and catheter channels 123. The outer catheter 119 is adapted over inner catheter 121, the catheters configured to provide a radially distributed space between inner and outer catheters extending longitudinally along the length of device 135. Outer and inner catheters can have a length of 10 cm to 250 cm, more typically 50 cm to 150 cm and a diameter of between 0.5 Fr and 10 Fr more typically of 1 Fr to 5 Fr. Inner catheter 127 can have a length less than, equal to, or longer than the outer catheter 119, however in the present figure, inner catheter 127 is shown to be longer than outer catheter 119, its distal end forming the catheter extension 127. Nose cone 125 is disposed along the distal extension of inner catheter 127 at some distance from the distal end of outer catheter 119, the distance being 2 mm to 50 mm, more typically between 5 mm and 20 mm. The balloon pocket is formed between the distal end of catheter 119 and the proximal end of nose cone 125. FIG. 28B shows an end view of outer catheter 119, disposed over inner catheter 127, with radially configured channels 123 and stand-offs 127 disposed between outer catheter 119 and inner catheter 127. Four channels are illustrated, however device 135 can have 0, 1, 2, 3, 4 or any number of channels and stand-offs, the stand-offs defining the outer edges of the channels 123 and can be formed on either the inner or outer catheter with a height limited only by the diameter of the inner and outer catheters and space there between. Although stand-offs are shown, they are not required, provided that the inner catheter OD is smaller than the outer catheter ID, thereby forming a space between the inner and outer catheters which allow fluid to flow longitudinally along device 135. Device 135 can comprise single layer inner and outer catheters or one or both can have multiple layers. In a preferred embodiment, outer catheter 19 is a three layer construction with an outer Pebax layer, a central polyimide layer including reinforcement such as a coil or braid and an inner Teflon layer. Inner catheter 127 is a single layer of low friction tubing, or tubing of similar construction to that described for the outer catheter 119. FIG. 28C shows a longitudinal view of device 135 with outer catheter 119, unexpanded balloon 131, nose cone 125 and a catheter extension of inner catheter 127. Balloon 131 is shown tucked within a pocket formed between the distal end of catheter 119 and the proximal end of nosecone 125. FIG. 28D shows a longitudinal cross section of device 135, showing balloon inflation channel 123 disposed between outer catheter 119 and inner catheter 121. In this instance, the distal end of balloon 131 is shown inserted into the proximal end of nose cone 125; however both proximal and distal balloon tails can be bonded directly to inner catheter 127, reflowed into catheter 119 or nose cone 125 or by any means, provided that the balloon tails are positioned approximately below the outer diameter of catheter 119.

Figure 29:
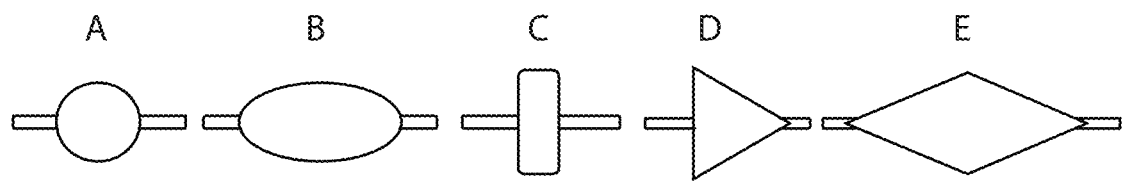
FIG. 29 gives examples of balloons used in various embodiments of the present disclosure.

Referring to FIG. 29A though FIG. 29E, examples of balloon configurations that may be used in the device of the present disclosure are shown which can be compliant or noncompliant, dilation or occlusion and can be made from any material including, but not limited to, silicone, polyurethane, polyethylene, PET (polyethylene terephthalate) and nylon.

Figure 30:
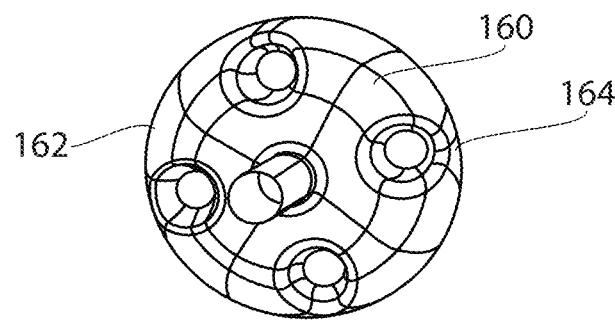
FIG. 30 shows a front view of a balloon with one-way bypass channels and valves.

Referring to FIG. 30, a surface view of balloon 160 is shown with one-way bypass channels 162 and valves 164, the balloon is described in detail in patent application No. 61/821,058.

Balloon 160 and valves 164 allow flow from the compartment proximal to the proximal surface of balloon 160 to the compartment distal to the distal surface of balloon 160 (antegrade flow) and prevents flow from the compartment distal to the distal surface of balloon 160 to the compartment proximal to the proximal surface of balloon 160 (retrograde flow). Balloon 160 can be disposed on the catheter of the present disclosure and held within a balloon pocket as illustrated in FIGS. 24-29 and enable antegrade injection of therapeutic agents from within an artery and into a target while maintaining normal (antegrade) blood flow through channels 162 of balloon 160 and prevent retrograde flow (reflux) of therapeutic agents backward over the catheter, even when pressure distal to balloon 160 is elevated above systolic and/or mean arterial pressure.

Figure 31:
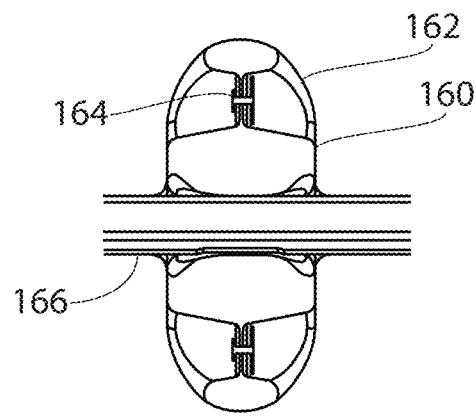
FIG. 31 shows a cross section through the balloon of FIG. 30.
Figure 32A:
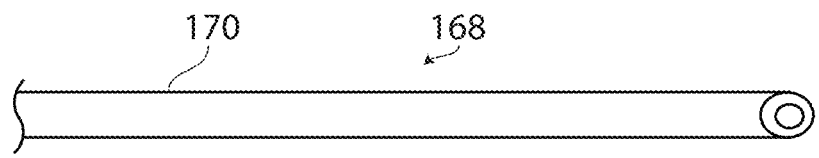
FIGS. 32A, 32B, 32C, 32D, 32E and 32F illustrate a cross sectional view of a sequential construction of an embodiment of the present disclosure including a balloon pocket and integral nose cone.
Figure 32B:
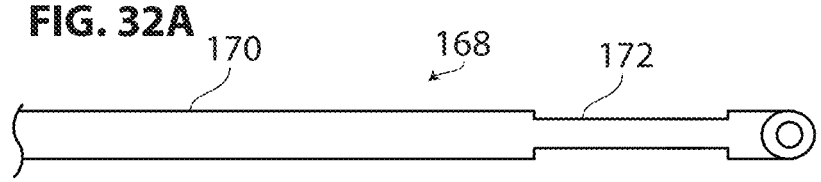
Figure 32C:
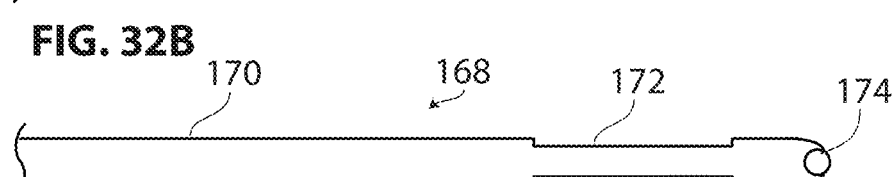
Figure 32D:
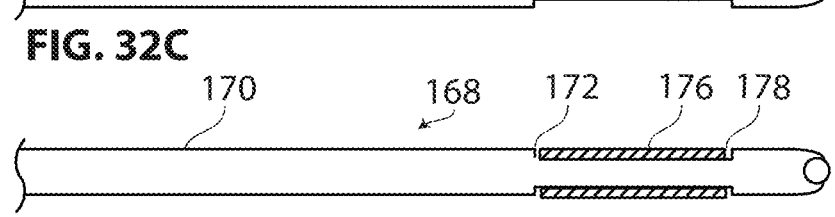
Figure 32E:
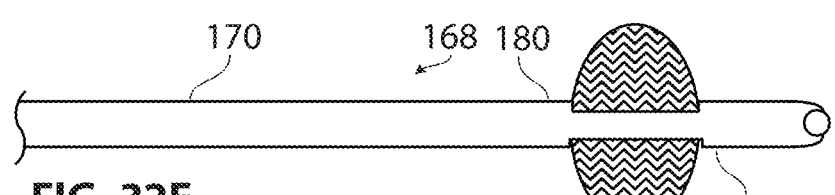
Figure 32F:
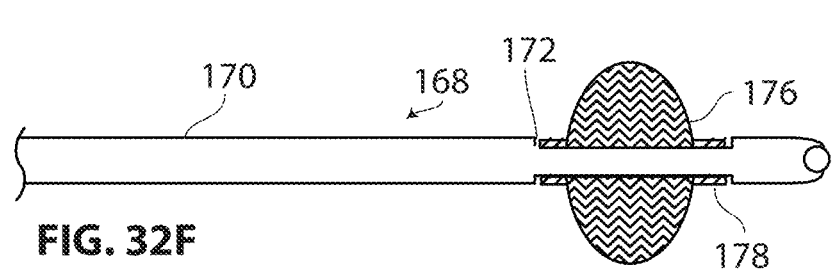

Referring to FIG. 31, a cross section of balloon 160 is shown with channels 162 and microvalves 164, positioned within channels 162.

FIG. 32 shows an example of a sequential assembly of an embodiment of the present disclosure. Referring to FIG. 32A, catheter 170 of device 168 is shown. FIG. 32B illustrates a first step in the construction of device 168 whereby a balloon pocket 172 is formed about a distal section of catheter 170 and a second step, as in FIG. 32C, whereby a rounded distal end 174 of catheter 170 is formed and a third step as in FIG. 32D whereby a balloon 176, with bonding tails 178 is disposed within pocket 172 of catheter 170 and a fourth optional step whereby catheter 170 or other material is reflowed at position 180 over balloon tails 178. FIG. 32F illustrates balloon 176 in its radially expanded configuration with balloon pocket 172 and tails 178 bonded in pocket 172 without being covered by reflow or other means.

Referring to FIG. 33, three alternate embodiments of the present disclosure are illustrated. FIG. 10A shows device 173 with catheter 181, balloon pocket 177, radially constrained balloon 178, catheter extension 171 and nose cone 182. FIG. 33B shows device 173 with radially expanded balloon 178 and bonding tails 183 bonded within balloon pocket 177. FIG. 33C illustrates device 175 with nosecone 182 and proximal bonding tail 191 reflowed into catheter 181 at position 179 and the distal balloon bonding tail 193 reflowed into or under nose cone 182 to catheter extension 171 at location 184. FIG. 33D illustrates device 179 with catheter 181, balloon 178, nose cone 182 and collar 186.

Balloon 178 has a proximal tail 191 positioned under collar 186 and distal balloon tail 193 reflowed or bonded to catheter extension 171 and under nose cone 182 or into nose cone 182. FIG. 33E shows device 179 with balloon 178 expanded from within the balloon pocket formed between collar 186 and nose cone 182.

Figure 34:
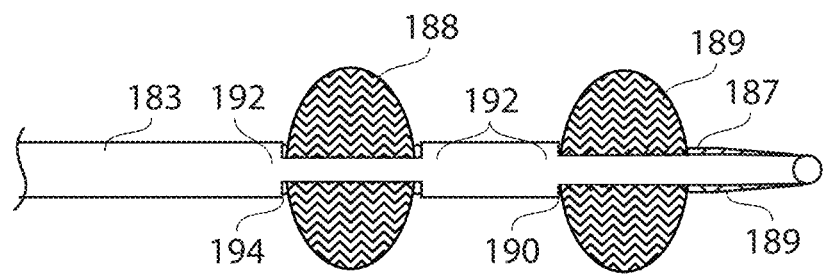
FIG. 34 illustrates an embodiment of the present disclosure with two balloons.

FIG. 34 shows yet another embodiment of the present disclosure with two balloons 188 and 189, catheter 183, balloon pockets 194 and 190, reflow areas 192 and nose cone 189. Although the example of FIG. 34 shows both balloon 188 and 189 positioned within pockets 194 and 190, only one balloon need be positioned within a pocket.

Figure 35:
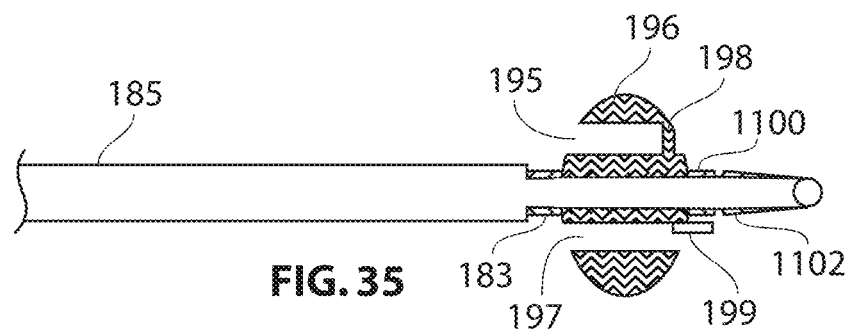
FIG. 35 illustrates an embodiment of the present disclosure including a balloon with valves.

FIG. 35 shows still another embodiment of the present disclosure with balloon 196 containing channels 195 and 197, valve 198 in the closed orientation, valve 199 in the open orientation, collar 183, nose cone 1102 and reflow area 1100. Although valve 198 is shown closed and valve 199 is shown open, they will typically act in unison and all either be simultaneously open or closed.

Figure 36:
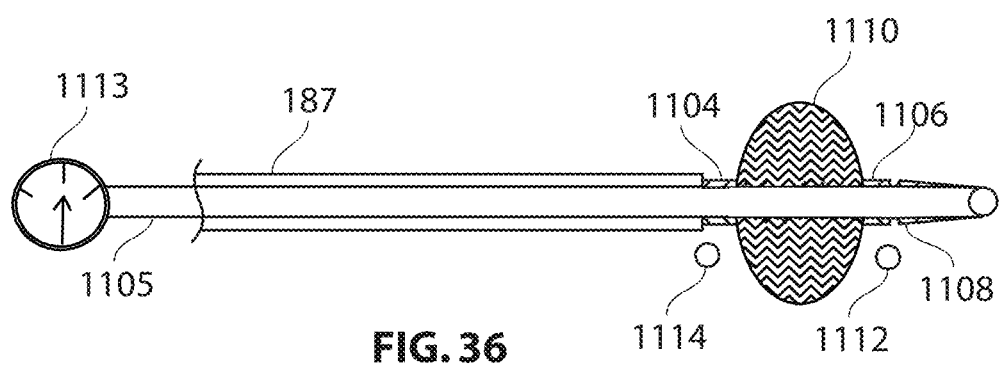
FIG. 36 illustrates an embodiment of the present disclosure with pressure sensors.
Figure 37A:
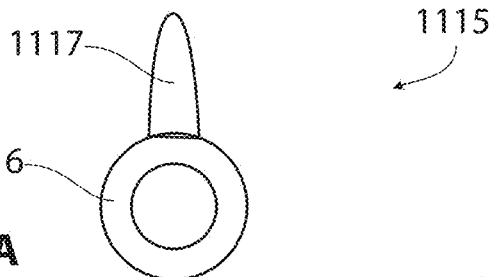
FIGS. 37A, 37B, 37C and 37D illustrate an embodiment of the present disclosure with a balloon or balloons placed on the circumference of the catheter.
Figure 37B:
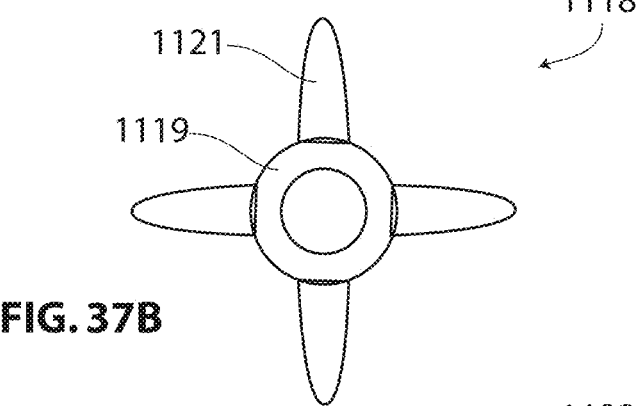
Figure 37C:
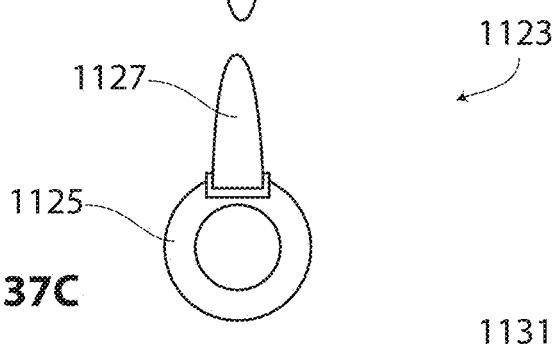
Figure 37D:
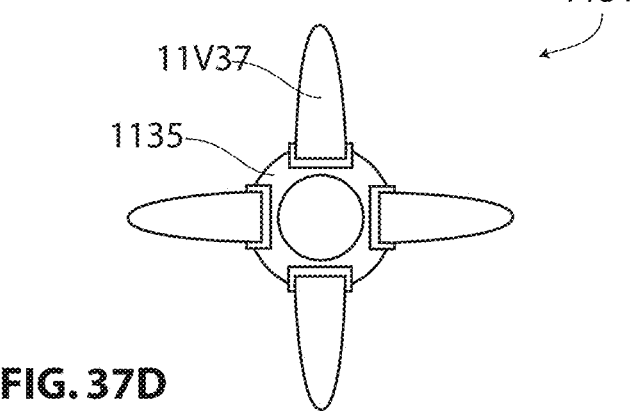

FIG. 36 shows still another embodiment of the present disclosure which includes two pressure sensors, positioned distal and proximal to balloon 1110, although a single pressure sensor positioned either distal or proximal to the balloon can be used. These pressure sensors can be used to monitor and, in conjunction with a syringe, control injection pressure either manually of by an automated means. Alternately pressure proximal or distal to the occlusion balloon can be measured through the catheter using an external pressure gauge (1113), the distal pressure being measured via the guidewire/injection lumen 1105 or any other catheter lumen or other tube. The pressure gauge can be connected to a pump, via a processor, allowing the pump to achieve a defined pressure or be programmed to a specific set of pressures, volumes and/or flow rate as a function of time.

Referring to FIG. 37, four embodiments of balloon configurations are shown. FIG. 37A, shows device 1115 with balloon 1117 and catheter 1116. Balloon 117 in a radially expanded configuration, occupies only part of the circumference of catheter 1116. FIG. 37B illustrates device 1118 with catheter 1119 and balloons 1121 whereby the four balloons 1121, in radially expanded configurations are arranged circumferentially about catheter 1119, each occupying a part of the overall outer circumference of catheter 1119. FIG. 37C illustrates device 1123, with catheter 1125 and balloon 1127 in a radially expanded configuration, whereby balloon 1127, in a radially constrained configuration is positioned within a pocket of catheter 1125 and the radially outermost part of balloons 1127 is positioned approximately at or below the outer diameter of catheter 1125. FIG. 37D illustrates device 1131 with catheter 1135 and balloons 1137 in a radially expanded configuration, whereby balloons 1137, in a radially constrained configuration are positioned within a pocket of catheter 1135 and the radially outermost part of balloons 1137 are approximately positioned at or below the outer diameter of catheter 1135.

Figure 38A:
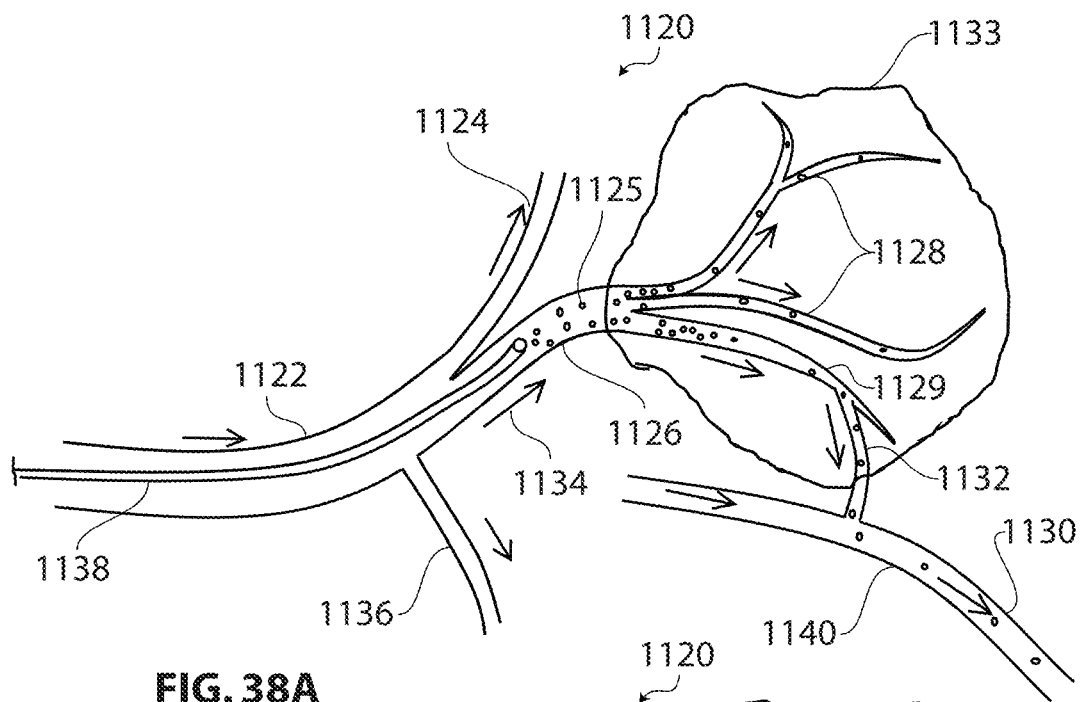
FIGS. 38A and 38B illustrate a tumor with vascular anatomy and embolization using a standard straight nose catheter.
Figure 38B:
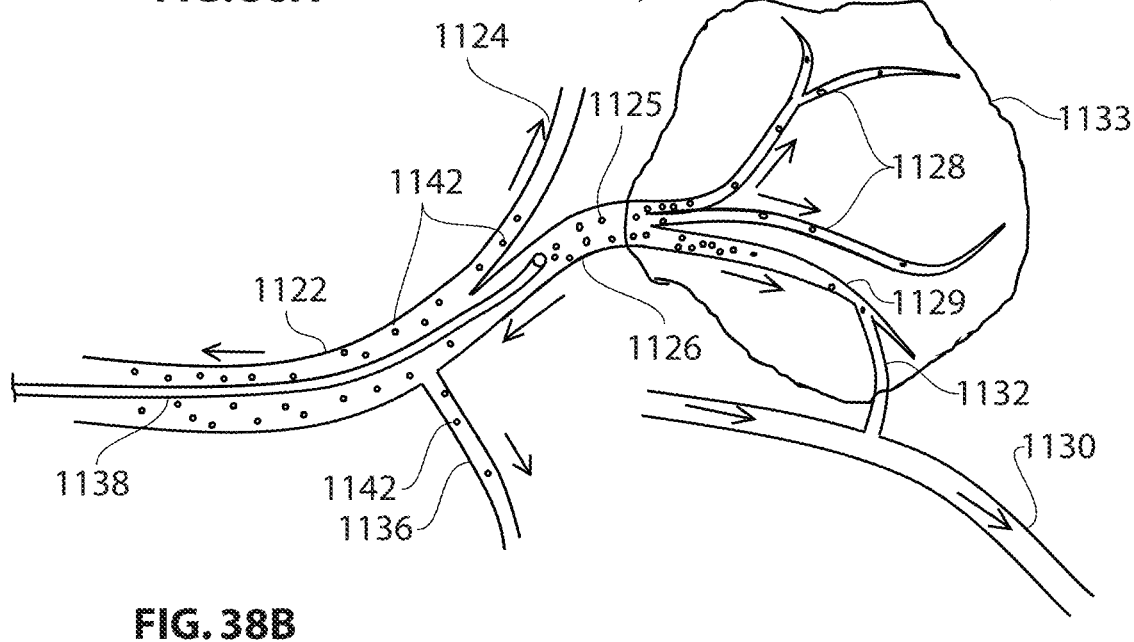

Referring to FIG. 38, an anatomical structure 1120 is shown with main artery 1122, right artery 1124, left artery 1126, right capillaries 1128, left capillary 1129, arterial side branch 1136, vein 1130, arteriovenus shunt 1132, tumor 1133, blood flow directional arrows 1134, standard straight tip catheter 1138, and embolization particles 1125. FIG. 38A illustrates the beginning of a transarterial embolization (TAE) procedure wherein the embolization particles 1125 are exiting the distal end of catheter 1138 and are carried by forward (antegrade) blood flow into tumor 1133 in a delivery method that is completely mediated by blood flow and normal blood pressure (flow mediated delivery). Capillary beds 1128 and 1129 of tumor 1133 begin to fill with embolic particles 1125 and arteriovenus shunt 1132 carries particles into vein 1130 causing antegrade reflux and non-target embolization. The flow through the arteriovenous shunt 1132 is rapid since the arterial pressure is significantly higher than venous pressure. Referring to FIG. 38B, continued injection of particles 1125 from the distal end of standard straight tip catheter 1138 results in the packing of particles and embolization of the distal ends of capillary beds 1128 and 1129. Distal capillary embolization causes the flow through arteriovenous shunt 1132 to stop and pressure to build in left artery 1126. As embolization progresses, the back pressure in artery 1126 continues to rise until embolic particles reflux in the retrograde direction 1142 causing non-target embolization of the right artery 1124, arterial side branch 1136 and main artery 1122. This situation can cause non-target embolization, loss of an unknown amount of particles, delivery of an unknown and irreproducible dose and non-optimal distribution of embolic particles in the tumor vasculature. In this instance, both antegrade and retrograded reflux can occur.

Figure 39A:
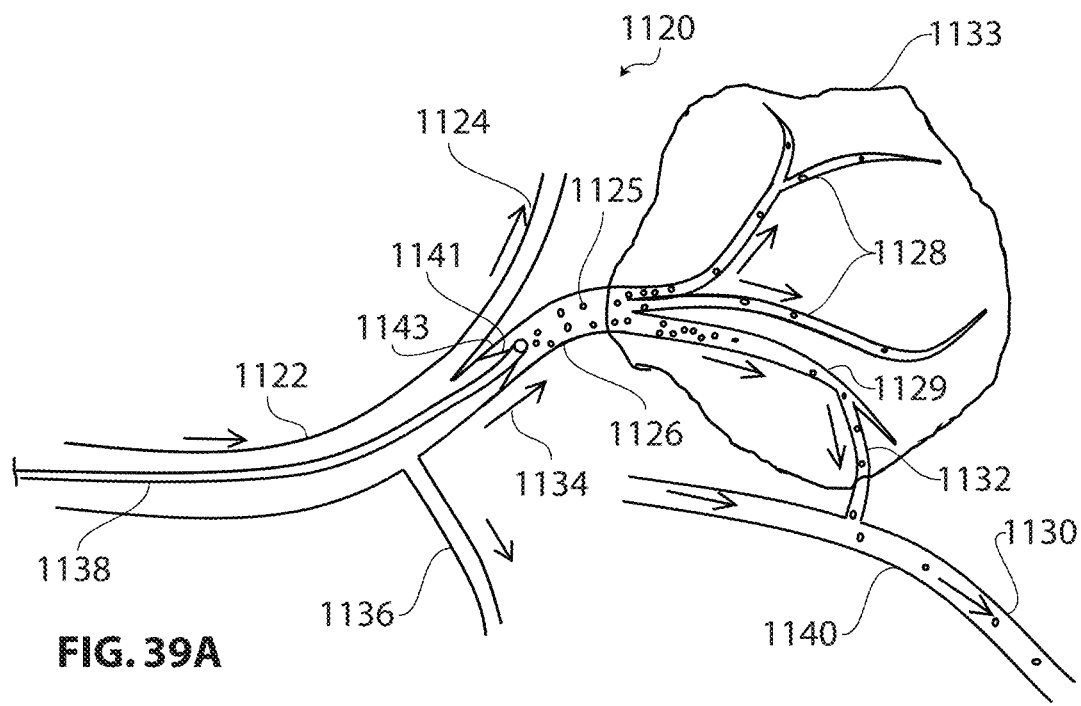
FIGS. 39A and 39B illustrate a tumor with vascular anatomy and embolization using a balloon including channels and valves.
Figure 39B:
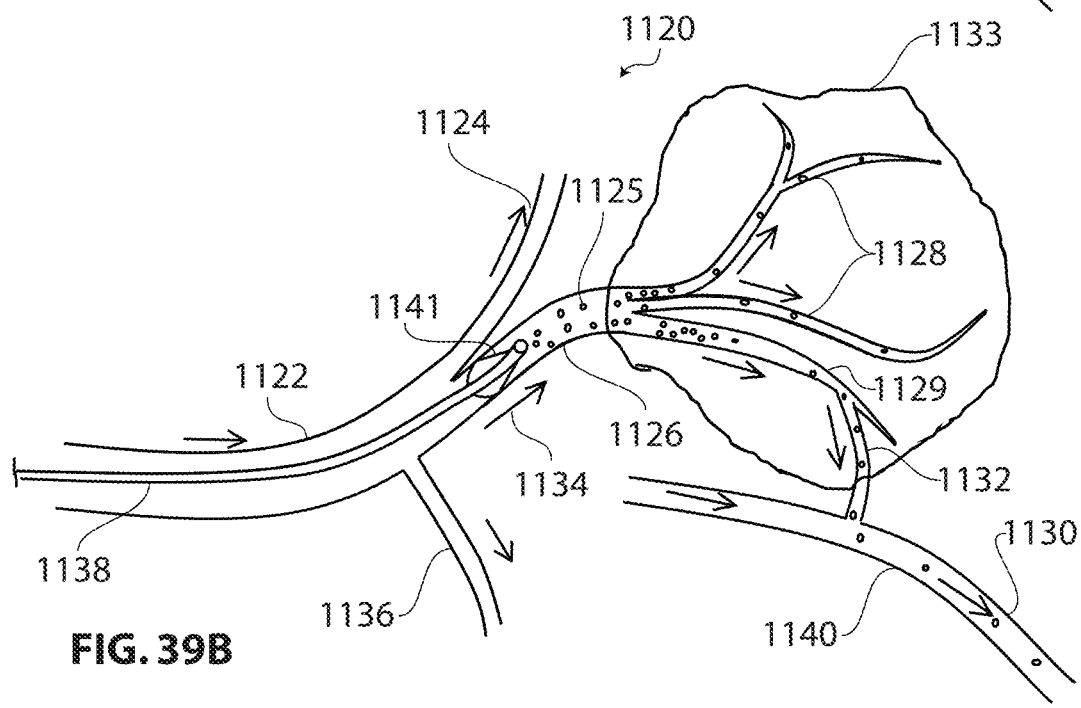
Figure 40A:
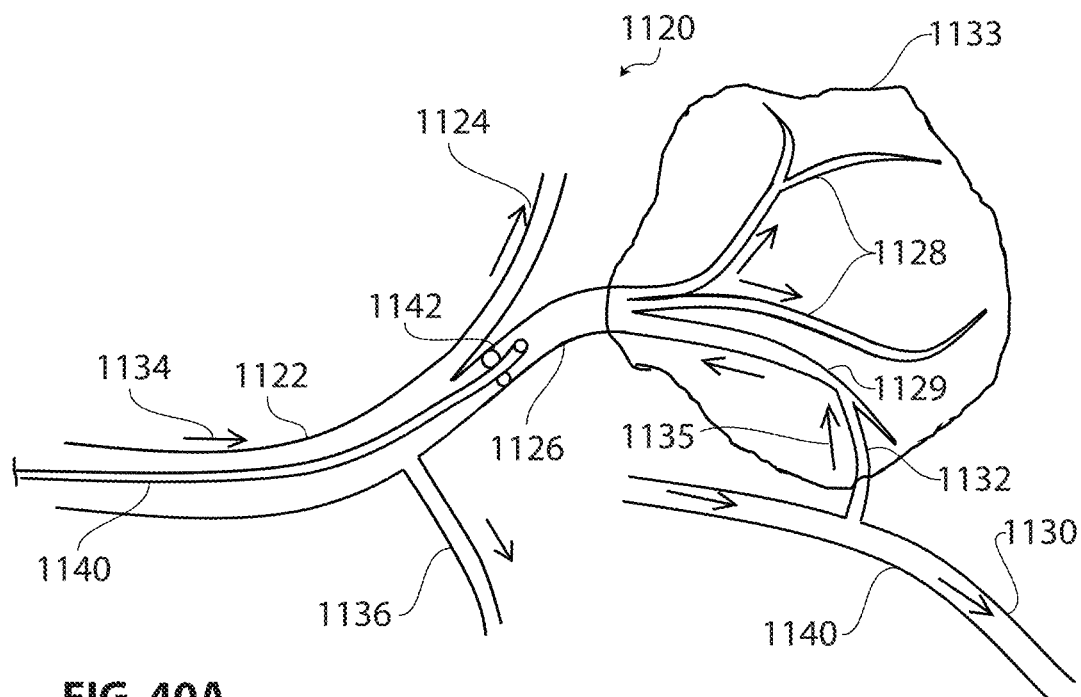
FIGS. 40A, 40B, 40C and 40D illustrate a tumor with vascular anatomy and embolization using an occlusion balloon.
Figure 40B:
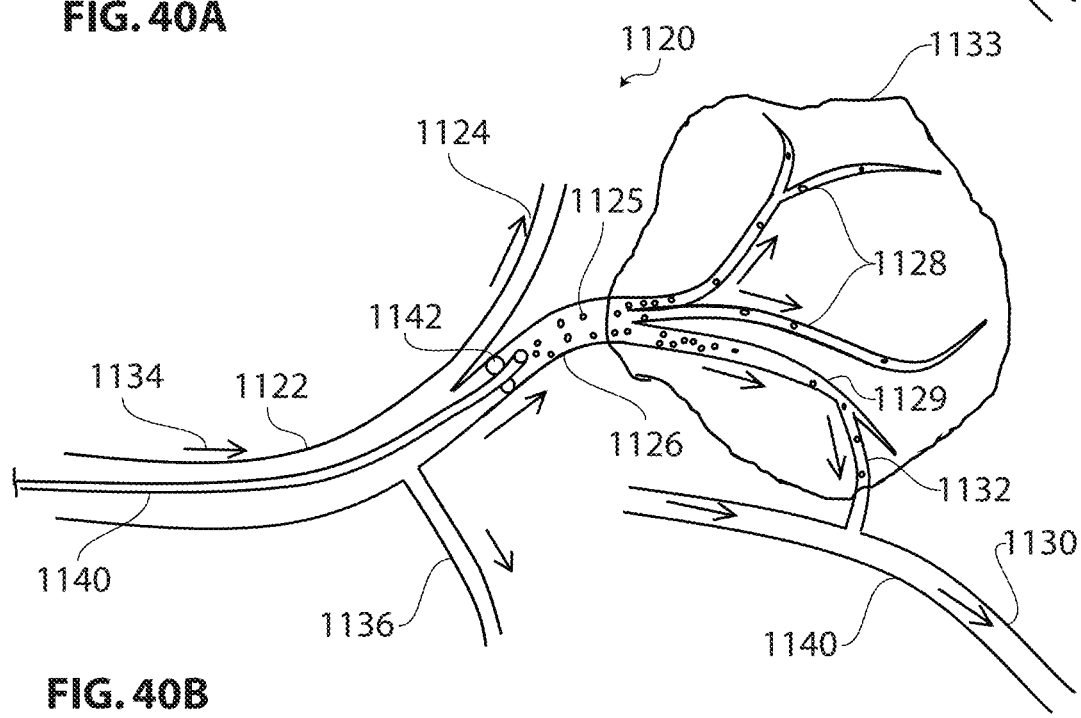
Figure 40C:
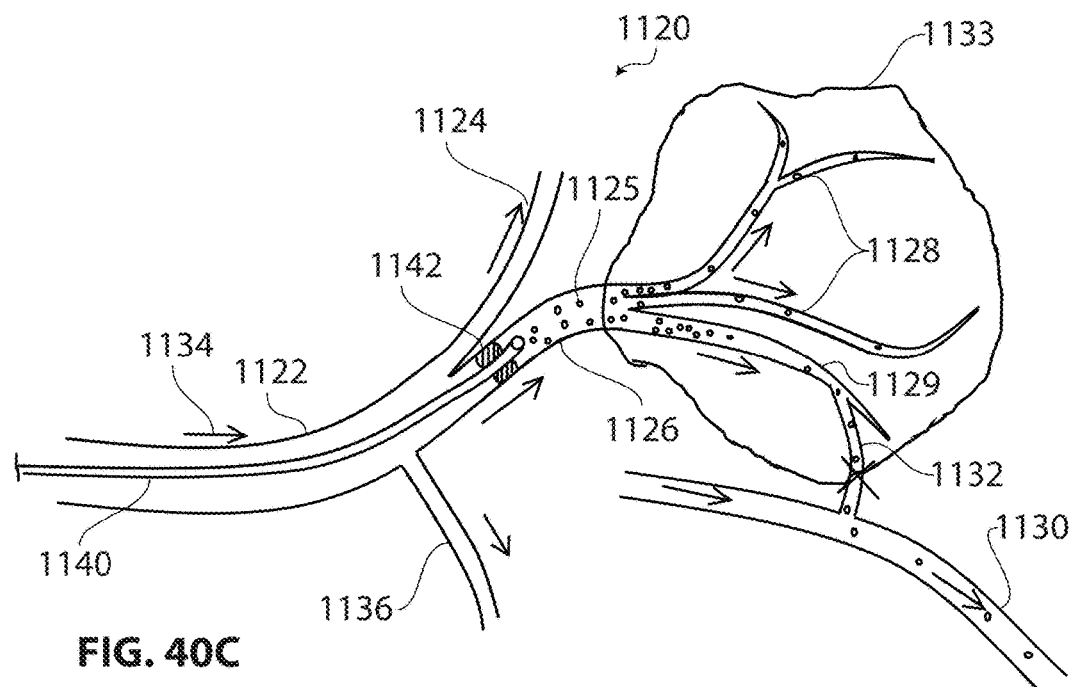
Figure 40D:
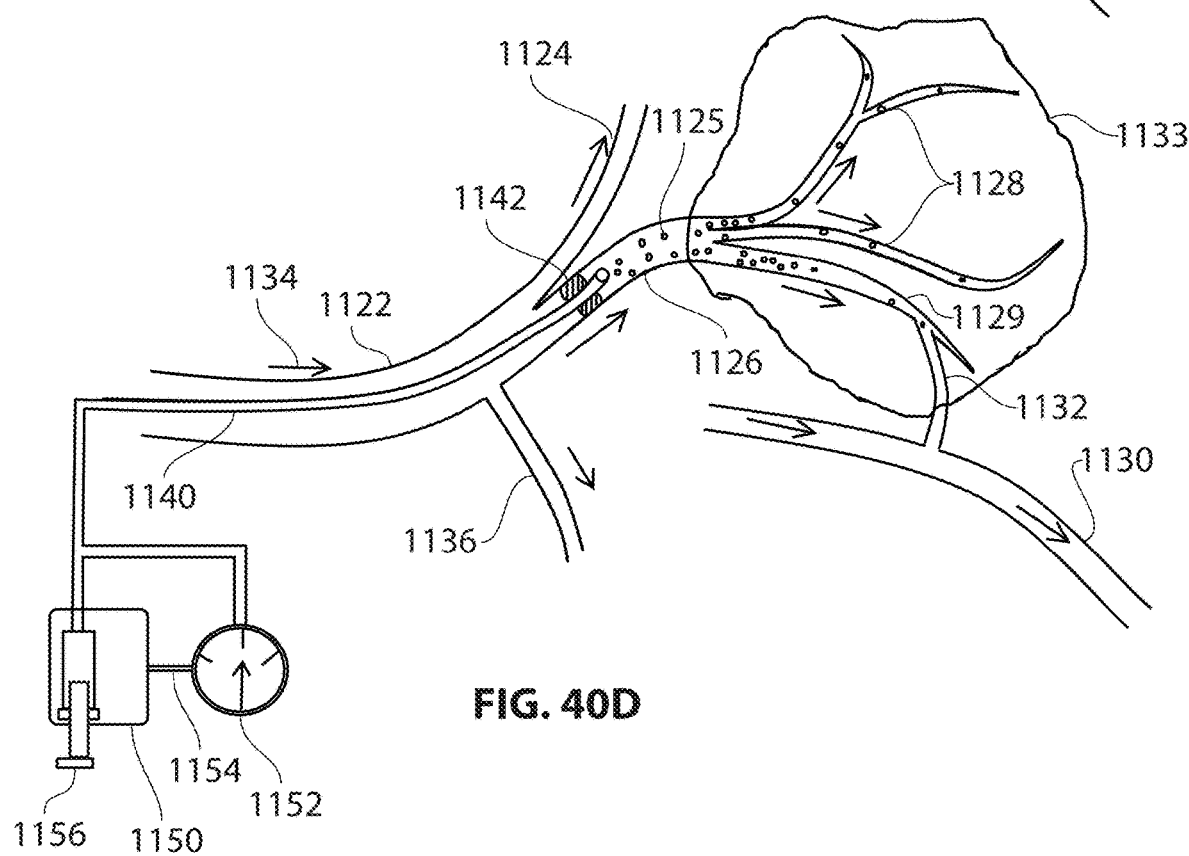

Referring to FIG. 39, anatomical structure 1120 is shown as in FIG. 38. In this instance, a balloon 1141, with channels 1143 and one-way valves (FIGS. 30 and 31) is positioned about the distal end of catheter 1139. Balloon 1141, so constructed, will allow only antegrade (normal) flow and prohibit retrograde flow. Referring to FIG. 39A, balloon 1141 is shown in its radially expanded configuration and blood is flowing through balloon channels 1143 as indicated by blood flow arrow 1134 and into the vasculature of tumor 1133. Embolic particles 1125 are released from the distal end of catheter 1139 and carried forward by blood flow into capillaries 1128 and 1129. Capillary beds 1128 and 1129 of tumor 1133 begin to fill with embolic particles 1125 and arteriovenous shunt 1132 carries particles into vein 1130 causing antegrade reflux and non-target embolization. The flow through the arteriovenous shunt 1132 is rapid since the arterial pressure is significantly higher than venous pressure. Referring to FIG. 39B, continued injection of particles 1125 from the distal end of balloon catheter 1139 results in the packing of particles and embolization of the distal ends of capillary beds 1128 and 1129. Distal capillary embolization causes the flow through arteriovenous shunt 1132 to stop and pressure to build in left artery 1126. As embolization progresses, the pressure in artery 1126 continues to rise, however the valves of balloon 1141 close and prohibit retrograde reflux. In this instance, continued injection will increase the packing pressure of particles 1125 and can increase packing density and increase flow into distal locations in the margins of a tumor or other structure thereby improving particle distribution throughout the target vasculature. As part of the present method, pressure distal to the balloon can be regulated between systolic and/or mean arterial pressure and any pressure above that pressure, provided that it is within a range that is safe for the patient. By way of example, injection pressure can be low at the onset of the embolization procedure and increased at some point thereafter to a pressure greater than systolic and/or mean arterial pressure. Such a point may, for example, be chosen to coincide with the stoppage of flow through arteriovenous shunt 1132. This method may improve particle distribution and packing. Alternately, the injection pressure through catheter 1139 can be high at the onset, thereby forcing particles rapidly into the distal section of capillaries 1128 and 1129 and hasten embolization of arteriovenous shunt 1132, thereby reducing antegrade reflux. Alternately, according to this method, a low to high pressure gradient or a high to low pressure gradient can be used. The aim for the use of a pressure mediated delivery of particles is to optimize for a low level of antegrade reflux, substantial elimination of retrograde reflux, high particle distribution and high particle density. A pressure sensor as in FIG. 36 can be used on the proximal and/or distal side of balloon 1142 to monitor pressure and enable a selection of a procedural end point based on a definitive pressure reading.

Referring to FIG. 40, anatomical structure 1120 is shown as in FIG. 38. In this instance, an occlusion balloon 1142 is positioned about the distal end of catheter 1140. Referring to FIG. 40A, balloon 1142 of catheter 1140 is shown in a radially expanded configuration. Since expanded balloon 1142 completely occludes artery 1126, all arteries and capillaries distal to the balloon are isolated from the main artery 1122, right artery 1124 and side branch artery 1136 thereby causing blood pressure distal to the balloon to drop from approximately normal arterial pressure of about 80 mmHg to a pressure in the range of 0-50 mmHg. When this happens, blood flow through the arteriovenous shunt 1132 can reverse as shown by blood flow arrow 1135, or the antegrade flow slowed or stopped. Referring to FIG. 40B, initial injection of particles 1125 will be against a pressure, with a minimal antegrade flow or into a flow stasis. Retrograde pressure flow against the particle injection can result from the flow of venous blood from vein 1130, through arteriovenus shunt 1135 and into the arterial capillary 1129 or from arteriovenous capillary beds associated with capillaries 1128. As particles 1125 are injected, they fill capillaries 1128 and 1129; however, particles cannot easily flow through arteriovenous shunt 1132 because of the reversal or slowing of flow and pressure. Continued injection can result in embolization of the distal portion of capillary 1129 and blockage of arteriovenous shunt 1132 with concomitant reduction or elimination of antegrade reflux. Increasing injection pressure through catheter 1140 following embolization of arteriovenous shunt 1132, can result in a high levels of particle density and distribution. Alternately, according to this method, a gradient can be used. The profile of the pressure gradient can be any function of time and pressure including, but not limited to, a linear or step function from low to high, high to low, alternating high to low and low to high or any other function and can be administered manually, in a semi-automated manner or using a programmable delivery means. Alternately according to this method, a pressure sensor as in FIG. 36 can be used on the proximal and/or distal side of balloon 1142 to monitor pressure and select a procedural end point based on a definitive pressure reading. Referring now to FIG. 40D, the injection through catheter 1140 into tumor 1133 can be accomplished using an automated pump/pressure monitor system whereby the pressure distal to occlusion balloon 1142 is measured on gauge 1152, the pressure reading transferred through connection 1154 to pump 1150 which controls the injection of anti-tumor agents from syringe 1156. Pump 1150 can be controlled manually or programmed to any function of flow rate, time and/or pressure. The endpoint can be selected at any desirable pressure.

The aim of the present method is to eliminate retrograde reflux, reduce or eliminate antegrade reflux, control the particle density and distribution, deliver an optimal dose, enable a defined pressure endpoint, improve efficacy and reduce toxicity.

Referring to FIG. 41A, a longitudinal cross section of a catheter is shown with proximal and distal ends, catheter body 204, distal tip 203 and proximally disposed hub 206. Catheter body 204 has two lumens that are in fluid communication with hub 206, a first lumen extending from port 208 of hub 6 to the distal tip 203 of catheter 204 whereby fluid can be injected from the proximal hub 206 and exit at the distal tip 203 of catheter 204 and a second lumen extending from port 210 of hub 206 to an intermediate location at some distance from the distal tip 203 of catheter 204, the second lumen adapted to communicate with a balloon for inflation and deflation.

Referring to FIG. 41B, a longitudinal cross section of a first embodiment of the present disclosure is shown with proximal and distal ends, catheter body 204, distal tip 203, and two layered occlusion balloon 214 with channels 205 and valves 207 and proximally located hub 206. Although balloon 214 is shown with two channels, each with a valve, balloon 214 can have 1, 2, 3, 4 or any number of channels and any number of valves or be without valves. In this instance, the valve configuration allows fluid to flow from the proximal side of balloon 214 to the distal side of balloon 214 and to restrict flow from the distal side of balloon 214 to the proximal side of balloon 214; however, the opposite valve orientation and flow direction is also part of the present disclosure. Catheter body 204 can have a diameter of between 1 Fr and 10 Fr, more typically 2 Fr to 5 Fr and a length of 10 cm to 250 cm, more typically 50 cm to 150 cm. Two layered occlusion balloon 214 can be from 1 mm to 30 mm in diameter, more typically 2 mm to 10 mm in diameter, in its radially expanded configuration.

Referring to FIG. 41C, an alternate embodiment of the device of the present disclosure is shown, having catheter body 218, distal tip 209, hub 206 and umbrella shaped occlusion structure 220. When in its radially expanded configuration, the occlusion structure will completely occlude the flow of the vessel. The umbrella shaped occlusion structure 220 is positioned at some distance from the distal end of catheter 216 and forms an umbrella shaped structure disposed circumferentially about catheter 216 with its outer diameter in contact with the vessel. Umbrella shaped occlusion structure 220 can be from 1 mm to 30 mm in diameter more typically 2 mm to 10 mm in diameter when in its radially expanded configuration and a longitudinal thickness of 0.25 mm to 10 mm, more typically 0.5 mm to 2 mm. Umbrella shaped occlusion structure 220 is shown with its closed end attached to the catheter distal to the open end of the V shape; however, it can be positioned in the opposite orientation or it can be positioned at a 90 degree angle with respect to catheter body 18.

Referring to FIG. 41D, device 222 of the present disclosure is shown having catheter 218, distal tip 209, hub 206, and a unidirectional umbrella occlusion structure 224 with channels 230 and valves 228. Occlusion structure 224 will allow proximal to distal flow and prevent distal to proximal flow.

Referring to FIG. 41E, device 232 is shown with catheter body 234, catheter distal extensions 235 and distal tip 211. Catheter extension 235 can have a diameter of 0.5 Fr to 5 Fr, more typically of 1 Fr to 3 Fr and can be absent or can be of any length, typically 2 mm to 30 mm, more typically from 5 mm to 20 mm.

Referring to FIG. 41F, a preferred embodiment of the present disclosure is shown with catheter body 237, catheter extension 235, distal tip 211, nose-piece 241 and two layered occlusion balloon 243 in its radially expanded configuration. In this instance, two layered occlusion balloon 243 is disposed within a pocket formed on distal catheter extension 235 and between the distal end of catheter body 237 and the proximal end of nose-piece 241. The nose piece can be a tapered nose cone, a distally rounded piece of tubing or catheter, a blunt tube or any structure with a diameter equal to less than the catheter body. When in the radially constrained configuration, the outer diameter of the two layered occlusion balloon 243 has an outside diameter that is about equal to the outer diameter of the catheter body 237.

Referring to FIG. 41G, yet another embodiment of device 245 of the present disclosure is shown, having catheter body 247, distal tip 234, nose-piece 241, proximal hub 206 and unidirectional umbrella shaped occlusion structure 224 with channels 230 and valves 228. In this instance, unidirectional umbrella occlusion structure 224 with channels 230 and valves 228 is disposed within a pocket formed on distal catheter extension 234 and between the distal end of catheter body 247 and the proximal end of nose-piece 241. The nose piece 241 can be a tapered nose cone, a radiopaque marker band, a distally rounded piece of tubing or catheter, a blunt tube or any structure of about equal diameter to the catheter body. When in the radially constrained configuration, the unidirectional umbrella shaped occlusion structure 224 has an outside diameter that is about equal to the outer diameter of the catheter body 247.

Referring to FIG. 42, four views of a preferred embodiment of the unidirectional occlusion structure of present disclosure is shown. FIG. 42A illustrates a two layered unidirectional occlusion structure 236 in its radially expanded configuration (also seen in FIGS. 41B and 41F), having a proximal end 238, a distal end 240, balloon 242, balloon sheath 244, channel 246, valve structure 250, outer balloon sheath tail 254, balloon tail 256, flow direction arrow 252 and flow exit 248. When occlusion structure 236 is disposed on a catheter as in FIG. 41F, fluid flows in the proximal to distal direction (antegrade) as indicated by arrow 252 through channel 246 and valve 250 and exits out the distal flow exit 248. The antegrade fluid pressure on the inner surface of balloon sheath 244 at the distal end of channel 246, causes distally directed displacement or deflection of the inner surface of balloon sheath 244 at valve 250, thus allowing fluid to pass through flow exit 248. When flow is reversed, fluid pressure on the outer distal surface of balloon sheath 244 at valve 250 causes the balloon sheath 244 to press against the distal surface of balloon 242, closing valve 250 and preventing retrograde flow. Placing the unidirectional occlusion structure 236 in the opposite direction on the catheter will result in distal to proximal flow and prohibit proximal to distal flow. Although the occlusion structure of FIG. 42A is shown with two layers including an inner balloon and an outer sheath, it is understood that the sheath need not be present and a balloon with channels from the proximal surface to the distal surface is considered part of the present disclosure. Balloon 242, including channels 246 can be formed by molding, extruding, vacuum forming or otherwise shaping a material to include the desired number and configuration of channels. Alternately, a standard balloon, including but not limited to, round or oval, can be modified to achieve proximal to distal channels. One method to modify a balloon is by forming longitudinal pleats circumferentially oriented, thereby forming V shaped channels that extend from the proximal surface of the balloon to the distal surface of the balloon. Placing a sheath over such a modified balloon in the same manner as described above would give the same result as the balloon shown in FIGS. 42A through 42D.

Figure 42A:
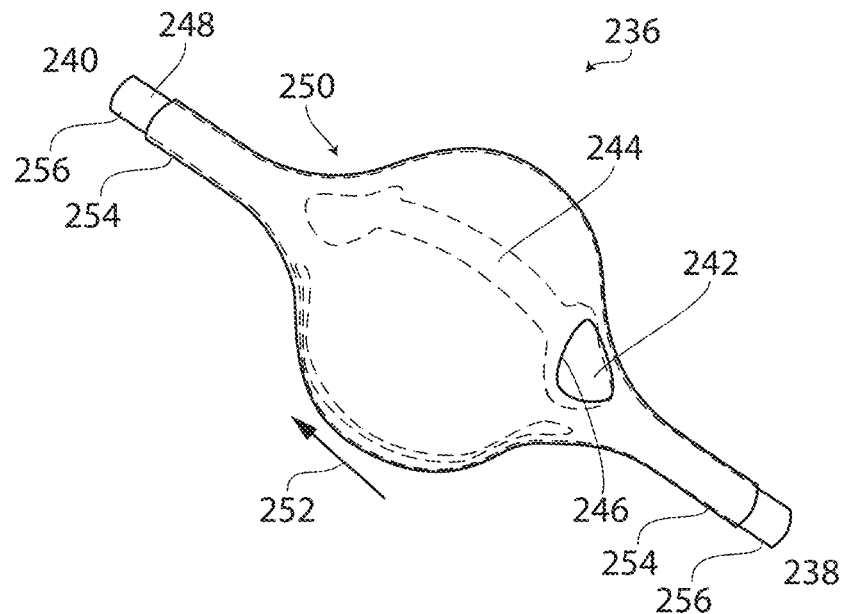
FIGS. 42A, 42B, 42C and 42D illustrate a two layer occlusion structure with unidirectional flow.
Figure 42B:
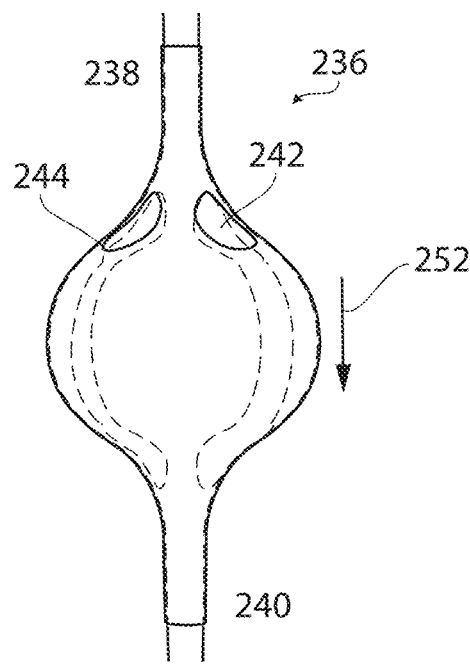

Referring to FIG. 42B, a side view of the unidirectional occlusion structure 236 of this disclosure is shown with proximal end 238 distal end 240, balloon 242, balloon sheath 244 and flow direction arrow 252.

Figure 42C:
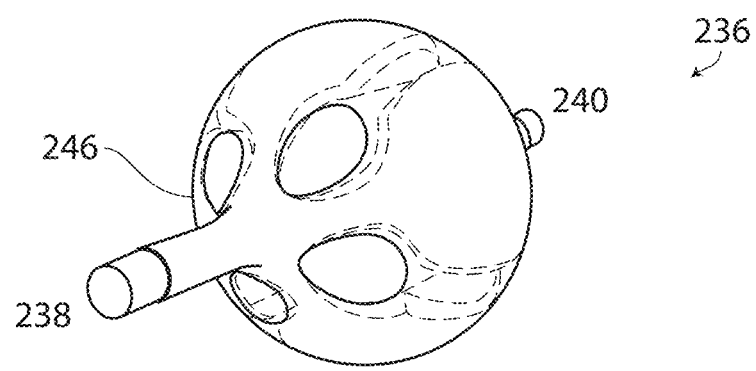

Referring to FIG. 42C, a proximal view of the unidirectional occlusion structure 236 is shown with proximal end 238, distal end 240 and channels 246.

Figure 42D:
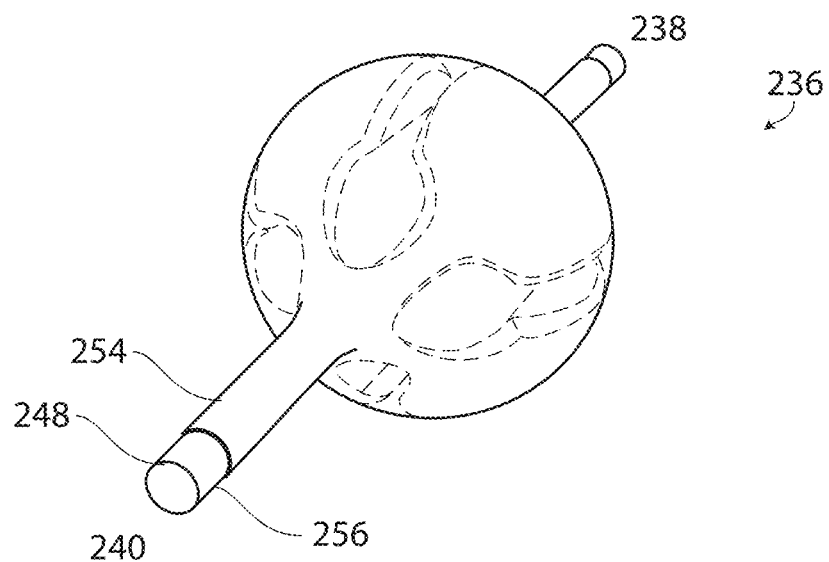

Referring to FIG. 42D, a distal surface view of the unidirectional occlusion structure 236 is shown with proximal end 238, distal end 240 and flow exit 248. Flow exit 248 is formed as a space between balloon tail 256 and balloon sheath 254. It is also possible to terminate balloon sheath 244 immediately below channels 246 forming a valve 250 that does not include balloon sheath tail 254.

Figure 43:
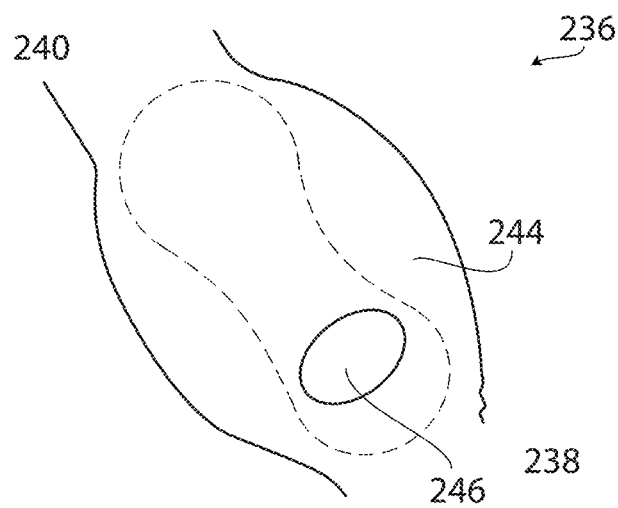
FIG. 43 illustrates a prototype of the occlusion structure of FIG. 42.

Referring to FIG. 43, an illustration of a prototype of the unidirectional occlusion structure 236 is shown in its radially expanded configuration with proximal end 238, distal end 240, balloon sheath 244, balloon 242 (positioned inside balloon sheath 244), and channel 246. This device was tested and will withstand at least 220 mmHg against its distal surface without retrograde flow.

Figure 44A:
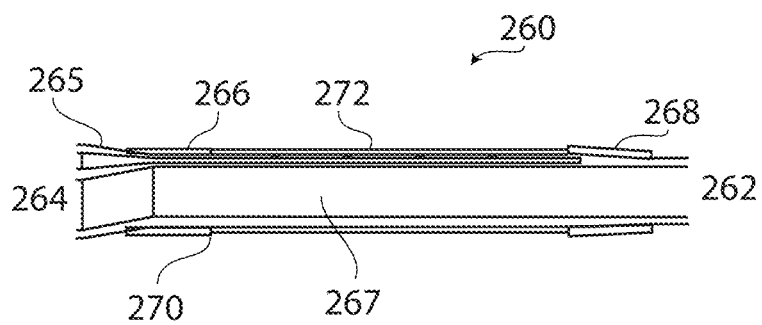
FIGS. 44A and 44B illustrate an embodiment of the present disclosure including a catheter with a pocket.

Referring to FIG. 44, device 60 illustrates the unidirectional occlusion structure 272 in a radially constrained configuration adapted to the distal extension 267 of a catheter 265 with distal end 262, proximal end 264, proximal collar 266, distal collar 268 (formed into a nose cone) and device pocket 270. Proximal collar 266 and distal collar 268 can comprise a metal, such as a radiopaque marker band, heat shrink tubing or any plastic material such as polyurethane, polyethylene, polystyrene, acetal, PTFE, nylon or the like, and can be 1 mm to 20 mm in length, more typically from 2 mm to 10 mm in length. In this instance, circumferentially oriented occlusion structure 272 is held within pocket 270 of catheter 265, with an outer diameter approximately equal to the outer diameter of catheter 265.

Figure 44B:
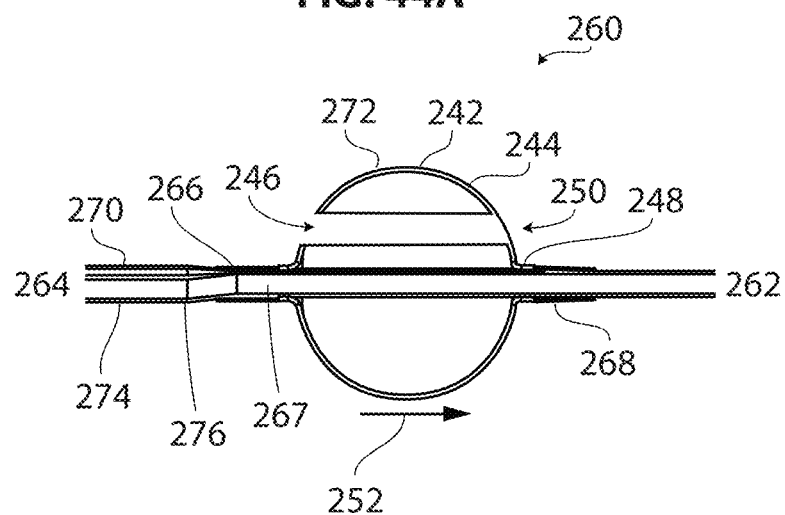

Referring to FIG. 44B, device 260 is shown with unidirectional occlusion structure 272 in its radially expanded configuration with proximal end 264, distal end 262, balloon 242, balloon sheath 244, valve 250, flow exit 248, channel 246, flow arrow 252, proximal collar 266, distal collar 268, catheter 274, balloon fill lumen 270 and guidewire/injection lumen 276. In this instance, there is no distal balloon sheath tail, the balloon sheath terminating on the balloon surface just below channel 246 and above the perimeter of catheter extension 267, thereby positioning the flow exit between the termination of the balloon sheath and the catheter.

Referring to FIG. 45A, device 280 is shown with catheter 282 and an umbrella shaped structure occlusion structure 2284 in its radially expanded configuration, whereby the umbrella shaped occlusion structure 284 is oriented circumferentially about catheter 282 such that its outer circumference is 360 degrees about catheter 282. When device 280 is placed in an artery or vein and umbrella shaped occlusion structure 284 is placed in its radially expanded configuration, the outer perimeter of occlusion device 284 will be at least in contact with the interior of the vessel wall and substantially occlude flow. FIG. 45A shows occlusion structure 284 in forward V orientation and FIG. 45B shows device 282 with the umbrella shaped occlusion device 288 in a reverse V configuration. The occlusion structure of the present disclosure can also have a 90 degree orientation with respect to the catheter when in its radially expanded configuration.

Referring to FIG. 46A, device 290 is shown with proximal end 292, distal end 294, catheter 296, two-way occlusion structure 299 in its radially expanded configuration, frame 298 and channels 2100, whereby fluid can flow from proximal to distal or distal to proximal through channels 2100. Although two channels are shown, two-way occlusion structure 298 can have 1, 2, 3 or any number of channels.

Referring to FIG. 46B, device 2102 is shown with proximal end 2104, distal end 2106, catheter 2108, and unidirectional umbrella shaped occlusion device 2110 comprising, frame 2111, channels 2112 and radial valve 2114, whereby fluid will flow from proximal to distal (antegrade) only, retrograde flow being prohibited by radial valve 2114. Although device 2102 will allow only antegrade flow, if desired, device 2110 of apparatus 2102 can be configured to allow only retrograde flow and/or have a forward V configuration as shown, or, if desired, a reverse V configuration or an orientation 90 degrees with respect to catheter 2108.

The frames 298 and 2111 of occlusion structure 2110 can be made of metal, such as shape memory metals nitinol or elgiloy, or plastic such as polyethylene, polyurethane, polystyrene, PTFE, acetal and nylon or elastic materials such as silicone or fabrics such as cotton and rayon and can include a mesh, a wire frame, a diaphragm and can be pleated or otherwise folded or can be any other convenient structure or material provided that it is of sufficient strength and porosity to occlude elevated vascular pressures and capable of integrating channels and valves. Valve 114 can be made from flexible or rigid plastics including polypropylene and polyurethane, elastomeric materials such as silicone and can have a configuration including a flap, sock, cone, duck bill and diaphragm or the like with a thickness of 1 mil to 50 mil, more typically 2 mil to 10 mil.

Referring to FIG. 47A, a distal surface view of a unidirectional occlusion structure 2120 of the present disclosure is illustrated with the catheter 2122 (extending forward), device frame 2124, radial valve 2125 and channels 2126 disposed under radial valve 2125. As shown, radial valve 2125 extends radially outward from catheter 290 and covers all four valves. Four channels are shown in this example; however, any number of channels can be used. This configuration allows flow from the proximal surface to the distal surface of unidirectional umbrella shaped occlusion structure 2120; however, the reverse flow is also possible.

FIG. 47B illustrates another embodiment of the present disclosure comprising unidirectional umbrella shaped occlusion structure 2128 with catheter 2130 (extending forward), device frame 2132, valves 2136 and channels 2134 disposed under valves 2136. In this instance, each channel has a separate valve and although four channels and valves are shown, the device of this disclosure can have any number of channels and valves limited only by the size of the valve and channel and the area of the frames 2124 and 2132. This unidirectional configuration allows flow from the proximal surface to the distal surface of umbrella shaped occlusion structure 2128; however, the opposite flow can be easily achieved by changing the flow direction of the valves or rotating the unidirectional occlusion device 180 degrees on catheters 2122 and 2130.

FIGS. 48A and 48B illustrate a prototype micro-valve 2140 configured from 5 mil polyurethane material. This device was tested and will restrain a fluid pressure of at least 220 mmHg applied against its distal surface.

Figure 49A:
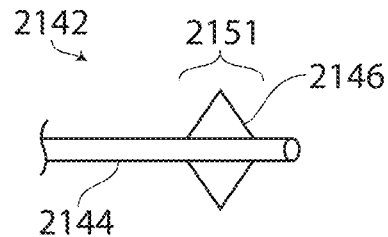
FIGS. 49A and 49B show an alternate embodiment of an occlusion structure.

Referring to FIG. 49A, device 2142 is shown with triangular shaped occlusion structure 2145 in its radially expanded configuration and adapted to catheter 2144 whereby the occlusion structure 2145 has frame 2146 oriented circumferentially about catheter 2144 such that its outer circumference comprises 360 degrees. When device 2142 is placed in an artery or vein, frame 2146 is placed in its radially expanded configuration and the outer perimeter of device frame 2146 will be at least in contact with the interior of the vessel wall and at least substantially occlude flow.

Figure 49B:
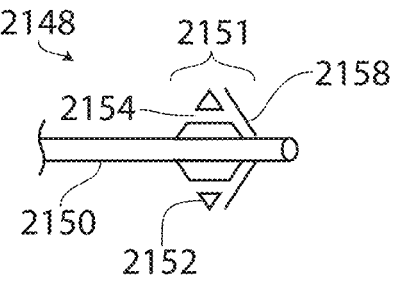

Referring to FIG. 49B, device 2148 is shown with catheter 2150 and a unidirectional triangular shaped occlusion structure 2151 comprising frame 2152, channels 2154 and radial valve 2158. Although reference has been made to a unidirectional occlusion valve with an umbrella shape or a triangular shape, it is understood that any shape including, but not limited to, rectangular, oval, conical, and round can be used. Yet another construction of a unidirectional occlusion structure is a dilation or occlusion balloon or any other medical balloon disposed with channels and valves, the valves extending from a proximal surface to a distal surface.

Figure 50A:
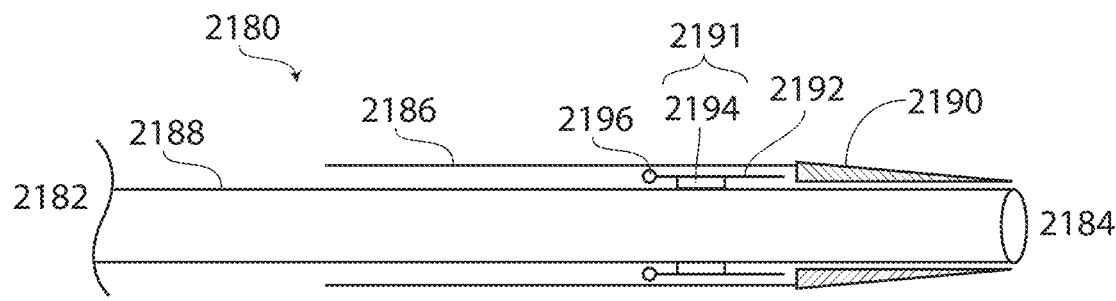
FIGS. 50A, 50B and 50C illustrate a method of operation of one embodiment of a unidirectional occlusion structure of the present disclosure.
Figure 50B:
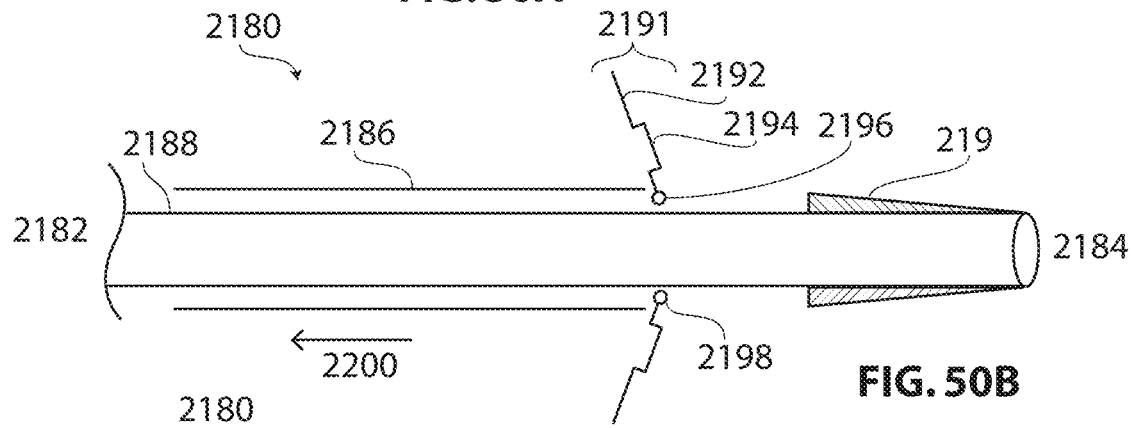
Figure 50C:
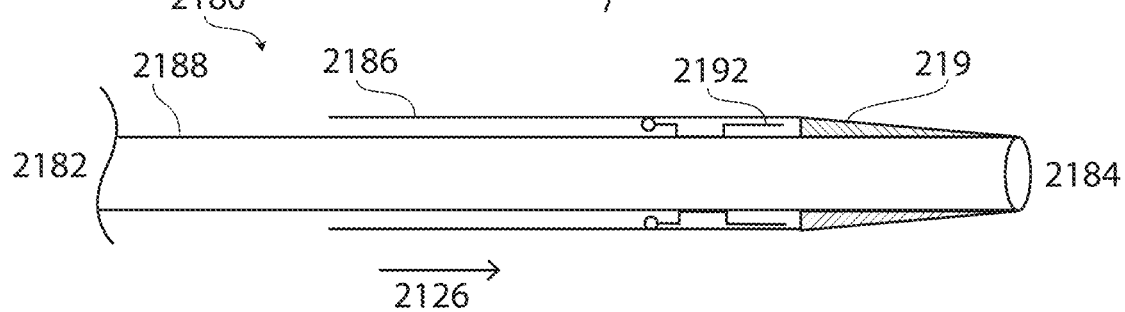

Referring now to FIG. 50A to 50C, a method of deploying an occlusion structure 2191 from a radially constrained configuration to a radially expanded configuration and then returning it to the constrained configuration is shown. FIG. 50A shows a longitudinal cross section of device 2180 with a proximal end 2182, a distal end 2184, outer catheter 2186, inner catheter 2188, nose cone 2190 and radially constrained unidirectional occlusion structure 2191 with frame 2192, valve 2194, and frame attachment point 2196. Unidirectional occlusion structure 2191 is attached to inner catheter 2188 at attachment point 2196 whereby occlusion device 2191 is preloaded with a force which encourages its distal end to pivot proximally outward at attachment point 2196. In this instance, the outer catheter 2186 constrains occlusion structure 2191 against the preloaded force. Device 2180 is first positioned in the vasculature at or in the vicinity of a target structure.

Referring to FIG. 50B, outer catheter 2186 is retracted proximally as shown by arrow 2200 while the inner catheter 2188 is held stationary, thereby removing the constraint on occlusion structure 2191, allowing it to pivot outward and in a proximal direction at attachment point 2196 and into its radially expanded configuration. Frame 2192 can be made from a memory metal such as nitinol or elgiloy and preformed at attachment point 2196 to the radially expanded configuration thereby pre-loading an outward force on occlusion structure 2191 as it is moved to its radially constrained configuration. If a braided nitinol tube is used, it can be pre-formed into a radially expanded configuration whereby occlusion structure 2191 is oriented circumferentially about catheter 2144 with an outer circumference of 360 degrees. As in this example, the mesh can be coated with polyurethane, PTFE, silicone or the like and channels formed through the mesh and valves placed over the channels.

Referring to FIG. 50C, outer catheter 2186 is retracted distally while holding inner catheter 2188 stationary thereby pivoting frame 2192 distally at attachment point 2198 and placing occlusion structure 2191 in its radially constrained configuration.

Referring to FIG. 51, an anatomical structure 2200 is shown with main artery 2202, right artery 2204, left artery 2206, capillaries 2208, tumor 2209 and blood flow directional arrows 2212. FIGS. 51A-51E illustrates a method of the present disclosure wherein a tumor is embolized with drug eluting beads as in Transarterial Chemoembolization (TACE).

Figure 51A:
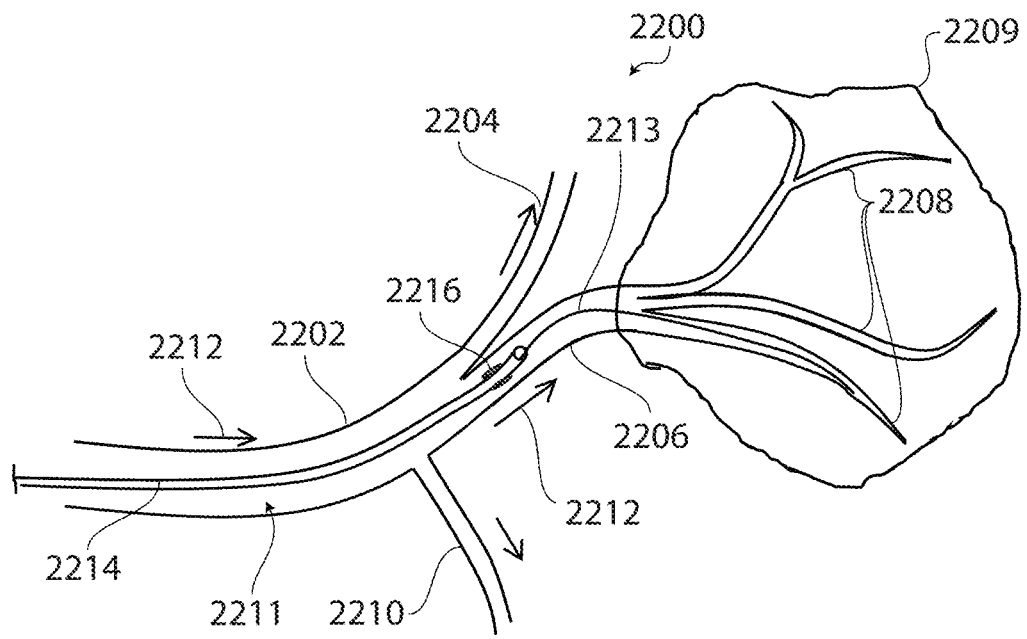
FIGS. 51A, 51B, 51C, 51D, 51E and 51F illustrate a method for delivery of embolic particles using a device of the present disclosure.

In a first step, device 2211, comprising a two lumen catheter 2214 and a radially constrained unidirectional balloon occlusion structure 2216 (also in FIG. 42), is advanced over a guidewire 2213 using lumen one (guidewire/injection lumen) of catheter 2214 from an entry point on the surface of the body, usually the femoral artery at the groin, and positioned at, or in the vicinity of, an artery feeding a tumor as in FIG. 51A. As indicated by arrows 2212, the blood flows in an antegrade direction over device 2211 and into capillaries 2208 of tumor 2209.

Figure 51B:
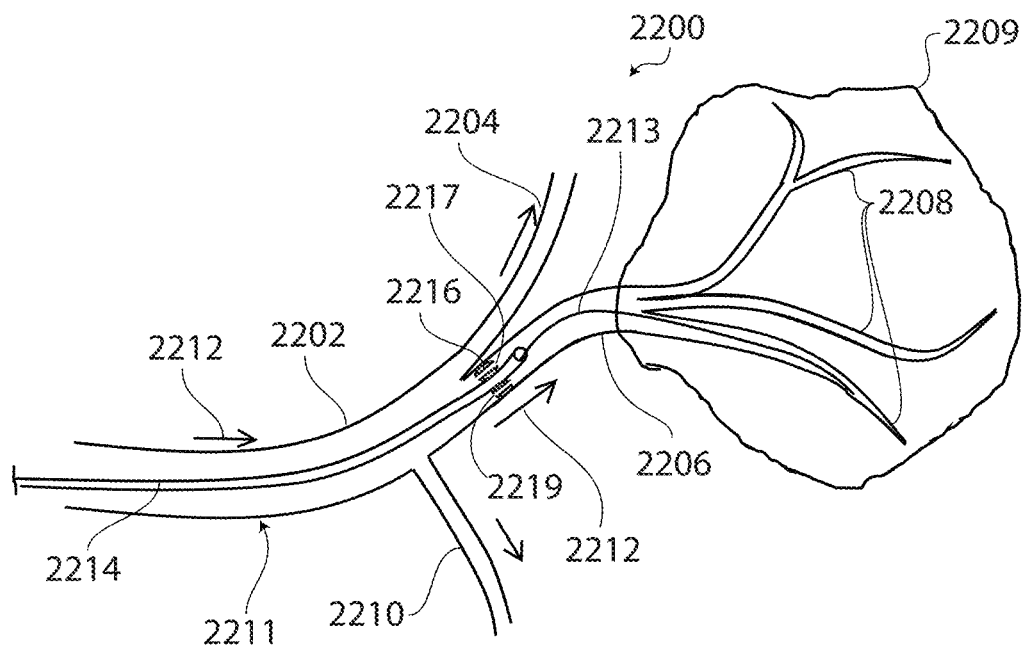

In a second step, the unidirectional balloon occlusion structure 2216 is placed in a radially expanded configuration by inflating the inner balloon of the two layered device of FIG. 42 using the second lumen of catheter 2214 (balloon inflation lumen) as seen in anatomical FIG. 51B. When placed in a radially expanded configuration, normal blood pressure between about 80 mmHg and 130 mmHg urges valves 2217 of occlusion structure 2216 to the open position, thereby allowing antegrade blood flow through channels 2219 and into the capillaries 2208 of tumor 2209.

Figure 51C:
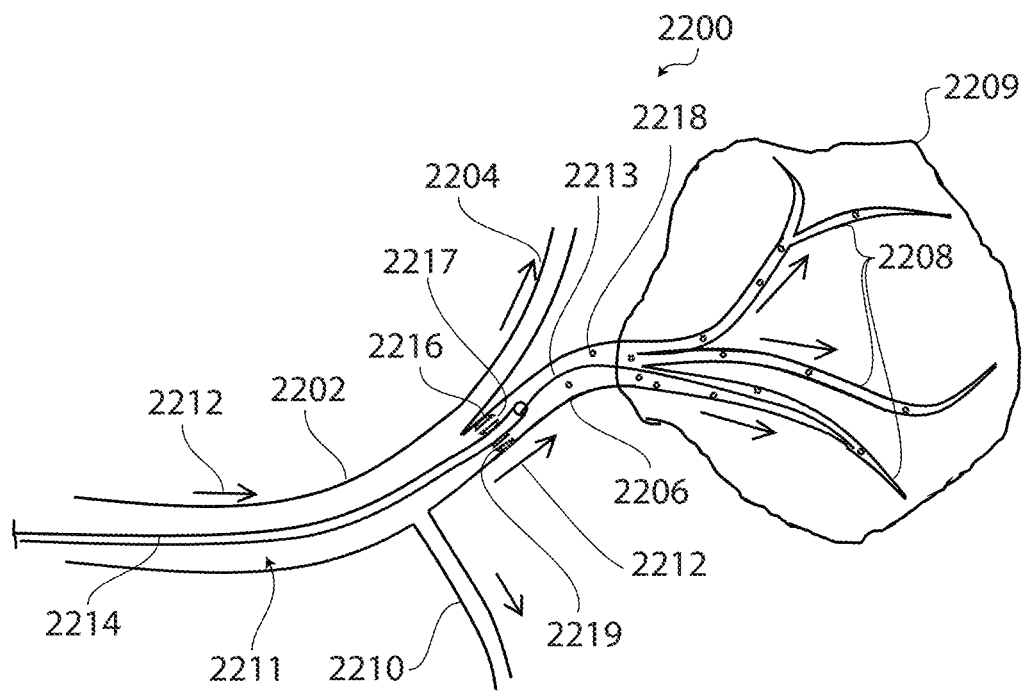

FIG. 51C illustrates a third step whereby chemoembolization particles 2218 are beginning to be injected into left artery 2206 and capillaries 2208 of tumor 209. At this point, valves 2217 of unidirectional occlusion structure 2216 are in the open position and blood is flowing in the antegrade direction through channels 2219 which continues to carry chemoembolization particles 2218 into the vasculature of tumor 2209.

Figure 51D:
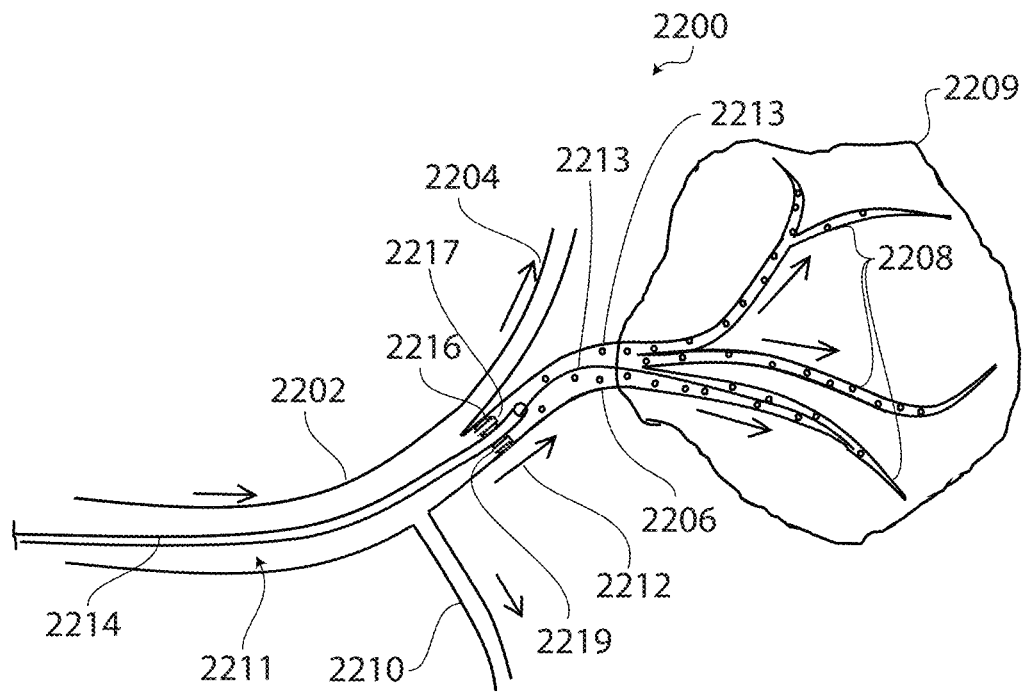

Referring to FIG. 51D, a fourth step is illustrated whereby chemoembolization particles 2218 begin to embolize the distal ends of capillaries 2208, increasing pressure in the proximal section of capillaries 2208 and left artery 2206. This back pressure causes blood flow and chemoembolization particles 2218 to flow in a retrograde direction; however, the back-pressure in left artery 2206 urges valves 2217 to close, thereby maintaining particles 2218 in the vascular compartment distal to occlusion device 2217. Using currently available straight tip catheters, the chemoembolization procedure would be terminated at this point since particles would reflux backward over the catheter and into the general circulation causing non-target embolization and associated complications.

Figure 51E:
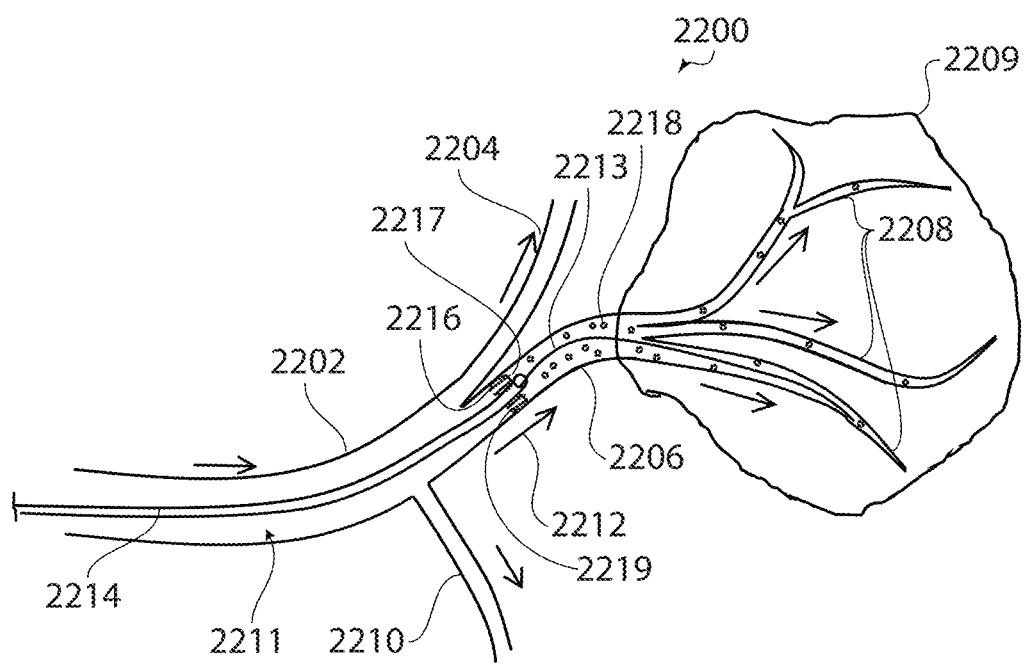

FIG. 51E illustrates a fifth step, not possible using present catheters, whereby embolization particles continue to be injected, without retrograde reflux, and further fill the vasculature of the tumor with particles 2218. This method can both prevent the complications associated with retrograde reflux and allow more particles to enter the tumor.

Figure 51F:
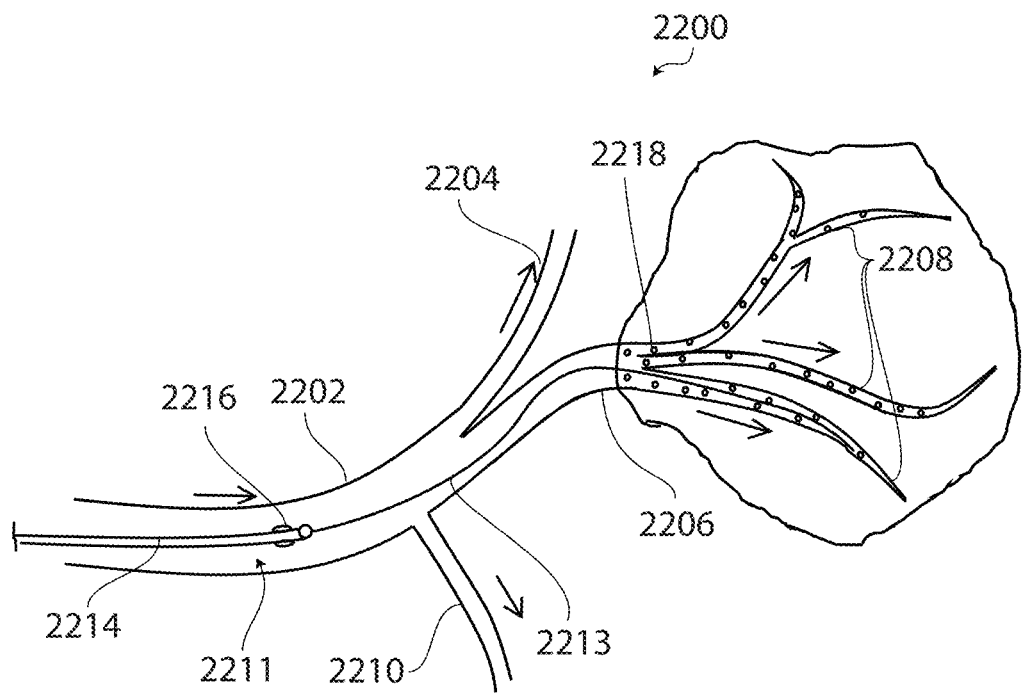

FIG. 51F is a final step in the present method whereby occlusion structure 2216 is placed in a radially constrained configuration and device 2211 is withdrawn from the body over guidewire 2213.

Although particular mention has been given to a device that is capable of transitioning from a radially constrained configuration to a radially expanded configuration, such a transition is not required. A unidirectional occlusion structure of the present disclosure can be configured in a permanently expanded configuration. In this instance, the occlusion structure may be a highly flexible material such as a low durometer plastic or rubber or a flexible mesh or any material or construction that provides sufficient strength and flexibility to navigate through vasculature and to a target and provide unidirectional occlusion.

Figure 52:
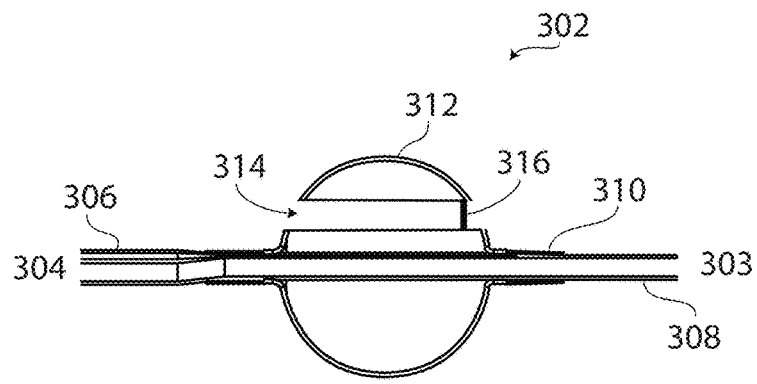
FIG. 52 illustrates a partial occlusion balloon with channel and valve.

Referring to FIG. 52, distal section 302 of a device is shown with distal end 303, proximal end 304, catheter body 306, distal tip 308, nose cone 310, partial occlusion balloon 312 in a fully expanded configuration, channel 314 and one-way valve 316. In this embodiment, flow is permitted in the proximal to distal direction through channel 314 and restricted, by one-way valve 316 to flow proximally. Partial occlusion balloon 312 can be any shape and diameters from 1 mm to 30 mm more typically from 2 mm to 10 mm.

Figure 53:
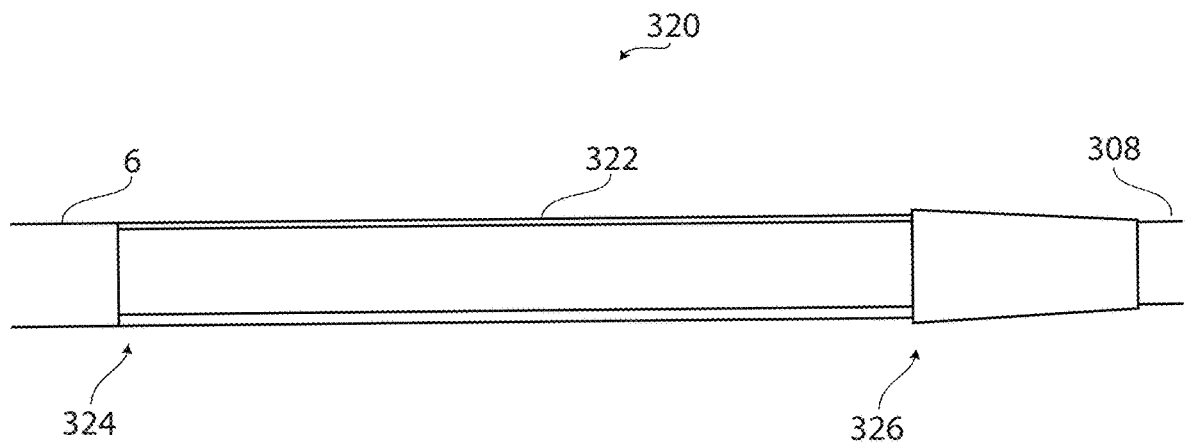
FIG. 53 illustrates a side view of constrained occlusion balloon in catheter pocket.

Referring to FIG. 53, a longitudinal section 320 of a distal section of the device of the present disclosure is shown with catheter body 306 distal tip 308, nose cone 310, radially constrained balloon 322, proximal balloon pocket boundary 324 and distal balloon pocket boundary 326. Radially constrained balloon 322 sits within the pocket defined by the distal end of catheter 306 at boundary 324 and the proximal end of nosecone 310 at boundary 326. The outer diameter of the constrained balloon is approximately equal to the outer diameter of catheter body 306. This allows the balloon to sit within the pocket and maintain the catheter at a desirable minimal diameter.

Referring to FIG. 54A, a distal section 330 of the device of the present disclosure is shown with catheter body 306, catheter extension 307, distal tip 308, nose cone 310, balloon pocket 332, guidewire and injection lumen 334 and balloon inflation lumen 336. The catheter body 306 has a diameter of 0.25 mm to 5 mm, more typically from 0.5 mm to 1.5 mm and a length of 10 cm to 240 cm more typically from 75 cm to 150 cm. The catheter extension 307 has a diameter of 0.25 mm to 3 mm more typically from 0.4 mm to 1 mm and a length of 5 mm to 100 mm more typically from 5 mm to 40 mm. The balloon pocket 332 has a depth equal to the difference in diameter of the catheter body 306 and the catheter extension 307 and a length of 1 mm to 50 mm more typically from 5 mm to 15 mm. The balloon wall thickness and inner diameter are selected, extruded or molded to fit into balloon pocket 332 with minimal balloon extending above of balloon pocket 332.

Referring to FIG. 54B, distal section 330 includes a balloon 338 in a radially constrained configuration held within balloon pocket 332 and having an outer diameter approximately equal to the outer diameter of catheter body 306.

Referring to FIG. 54C, distal section 330 includes balloon 338 in a radially expanded configuration with channels 314 and one-way valves 316 in a closed orientation. Partial occlusion balloon 338 can be any shape and diameters from 1 mm to 30 mm more typically from 2 mm to 10 mm and a length of 1 mm to 50 mm more typically from 5 mm to 15 mm. Channels 314 can be of any shape and configuration and an opening that is calibrated to the desired flow therethrough. In a preferred embodiment, the balloon will have a diameter of 6 mm and a channel diameter of 0.5 mm to 1.5 mm. Balloon 338, including channels 314 can be formed by molding, extruding, vacuum forming or otherwise shaping a material to include the desired number and configuration of channels. Alternately, a standard balloon, including but not limited to, round or oval, can be modified to achieve proximal to distal channels. One method to modify a balloon is by forming longitudinal pleats circumferentially oriented; thereby forming V shaped channels that extend from the proximal end of the balloon to the distal end of the balloon. Placing a sheath or film over such a modified balloon results in longitudinal channels and a one way valve as described in co-pending application 61/917,131.

Referring to FIG. 55A through 55C, a serial construction of the device of the present disclosure is illustrated.

Referring to FIG. 55A, a longitudinal view of device construction 350 with catheter body 306, distally located catheter extension 307 and proximally located hub 352 comprising guidewire and injection port 354 and balloon inflation/deflation port 356.

Referring to FIG. 55B, a longitudinal view of a device construction 350 is shown with added nose cone 310 and balloon pocket positioned between the distal end of catheter body 306 and the proximal end of nose cone 310.

Referring to FIG. 55C, a longitudinal view of the device 358 of the present disclosure is shown with catheter body 306, balloon 340 and hub 352. Balloon 340 is shown in a radially expanded configuration with channels 314 and valves 316 in the open position.

Figure 56:
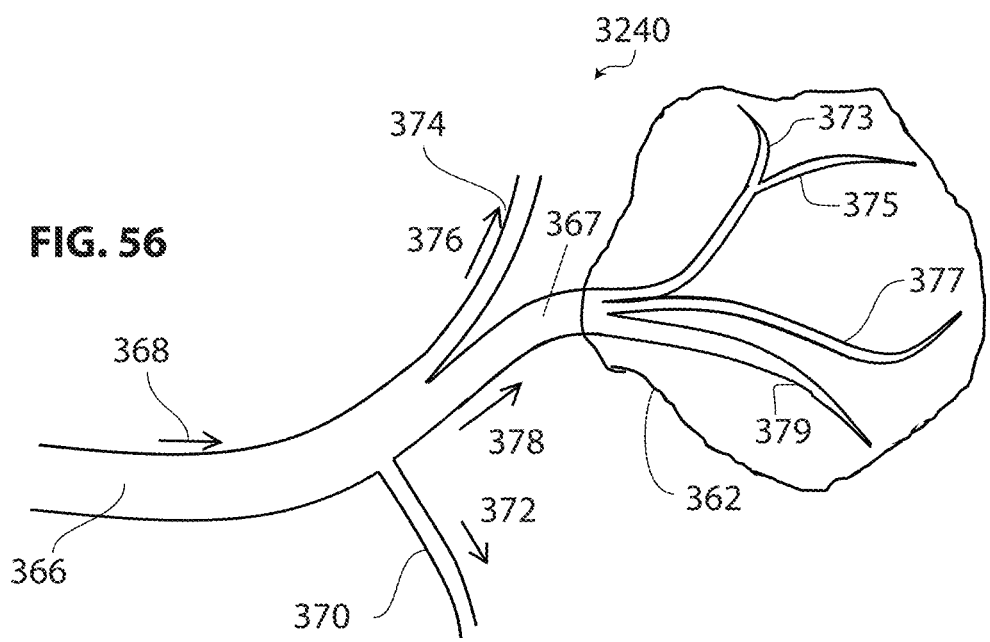
FIG. 56 illustrates liver vasculature and associated tumor vasculature.

Referring to FIG. 56, an anatomical structure 360 is shown with tumor 362, main artery 366, distal main artery 367, side branch arteries 370 and 374, tumor capillaries 373, 375, 377 and 379 and blood flow direction arrows 368, 372, 376 and 378. In the case of a tumor in the right liver lobe, artery 366 is the right hepatic artery and 367 is the distal right hepatic artery which flow toward the tumor as seen by flow direction arrow 368 and 378. In this instance, artery 370 is the gastroduodenal artery and artery 374 is a hepatoenteric artery such as the superduodenal artery, the normal flow of both is away from the hepatic artery, as shown by flow direction arrows 372 and 376, and into arterial networks which supply both the liver and gastrointestinal tract. Blood from the hepatic artery 366 also flows into the tumor capillaries 373, 375, 377, and 379. Normal blood flow through the right hepatic artery is in the range of 4 ml/sec.

Referring to FIG. 57A through 57H, a tumor embolization method according to current medial practice is shown. At least some of the steps shown are used in current catheter based embolization therapy in tumors of the liver The first step of the procedure is to advance guidewire 382 from the femoral artery at the groin, through the iliac artery, aorta, celiac artery, hepatic artery and into the right hepatic artery 366 as in anatomical structure 380 of FIG. 57A. The diameter of guidewire 382 is typically from about 0.25 mm to 1.25 mm more typically from 0.4 mm to 1 mm.

In the second step of the procedure, illustrated in FIG. 57B, guide-catheter 392 is advanced over guidewire 382 and along the same arterial path as for guidewire 382. Typically, the guide catheter has an outer diameter of about 1.5 mm to 2.5 mm and has a central lumen that can accept a microcatheter with an outer diameter of 0.5 mm to 1.5 mm. The guide catheter is too large to access the vasculature in the vicinity of the tumor and is typically advanced as far along the vascular path toward the tumor as possible. The blood flow follows the same normal pattern as in FIG. 56 and flows around the sides of guide catheter 392.

In the third step shown in FIG. 57C, guidewire 382 is optionally removed and replaced with a smaller diameter guidewire 398 that can fit in the central lumen of a microcatheter. Guidewire 398 typically has a diameter of 0.2 mm to 0.75 mm, more typically in the range of 0.25 mm to 0.6 mm.

Figure 57A:
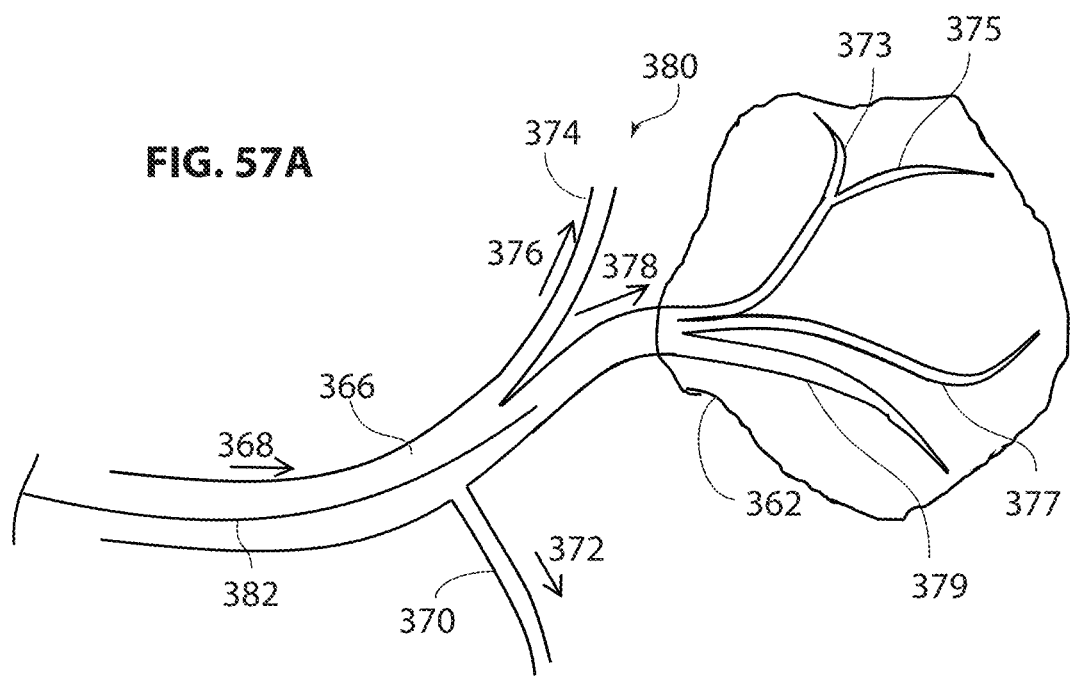
Figure 57D:
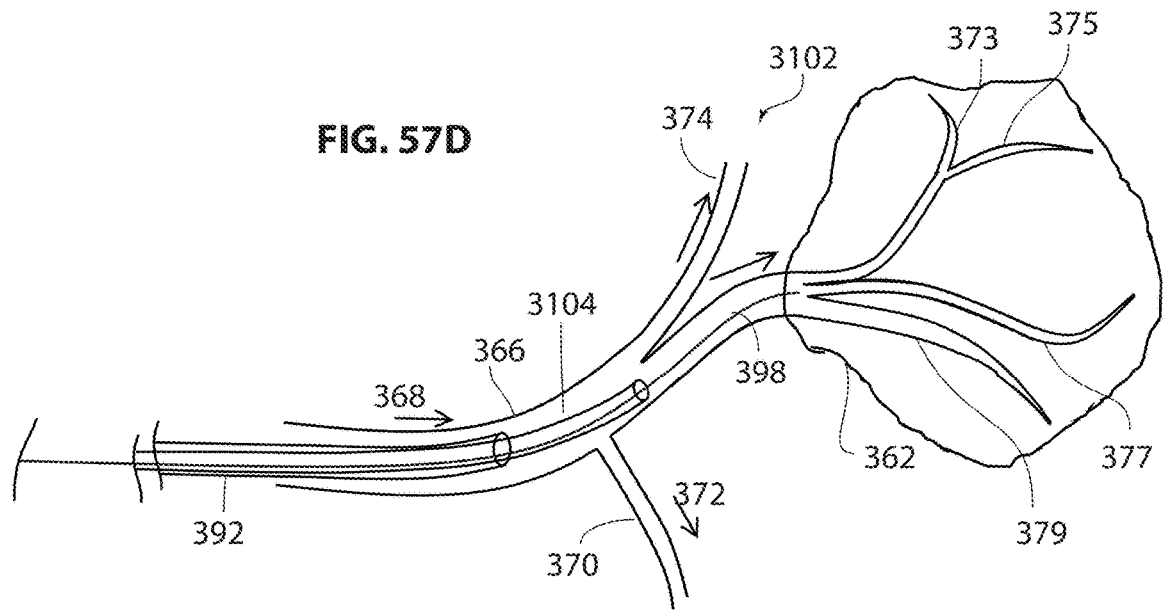

The fourth step of the procedure, microcatheter 3104 is advanced over guidewire 398 to a position beyond the distal end of guide catheter 392 and into the vasculature within or in the vicinity of the tumor as shown in anatomical structure 3102 of FIG. 57D. Microcatheter 3104 is advanced as close as is practical to the tumor and, if the anatomy allows, into the vasculature of the tumor as in superselective embolization. Microcatheter 3104 typically has a diameter of 0.75 mm to 1.5 mm, more typically at about 1 mm and a total length of 50 cm to 200 cm, more typically from 75 cm to 150 cm. The central lumen microcatheter 3104 is optimized to have an inner diameter as large as possible; however it is usually in the range of about 0.5 mm.

Figure 57E:
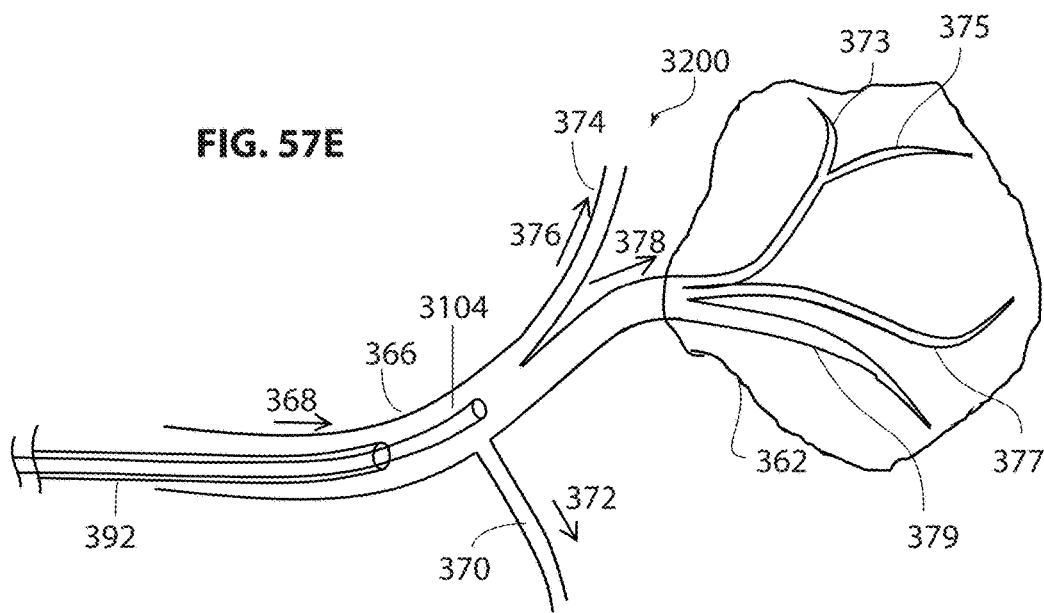

In a fifth step, guidewire 398 is removed from microcatheter 3104 as illustrated in anatomical structure 3200 of FIG. 57E. Removal of guidewire 398 allows the central lumen of microcatheter 3104 to be used to inject drug and/or embolic materials into the target site within the right hepatic artery and tumor. Blood continues to flow around guide catheter 392 and microcatheter 3104 and into capillaries 373, 375, 377, and 379 of tumor 362, gastroduodenal branch 370 and hepatoenteric branch 374 according to the normal flow pattern shown by arrows 368, 372, 376, and 378.

Figure 57F:
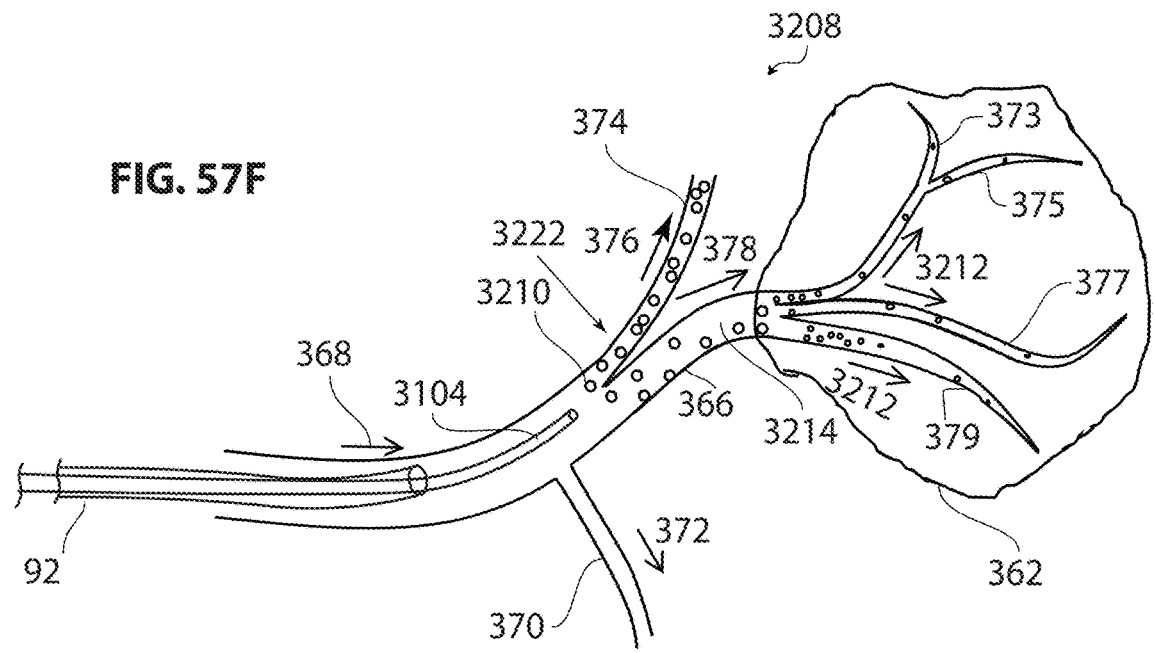

In a sixth step illustrated in anatomical structure 3208 of FIG. 57F, drug and or embolization agents are injected using a syringe or other means from the proximal end of microcatheter 3104 through guidewire/injection port 354 of hub 52 (FIG. 55), longitudinally through guidewire injection lumen 334 (FIG. 54), and out the distal end of catheter extension 307. In this instance, embolic particles 3210 are carried by normal blood flow into distal right hepatic artery 3214, tumor capillaries 373, 375, 377 and 379, as illustrated by flow arrow 3212, and into hepatoenteric artery 374 in the direction indicated by flow arrow 376. Drug and/or embolization agents that travel through gastroenteric branch artery 374 or any other arterial branch distal to the distal tip of microcatheter 3104, by normal forward flow, are deposited at non-target sites, including parts of the liver and intestine. This antegrade (to the catheter tip) bypass into distal hepatoenteric arteries can cause serious complications including damage or death to sections of the liver or intestine, gastric ulcers or even the death of the patient. Further, drug and/or embolic agents that travel to non-target sites, fail to enter the tumor; this resulting in a lower than optimal dose to be delivered to the tumor and a lower efficacy than desired. However, to avoid the aforementioned serious complications, physicians often under-embolize the tumor vasculature.

Figure 57G:
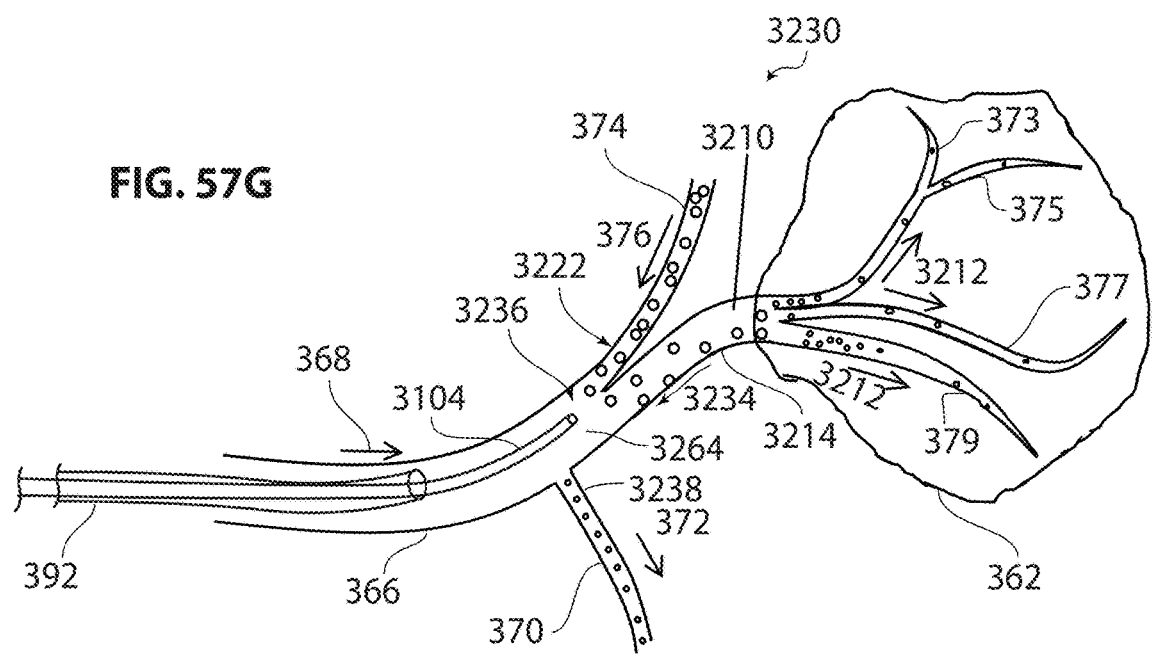

Referring to FIG. 57G, as forward flow mediated embolization progresses, the distal ends of capillaries 373, 375, 377 and 379 fill with particles 3210 and become embolized. This process dramatically slows the blood flow moving through the tumor and causes a sharp rise in pressure within the tumor vasculature and concomitant retrograde deflection of the high volume blood flow from the hepatic artery. Further, backpressure develops in the distal hepatic artery 3214, resulting in particles to flow in a retrograde direction as in flow direction arrow 3234. This can result in: (1) increased antegrade bypass into hepatoenteric branch 374, reflux over the catheter and into gastrodudenal artery 370 and (3) a signal to the physician that particle injection should stop, even though the tumor is only partially embolized. In this instance, it is possible that larger capillaries become embolized first, due to a larger blood flow while smaller capillaries remain un-embolized. The rapid rise in pressure is in part caused by distal capillary embolization and in part caused by the high volume blood flow from the hepatic artery. Given that embolization is the desired endpoint, it appears that slowing the forward flow of blood from the hepatic artery would allow the tumor to accept the blood and drug and/or embolic agent flow for a longer period of time and allow more embolization to occur and an improved distribution of particles in the tumor vasculature.

Figure 57H:
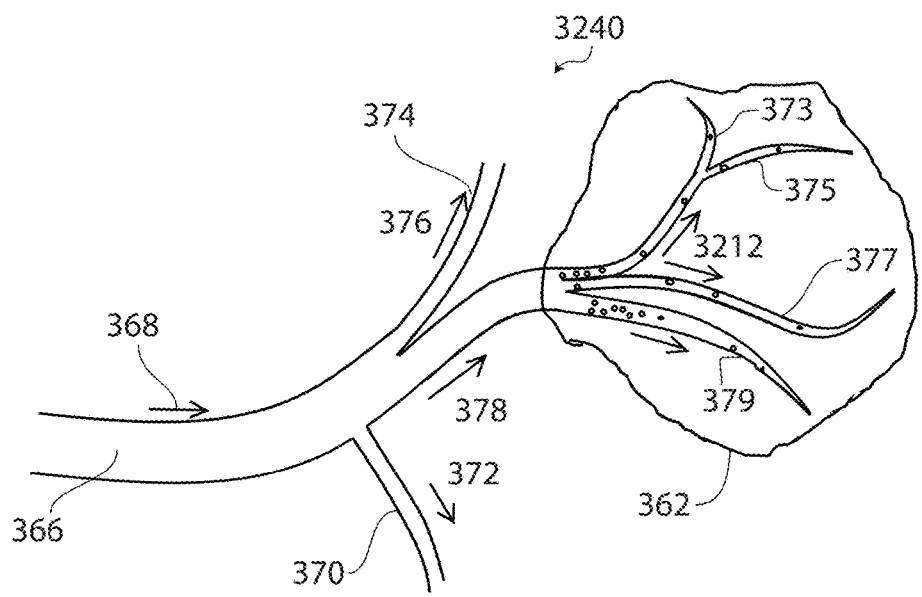

Referring to FIG. 57H, injection of drug and/or embolic agents is complete, microcatheter 3104 and guide catheter 392 are removed and the final embolization distribution in tumor capillaries 373, 375, 377 and 379 is shown where, in this example, lager capillary 379 is embolized to the greatest extent, smaller capillary 377 is embolized to a lesser extent and small capillary 373 remains un-embolized.

Referring to FIG. 58, a method of tumor embolization, according to the device of the present disclosure is shown. Steps 1 through step 5, shown in FIGS. 57A through 57E, are the same for both a standard catheter as shown in FIG. 57 and the device of the present disclosure and are not further illustrated.

Figure 58A:
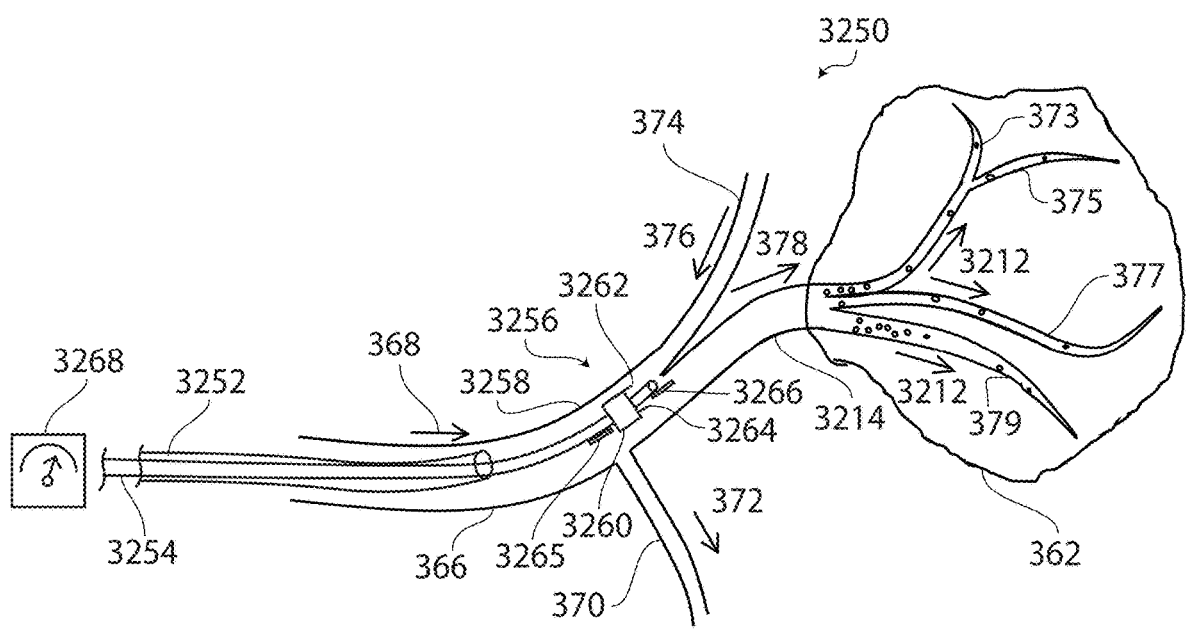
FIGS. 58A, 58B, 58C, 58D and 58E illustrate a tumor embolization method for the catheter of the present disclosure.

Referring to FIG. 58A, the device of the present disclosure is positioned in the distal right hepatic artery 3214, with partial occlusion balloon 3256 in its radially expanded configuration comprising channels 3258 and 3260, and one-way valves 3262 and 3264 that are in the open position. FIG. 58A shows two channels, however, one, two, three or any number of channels can be used. With or without valves. The maximum channel size is limited by balloon diameter, but can be as small as is practical. Valves 3262 and 3264 can be flap, duck bill, diaphragm, or any type of valve provided that it permits flow only in one direction. Optional pressure sensors 3266, which provides real time pressure measurement in the vascular space distal to partial occlusion balloon 3256 and pressure sensor 3265 which provides real time pressure monitoring in the vascular space proximal to the partial occlusion balloon 3256 are shown. Pressure sensor 3266 which measures pressure in the distal vascular space can be used to signal a procedural endpoint based on a predetermined or non-predetermined pressure reading. This will, for the first time, allow a quantitative and definitive pressure mediated endpoint rather than the present subjective flow mediated endpoint and will enable the procedure to be reproducible and able to be standardized allowing center to center and physician to physician consistency. This is possible only because the vascular space distal to the partial occlusion balloon 3256 is isolated from the vascular space proximal to partial occlusion balloon 3256, thereby allowing that the arterial pressure in the distal space to be closely related to the intra-tumor arterial blood pressure. Blood flow direction through hepatic artery 368, distal hepatic artery 3214 and proximal artery 370 are normal as seen in flow direction arrows 368, 372 and 378 as is the blood flow in tumor capillaries 373, 375, 377 and 379 and illustrated by flow direction arrows 3212. However, partial occlusion balloon 3256 causes a significant reduction in blood flow in distal right hepatic artery 214 and in tumor capillaries 373, 375, 377 and 379. Blood flow can be regulated by the partial occlusion balloon of the present disclosure such that total flow can range from near 100% (unconcluded flow) to near 0% as in full occlusion. Of most interest is partial occlusion that results in 1% to 25% flow as compared to the unoccluded artery. Therefore, channels 3258 and 3220 allow only a fraction of normal blood flow to pass distally. Blood pressure distal to partial occlusion balloon 3256 is also dramatically reduced by anywhere from about 5 mmHg reduction to 100 mmHg reduction, depending on the nature of the occlusion. This pressure drop causes branch artery 374 to reverse direction as seen by flow direction arrow 376 and now flow toward the distal main artery 3214 and tumor capillaries 373, 374, 377 and 379. The flow reduction and pressure reduction caused by partial occlusion balloon 256 also reduces the flow and pressure within the tumor capillaries 373, 374, 377 and 379. This is of significance because it allows more drug/embolization agents to enter the tumor before backpressure causes flow stasis and retrograde flow.

Figure 58B:
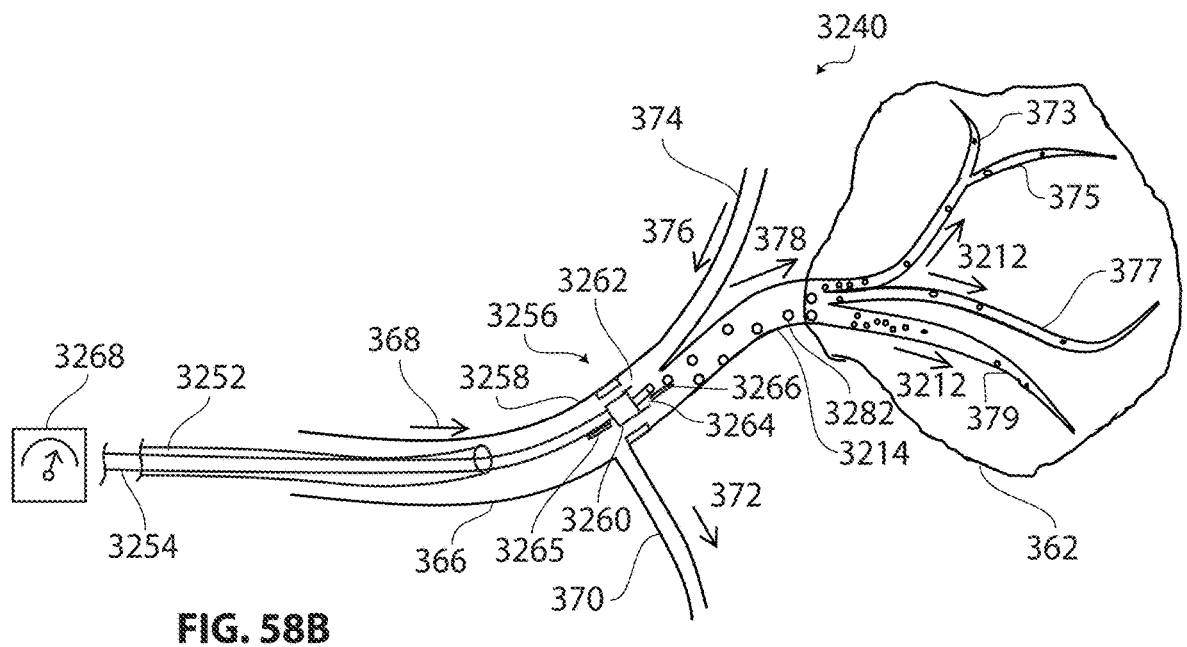

Referring now to anatomical structure 3280 of FIG. 58B, injection of drug and/or embolic agents is initiated. Blood flow from the proximal main artery 366 is attenuated as it passes through channels 3258 and 3260 and into distal main artery 3214. The anti-cancer agents are carried by the attenuated forward blood flow through distal main artery 3214 and into tumor capillaries 373, 375, 377 and 379. Valves 3262 and 3264 are in the open position as pressure in the distal vascular space is lower than the blood pressure in the vascular space proximal to partial occlusion balloon 3256. Branch artery 374 continues to flow in the reverse direction as indicated by flow direction arrow 376 since blood pressure in the distal right hepatic artery is lower than that of the arterial network connected to the distal end of branch artery 374. In this instance, antegrade drug/embolic agents are prevented from flowing into branch artery 374 and antegrade bypass and non-target delivery does not occur. Optional pressure sensors 3266 and 3265 or pressure measurement through guidewire/injection lumen 334 of catheter 6 (FIG. 54A) can be used to monitor real-time pressure.

Figure 58C:
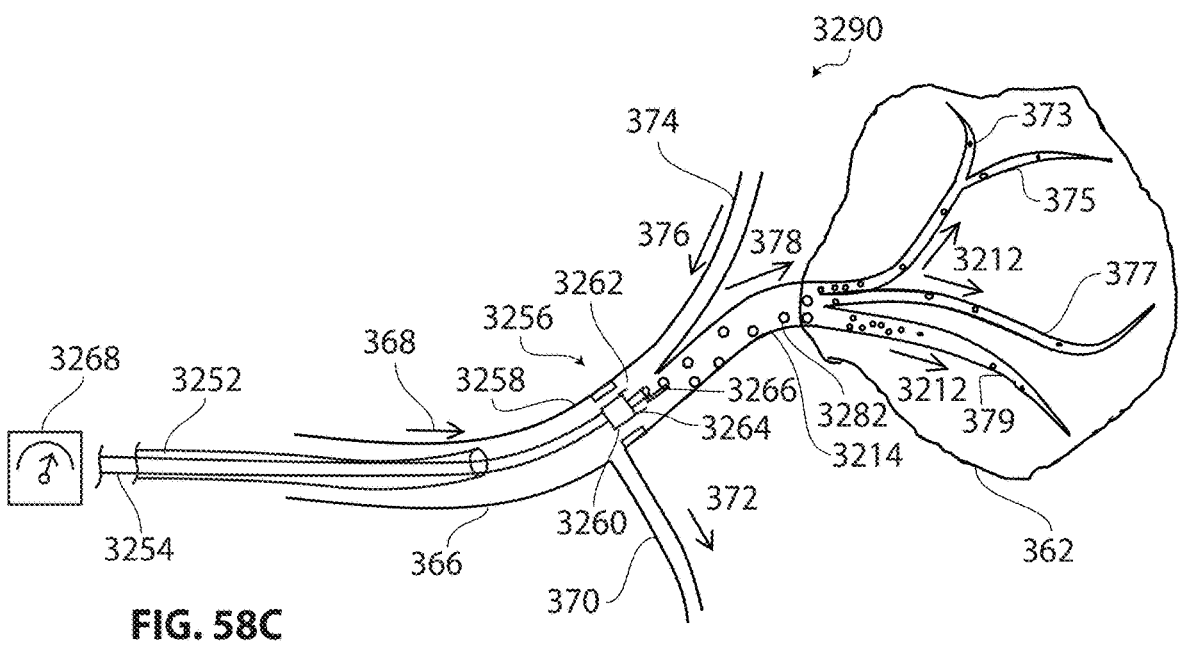
Figure 58D:
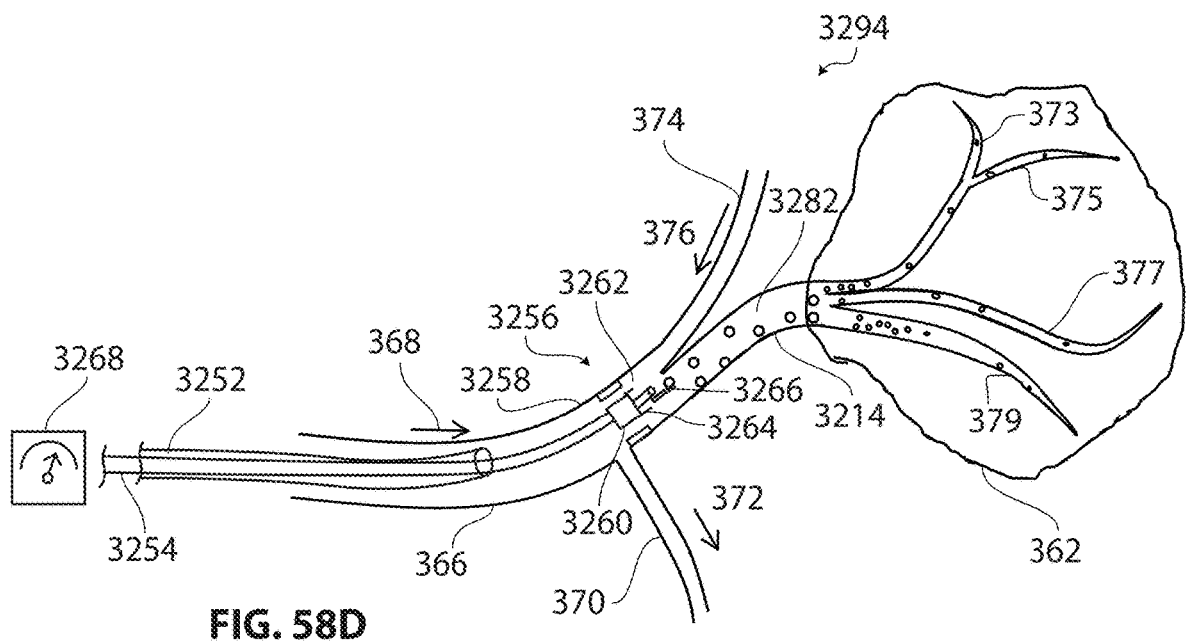

Referring to FIG. 58C, and looking at anatomical structure 3290, a slower rate of blood flow and lower pressure through distal hepatic artery 3214 allows tumor capillaries 373, 375, 377 and 379 to fill at a slower pace and to a greater distribution than in the current method of full unregulated forward flow. At some point, however, the embolization of tumor capillaries will cause retrograde deflection of blood and anti-tumor agents and a pressure build up in distal hepatic artery 3214 as in FIG. 58D. At this point, the increased pressure in distal right hepatic artery 3214 causes valves 3262 and 3264 to close, preventing retrograde flow and non-target embolization through branch artery 370 or any other arteries proximal to partial occlusion balloon 3256. This retrograde deflection and pressure build up will progress at a slower rate as compared to the current standard method of FIG. 57. The slower buildup of pressure and retrograde flow allows a larger time window for the physician to terminate the procedure. If pressure monitoring is done, a defined pressure can be used to terminate the procedure. If the back pressure in distal hepatic artery 3214 exceeds about systolic pressure and/or mean arterial pressure, branch artery 374 will again follow in the normal flow pattern as illustrated in the flow direction arrow 376 of FIG. 56. This situation will allow antegrade drug and/or embolic agents to flow in branch artery 374 and to non-target sites. However, visual observation of contrast movement in branch artery 374 or a defined pressure measurement at or below the flow reversal pressure of branch artery 374 can be used as a procedural endpoint signal.

Figure 58E:
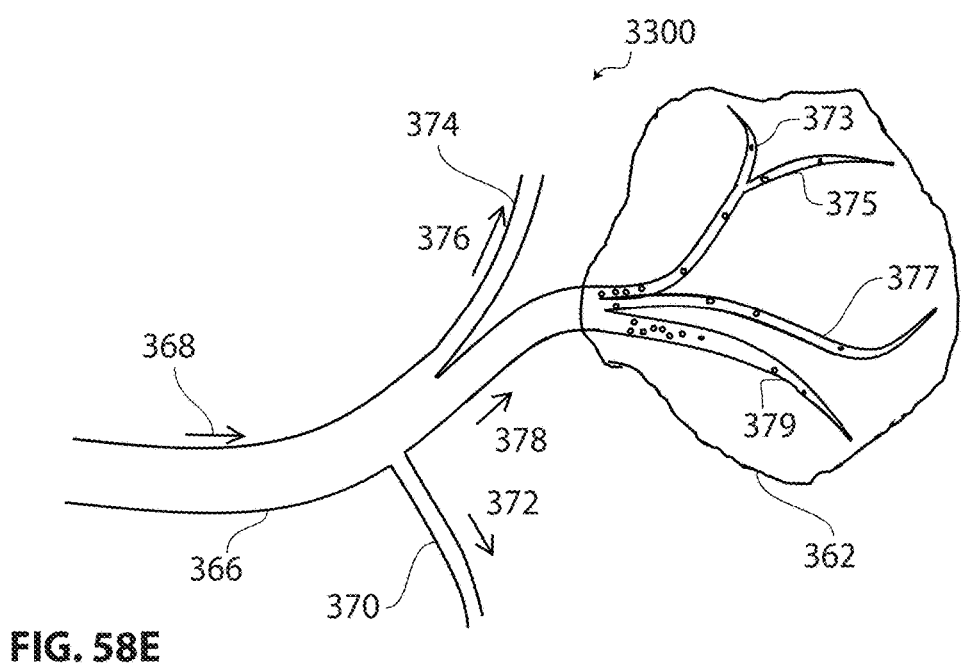
Figure 59A:
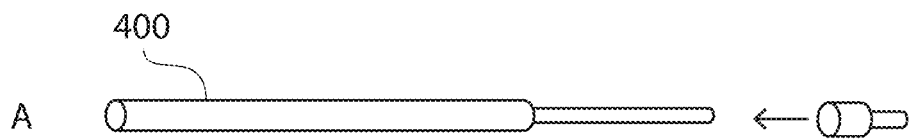
FIGS. 59A, 59B, 59C and 59D illustrate fabrication steps of the distal end of an occlusion catheter according to aspects of the present disclosure.
Figure 59B:
Figure 59C:
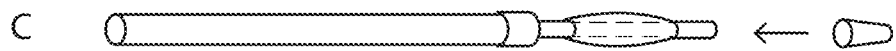
Figure 59D:
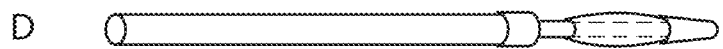

Referring now to anatomical structure 3300 of FIG. 58E, the procedure is complete and catheter 3254, of the present disclosure, and guide catheter 3252 are removed. The distribution and filling of tumor capillaries 373, 375, 377 and 379, using the device of the present disclosure, are improved as compared to the distribution and filling associated with the current microcatheter 3104 of FIG. 57H.

In some embodiments, a pressure feedback loop is implemented to control the rate of fluid introduction (e.g. the rate of embolic bead injection). In such embodiments, a blood pressure sensor may be located at the distal tip of the catheter to monitor the pressure of the vasculature distal to the occlusion or partial occlusion structure. In some embodiments, a predetermined pressure set point may be used. The set point may be an absolute pressure, or a percentage of systolic and/or mean arterial pressure (such as about 100% of systolic and/or mean arterial pressure). Such systems can be programmed to maintain the distal vasculature at or below the set point by automatically controlling the infusion rate (e.g. the rate or pressure of an injection pump.) By ensuring that the pressure of the distal vasculature does not exceed systolic and/or mean arterial pressure, retrograde and/or other undesirable blood flows can be prevented.

In some embodiments, a rate of pressure change can be used instead of or in addition to a preset pressure in the pressure feedback loop. For example, if the distal vasculature pressure begins to rise faster than a predetermined rate, the rate of embolic substance injection can be slowed, temporarily stopped, or a procedural endpoint may be signaled. The endpoint signal may be an audible, visual, tactile or other signal to persons involved in the procedure, and/or may be a signal that automatically shuts off or changes the state of medical equipment used in the procedure.

FIGS. 59A-59D show the fabrication steps of the distal end of an occlusion catheter 400 according to aspects of the present disclosure.

Figure 60:
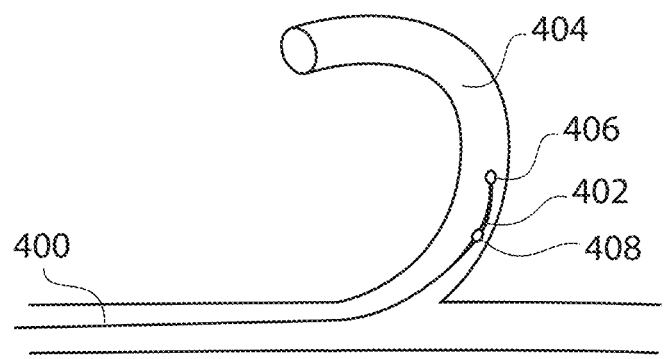
FIG. 60 illustrates the completed distal end of the occlusion catheter of FIGS. 59A-59D being introduced into small branches of a vascular system.

FIG. 60 shows the completed distal end 402 of the occlusion catheter 400 of FIGS. 59A-59D being introduced into small branches of a vascular system 404. The two enlarged contact points 406 and 408 of this design allow the catheter 400 to be navigated into smaller vasculature than can be navigated by conventional catheter tips.

Figure 61A:
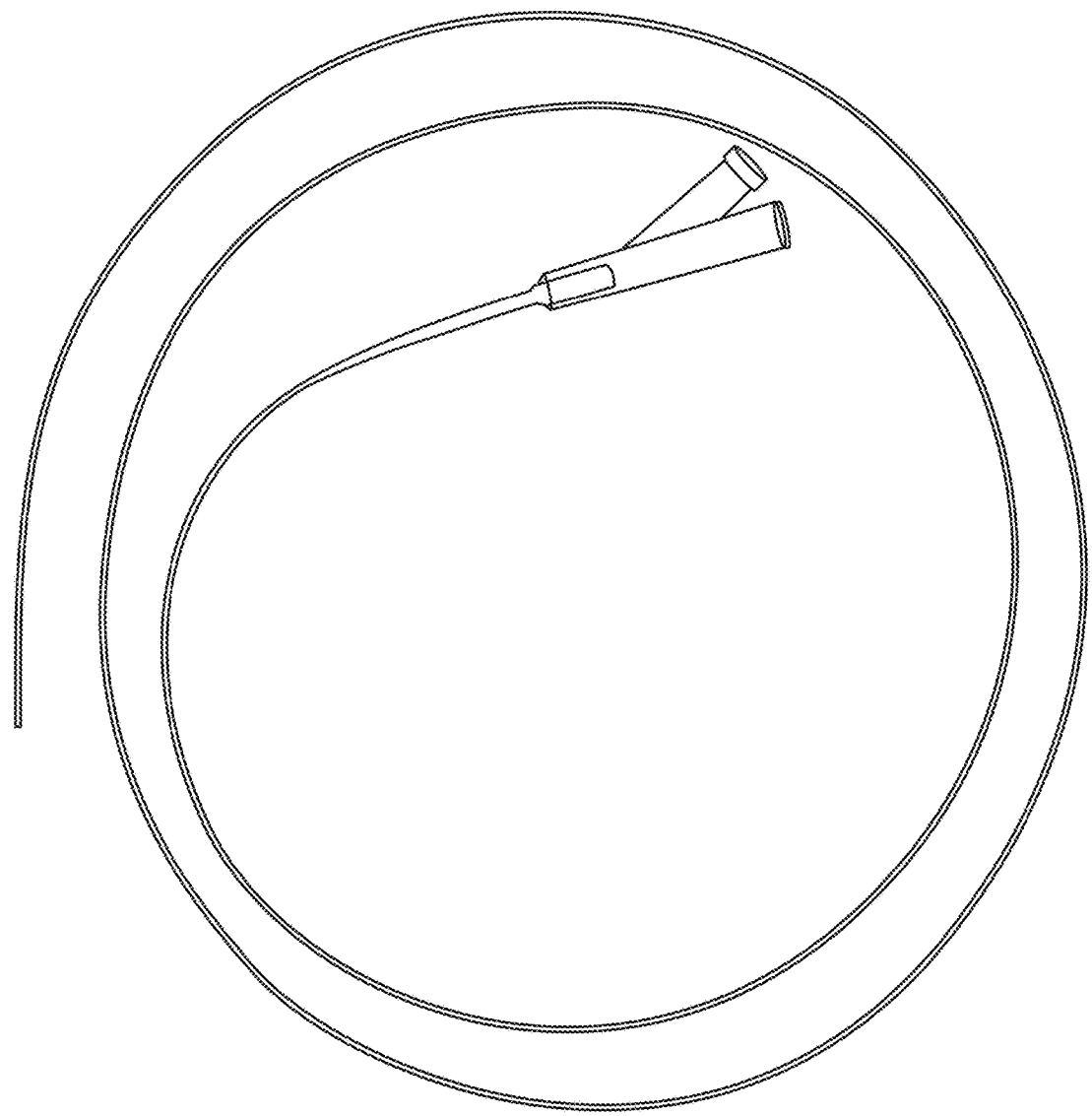
FIG. 61A shows an entire occlusion catheter constructed according to principles of the present disclosure.
Figure 61B:
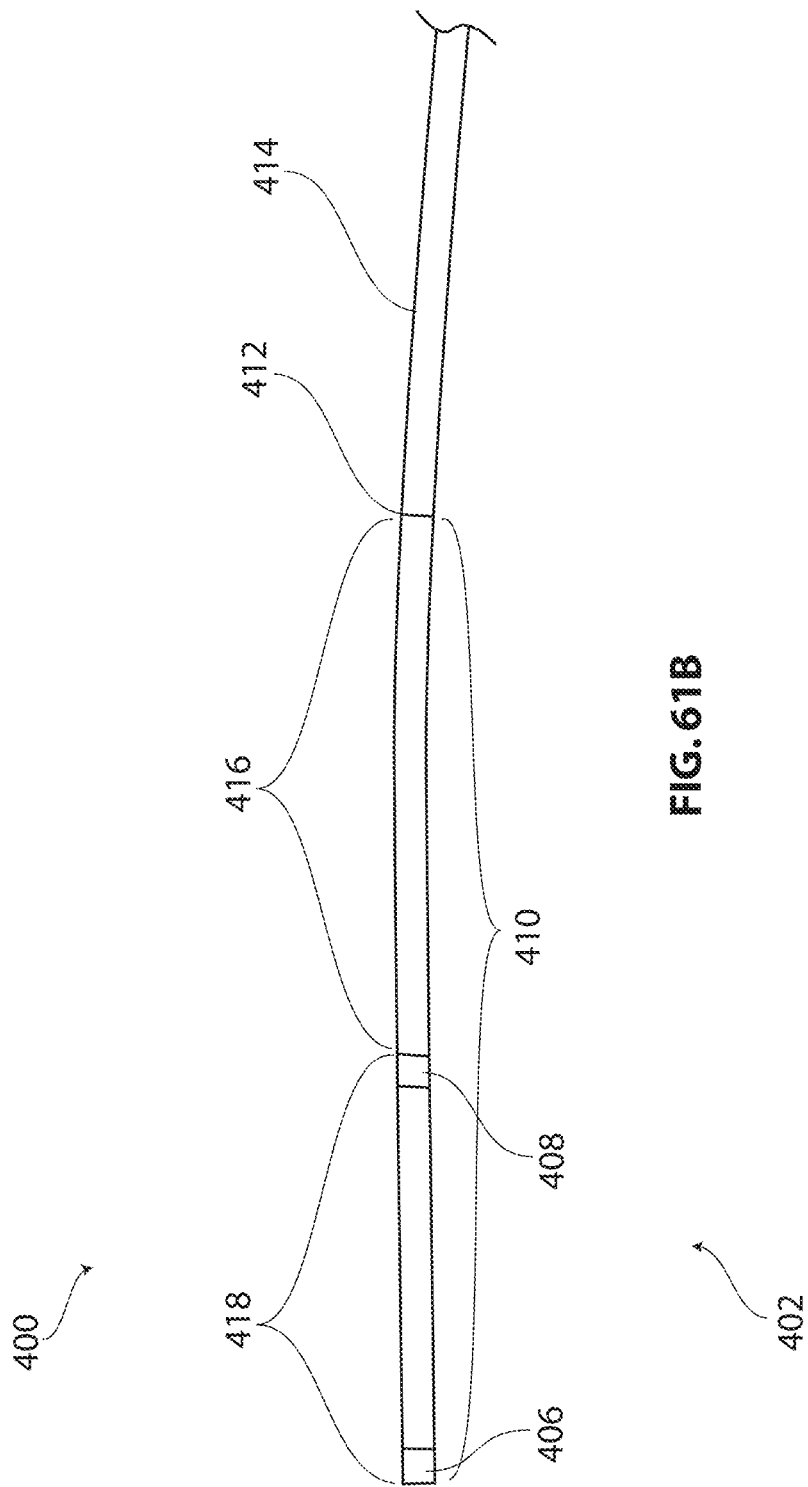
FIG. 61B shows details of construction features on the distal end of the occlusion catheter of FIG. 61A.

FIG. 61A shows an entire occlusion catheter constructed according to principles of the present disclosure. FIG. 61B shows details of construction features on the distal end 402 of the occlusion catheter 400 of FIG. 61A. These details include a catheter extension 410 (which may comprise a coaxial inner catheter) extending from the distal end 412 of the catheter body 414, which includes a balloon pocket section 416 and a distal tip section 418. A nose cone radio-opaque marker 408 is located at the proximal end of the distal tip section 418, and a radio-opaque marker 406 is located at the distal end of the distal tip section 418. As previously mentioned, both markers 406 and 408 have enlarged diameters as compared with the diameter of the adjacent distal tip section 418.

Figure 62:
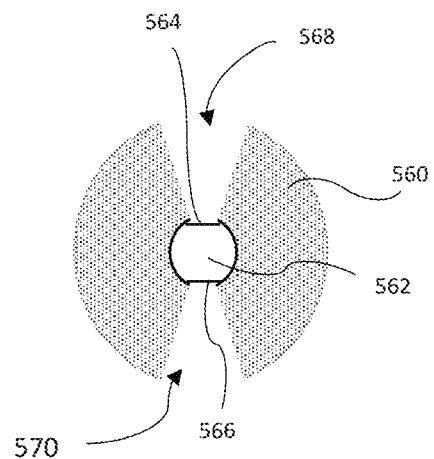
FIG. 62 shows a representative arterial system located adjacent to target tissue, before occlusion.

Referring now to FIG. 62, an axial cross-section of an alternative catheter balloon design is shown. In this design, a single balloon 560 is concentrically aligned over inner catheter 562. During manufacture, balloon 560 is longitudinally bonded to inner catheter 562 in two locations 564 and 566, circumferentially spaced 180 degrees apart. This arrangement provides two generally V-shaped channels 568 and 570 when balloon 560 is inflated, as shown. These longitudinal V-shaped channels keep balloon 560 from fully occluding a blood vessel by allowing a portion of the normal blood flow to bypass the balloon through the channels. By specifying and controlling the dimensions of this construction, predetermined bypass flow rates may be obtained.

The longitudinal bonds 564 and 566 may be formed by ultrasonic welding, heat staking, adhesive, fasteners, or other suitable arrangements. Inner catheter 562 many include flat portions or grooves where the bonds are located, as shown, or may have an entirely round circumference. In other embodiments (not shown), a single channel or more than two channels may be formed. The channel(s) may run the entire length of the balloon or less than the entire length. In some embodiments the balloon segments when inflated may be more rounded than those shown in FIG. 62.

Figure 63:
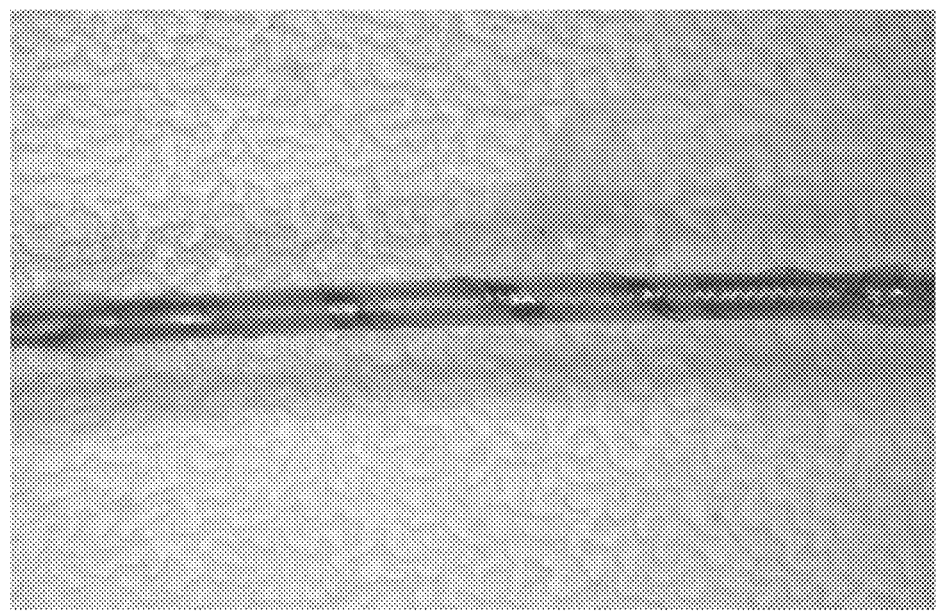
FIG. 63 shows the representative arterial system of FIG. 62 after a temporary occlusion is introduced.
Figure 64:
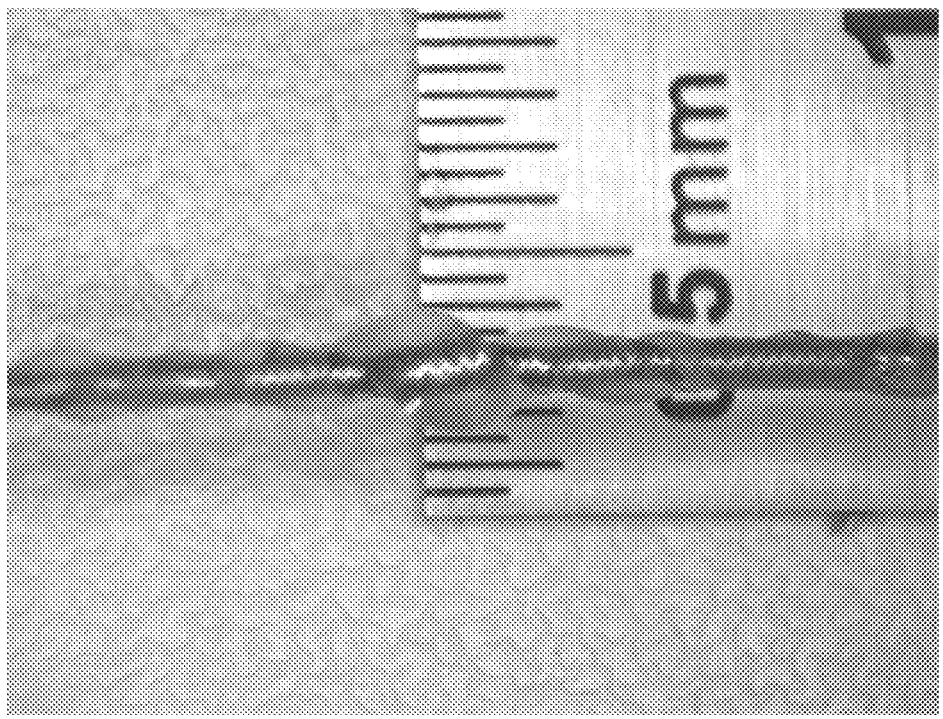
FIG. 64 shows target tissue and immediately adjacent arteries and capillaries, before occlusion.

Referring now to FIGS. 63 and 64, a catheter balloon having spiral channels is shown. FIG. 63 shows one embodiment in a deflated configuration while FIG. 64 shows the balloon in an inflated configuration. The balloon can be slender and elongated, and wrapped around the inner catheter in a spiral fashion leaving a spiral channel formed between windings. In this arrangement, the balloon can be inflated from its proximal or distal end. Alternatively, a larger balloon can be placed coaxially over the inner catheter and secured in place by a spiral wound wire. When the balloon is inflated, only the portions between the wire winding will inflate, leaving a spiral channel having a wire running along its inner diameter. In some embodiments, the coaxial balloon can be bonded to the inner catheter, as previously described but in a spiral rather than a straight fashion. Two or more wires or bonds can be placed in parallel, forming two or more separate but interlaced spiral channels. With any of these configurations, the spiral channels can be sized to provide the desired range of bypass flows across the occlusion balloon.

Referring now to FIGS. 65-73, additional embodiments are shown and described, as well as animal testing results and refined understandings of flow models for previously described embodiments. In conjunction with the following descriptions the following definitions are used:

A "Drug" includes, but is not limited to, embolic agents, therapeutic agents, anticancer agents, fillers, glue, foam, ablative agents, sclerotherapy agents, contrast agents, nutrients, and any fluid or material that can be delivered through the lumen of a catheter.

"Mean arterial pressure" is the mean blood pressure at a particular point or points in the arterial vessel system during a particular time period as the blood pressure varies between the systolic pressure and the diastolic pressure with each pulse.

"Normal mean arterial pressure" is the mean arterial pressure at a particular point or points in the arterial vessel system when no temporary occlusions are in place.

A "Target" is a tissue, organ, defined space within a tissue, part of an organ, tumor, or any other anatomical structure, in whole or in part, such as primary and metastatic tumors, prostate, uterus, pancreas, spleen, bladder, stomach, kidney, liver, gallbladder, thyroid, eye and bone and any other tissue or organ system in the human body.

A "Supply Artery" is one that delivers blood to the target and is in fluid communication with one or more collateral vessels, arteries, arterioles, capillaries, and/or anastomotic vessels.

A "Collateral" includes, but is not limited to, an artery, arteriole or capillary that branches from or anastomoses to and is in fluid communication, either directly or through interstitial flow, with the supply artery. Collateral Arteries supply normal tissues.

An "Anatomical Zone" is an area surrounding that portion of the supply artery that is distal to an occlusion. In some embodiments of the present disclosure, the supply artery distal to an occlusion has a pressure substantially lower than normal mean arterial pressure.

A "Normal Gradient" comprises arterial pressures that define normal flow circulation in the human body.

A "Redistribution Gradient" comprises arterial pressures that result from an occlusion in a Supply Artery which causes flow to redistribute and move toward a low pressure, into a target, and away from healthy tissues.

Blood flow follows pressure gradients. Normal (un-occluded) blood pressure in the supply artery is higher than that of the collaterals and the collaterals may have a pressure higher than that of the target.

In general, the normal pressure gradient (Normal Gradient) is as follows: Supply Artery>Collaterals>Target. The supply artery may have a pressure at or near the mean arterial pressure of the heart which is patient dependent, however, typically has a pressure in the range of 60 mmHg to 110 mmHg. According to aspects of the disclosure, the area of the supply artery distal to an occlusion of the supply artery is typically 10% to 60% below the normal mean arterial pressure at that area.

Under normal physiological conditions and due to the aforementioned normal pressure gradient, the supply artery flows into both the collateral arteries and into the target and is associated with interstitial flow in the surrounding Anatomical Zone. Thereby blood flow in a collateral vessel typically travels away from the supply artery and into healthy tissues.

Collaterals are arteries that branch from the supply artery and are connected to capillary beds that have more than one blood supply and inherently have pressure that may be attenuated below the mean arterial pressure of the supply arteries. When a temporary occlusion is introduced in the supply artery according to the present disclosure, a new pressure gradient (Redistribution Gradient) and related flow redistribution results.

A temporary occlusion is created using a balloon catheter or any other occlusive device or a partially occlusive device. In some embodiments, a partial occlusion device is configured to allow a bypass flow volume in the order of 5% to 25%. To ensure a large pressure gradient, in some embodiments the bypass flow volume is between 5% and 10%, inclusive. The occlusion device can be positioned on a catheter, needle, cannula or the like and can be delivered percutaneously, intravenously or surgically.

As a result of the occlusion, the area distal to the occlusion of the supply artery has a lower pressure than the Normal Mean Arterial Pressure of the Anatomical Zone. The occlusion causes the flow in the supply artery to stop, or be substantially reduced, and new pressure gradient is Collaterals>Supply Artery>Target. In this instance, flow redistribution moves blood from the collaterals and into the target through the supply artery (Redistribution Gradient).

Targets that have terminal capillary beds will continue to accept flow from collateral arteries and the Anatomical Zone, whereby inward blood flow exits through the target into veins that have a very low pressure at about 10 mmHg. Targets can have sump like properties that "drain" the inflow of blood that moves toward the low pressure zone. Due to the terminal capillary beds, targets can have a lower pressure than collateral arteries and associated capillaries.

In this instance, mass flow of capillaries, arterioles and arteries of the Anatomical Zone will be directed toward the low pressure zone of the Target. This includes capillaries distal to the occlusion and in the vicinity of the Target. When drug is injected through the catheter, redistributed blood flow will carry the drug exclusively into the Target, and flow of the drug through the collaterals and into healthy tissue will not occur. During the time that the occlusion of the supply artery is in place, the area surrounding the low pressure anatomical zone will flush into the low pressure zone through the capillary beds that are normally fed by both the Supply Artery and other source arteries. To create this reverse flow from the capillary beds, a low pressure anatomical zone is maintained by the temporary occlusion.

In the case of tumor embolization, tumors have terminal capillaries and the aforementioned method will create flow into the tumor. In the case of prostate artery embolization (PAE), the prostate has terminal capillaries and the aforementioned method will create redistributed flow into the prostate. By performing the method on both of the main arteries feeding the prostate, ischemia in the entire prostate can be achieved, shrinking it by at least 10%.

In the case of embolization therapy, such as in tumor embolization, pressure measured in the vessels distal to the occlusion can be used to quantitatively detect embolization endpoint as previously described, since pressure will rise as embolization of the target progresses. An automated injection system can control embolization agent injection pressure to maintain a favorable pressure gradient.

Figure 65:
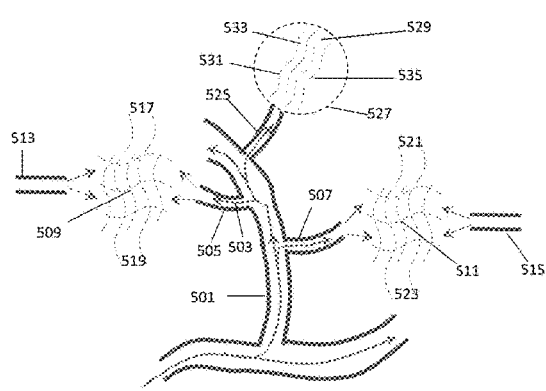
FIG. 65 shows the target tissue and immediately adjacent arteries and capillaries of FIG. 64 after a temporary occlusion is introduced into the target artery.
Figure 66:
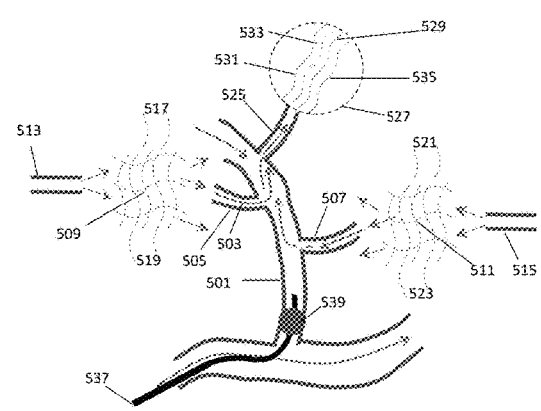
FIG. 66 is a chart showing pressure vs. time for an exemplary low pressure embolization method according to aspects of the present disclosure compared with a standard embolization procedure.

Referring now to FIGS. 65 and 66, a representative arterial system located adjacent to target tissue is shown. FIG. 65 depicts the representative arterial system before occlusion, and FIG. 66 depicts the same arterial system after a temporary occlusion is introduced. Blood flow direction is shown by arrows 503. Before occlusion (FIG. 65), blood flows from supply artery 501 into target artery 525 feeding target tissue 527. Eventually blood makes its way into the terminal capillaries of target 527. The terminal capillaries include the arterial side 531, the venous side 533, and the arterial venous interface 535 therebetween.

In addition to feeding target 527, supply artery 501 feeds a first capillary bed 509 through a first collateral artery 505, and a second capillary bed 511 through a second collateral artery 507. Capillary beds 509 and 511 each contain hundreds of capillaries. Supply artery 501 typically will feed more than two capillary beds but only two are shown for ease of understanding. Reference numerals 517 and 519 depict the position of healthy tissue fed by first capillary bed 509, and reference numerals 521 and 523 depict the position of healthy tissue fed by second capillary bed 511. In addition to being fed by first collateral artery 505, first capillary bed 509 is also fed by a secondary arterial supply 513. Similarly, in addition to being fed by second collateral artery 507, second capillary bed 511 is also fed by a secondary arterial supply 515. Capillary beds 509 and 511 may each be fed by more than two arteries but only two are shown for ease of understanding.

Under a normal pressure gradient, the mean arterial pressure at each point along a blood flow path typically goes down as blood flows from supply artery 501, through collateral artery 505, 507, and target artery 525, through arterial side capillaries 531 and into venous side capillaries 533. This reducing pressure is what causes the blood to continue flowing through the arterial system. In some patients, a typical pressure gradient would include a mean arterial blood pressure of 90 mm Hg in supply artery 501, a pressure of 60 mm Hg in collateral and target arteries 505, 507 and 525, and a pressure of 20 mm Hg in terminal capillaries 529. Typical flow rates could be about 3 to 5 ml/sec in the artery that feeds supply artery 501, 2 to 3 ml/sec in supply artery 501, and 0.5 to 1.0 ml/sec in collateral and target arteries 505, 507 and 525.

As shown in FIG. 66, a balloon catheter 537 may be introduced into the arterial system of FIG. 65, such as through a femoral or radial artery. Once in place, balloon 539 may be inflated to partially or fully occlude a proximal portion of supply artery 501. The target 527 continues to draw blood into it, acting as a sump. According to some aspects of the present disclosure, the mean arterial blood pressure in supply artery 501 drops 10 to 60% below its normal, un-occluded state in the vascular space distal to the occlusion. In some embodiments, the drop in pressure is between 5 and 90% below normal. In some embodiments, the drop in pressure is between 20 and 40% below normal. This drop in pressure causes a redistribution pressure gradient and redistributed blood flow, which includes blood flowing in an opposite direction in some vessels distal to the occlusion. In particular, blood flows in a reverse direction in collateral arteries 505 and 507, and in the distal end of supply artery 501, as shown by flow direction arrows 503. Instead of blood flowing from supply artery 501 to capillary beds 509 and 511, blood instead flows in a reverse direction from capillary beds 509 and 511, through supply artery 501 and into target 527. During this redistributed flow, capillary beds 509 and 511 are not adversely affected since they continue to be fed by at least secondary arterial supplies 513 and 515, respectively. This redistributed flow ensures that embolization agents and/or other drugs emanating from balloon catheter 537 are carried toward target 527 and do not migrate into healthy tissue such as 517, 519, 521 and 523. Partial blood flow past occlusion balloon 539 may be used to carry drugs from a region of supply artery 501 just distal to balloon 539 towards and into target 527.

During the redistributed blood flow described above, and as a result of a lower pressure in the Anatomical Zone, it is believed that there is a general flushing of fluids toward the low pressure zone which protects healthy tissue from non-target drug flow. Initial testing indicates that lower pressure gradients and lower blood flows result in better tumor filling with embolization agents.

Figure 67:
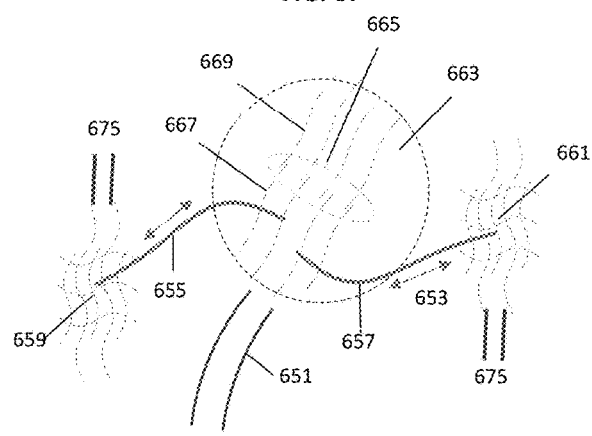
FIG. 67 is an axial cross-section showing an alternative catheter balloon design.
Figure 68:
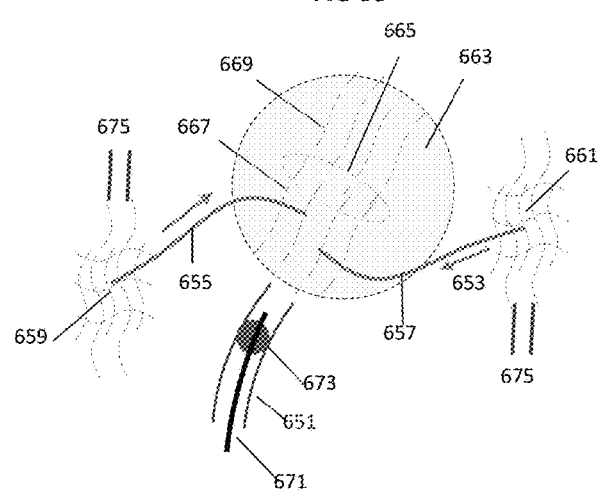
FIG. 68 shows an embodiment of a catheter balloon having spiral channels, shown in a deflated configuration.

Referring now to FIGS. 67 and 68, a modified method will be described that is similar to the method previously described in relation to FIGS. 65 and 66. In FIGS. 67 and 68 the catheter is moved up into target artery 651, which is analogous to target artery 525 shown in FIGS. 65 and 66. FIG. 67 shows the target anatomy un-occluded while FIG. 68 shows an occlusion balloon 673 in place and inflated, causing a redistribution pressure gradient.

In this instance, target 663 can be an organ, tissue, tumor or any other anatomical structure that has a terminal capillary bed (i.e. empties directly into the venous system) such as a prostate, pancreas, liver, kidney or other organ, in whole or in part. The arteries, arterioles and capillaries of the target can have collaterals which feed networks that can be within another organ or tissue and have an arterial supply 675. The target capillary bed 665 (having arterial side 667 and venous side 669) may have similar pressures to the capillary beds 659 and 661 which can be within an organ or tissue. Thereby flow may travel in either direction as seen by arrow 653 of FIG. 67. In FIG. 68, the occlusion balloon 673 of catheter 671 blocks the flow of target artery 651 and causes a pressure drop in the target 663. When the pressure of target 663 drops, collateral arteries 655 and 657 flow only into target 663 as indicated by arrow 653 of FIG. 68. In this manner, drug delivery into an anatomical structure such as target 663 can be enhanced by occluding the artery or arteries that feed the target. The pressure in an anatomical structure can be lowered and blood and fluid flow will be directed exclusively toward the target anatomical structure.

Figure 69:
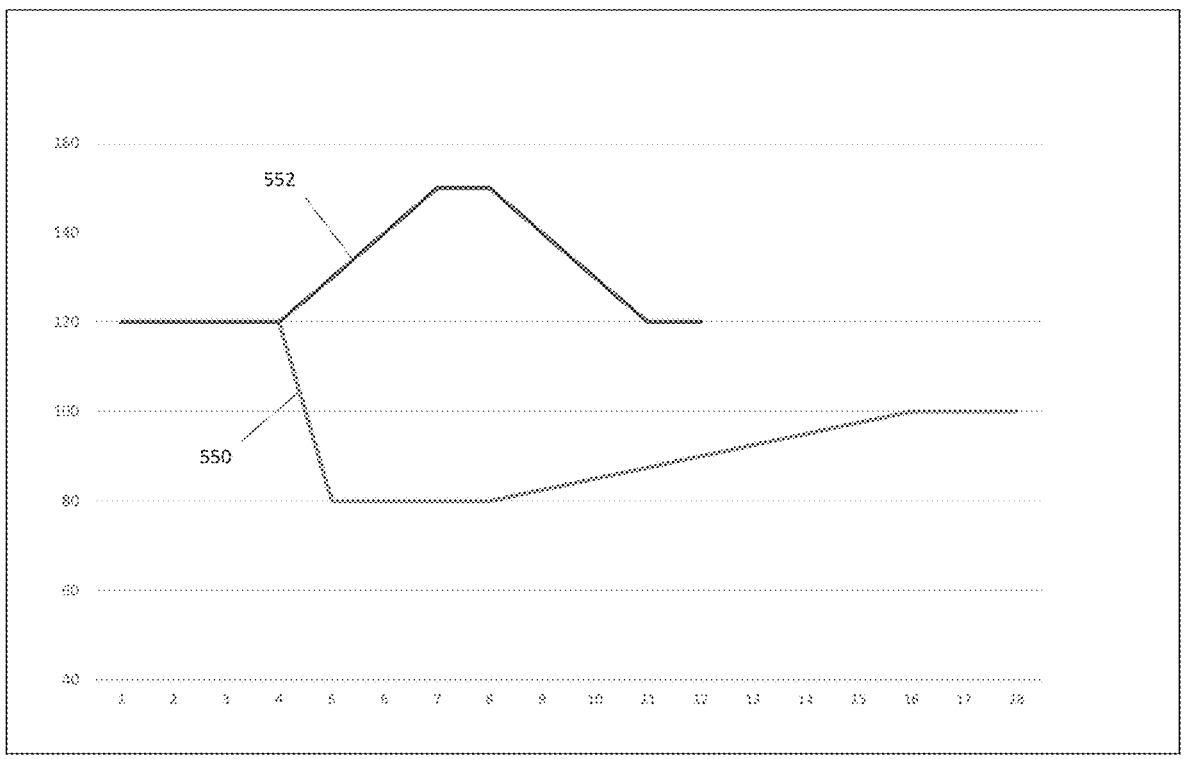
FIG. 69 shows the balloon of FIG. 68 in an inflated configuration.

Referring now to FIG. 69, a chart is provided showing pressure vs. time for an exemplary low pressure embolization method according to aspects of the present disclosure compared with a standard embolization procedure. The low pressure method is depicted by line 550 and the standard method is depicted by line 552. For both methods the horizontal axis represents time (in minutes) elapsed since the pressure measurements started and the vertical axis represents the mean arterial pressure (in mm Hg) in the vascular space distal to the tip of the embolization catheter. At times 1 minute to 4 minutes, the line of the standard method (552) and the low pressure method (550) overlap at the normal mean arterial pressure which is, in this case 120 mmHg. In the standard procedure 552, release of the embolization agent begins around 4 minutes. Because an occlusion device is not used, as the embolization agent is injected and the embolization progresses, the pressure increases above the mean arterial pressure to 150 mmHg at minute 7. Once the injection stops at 7 minutes, the pressure will no longer increase and over a time may return to the mean arterial pressure at minute 11 as the collateral arteries are able to accept the normal blood flow. In contrast to the standard embolization procedure, at minute 4 in the exemplary low pressure procedure 550 an occlusion structure, such as a balloon, is expanded into an occlusion configuration in the supply artery, as previously described. Since blood flow into the supply artery is partially or fully occluded by the structure, the pressure drops (sometimes to zero, or close thereto) and stabilizes at 80 mmHg, which is 40 mmHg below normal mean arterial pressure. The pressure drop is stable until embolization injection starts at minute 8. In this instance the pressure drops from 120 to 80 mm Hg, or about 33%. At minute 8 injection of embolization agent is begun through the balloon catheter into the supply artery. The injection is done at a low pressure and at a slow flow rate to ensure that the redistribution pressure gradient is maintained. In some embodiments, the embolization flow rate is maintained between 0.25 to 6 ml/minute and/or a flow rate that keeps the pressure rising slowly, such as in the example shown in FIG. 69. Between minutes 8 and 16, the tumor is progressively filling with more embolization agent and therefore accepting less blood from the supply artery, thereby allowing the pressure to rise. In this example, the tumor is embolized around minute 16, causing the pressure to level off at 100 mm Hg. The pressure leveling off or reaching a predetermined point may be used to signal the endpoint of the procedure. By using this low pressure and slow flow approach, the tumor can be filled more completely than with the standard procedure, and embolization agent can be kept away from healthy tissue adjacent the tumor. In initial testing, the methods disclosed herein allow a tumor to fill with 2.4 times as many microbeads of embolization agent compared with standard procedures. Initial testing indicates that the mean arterial pressure just distal of the occlusion should be kept below the starting pressure by at least 10 to 30% of the difference between the un-occluded starting pressure and the stabilized occluded pressure to maintain the Redistribution Gradient and optimal tumor filling. In the example of FIG. 69, the starting pressure is 120 mmHg and the stabilized occluded pressure is 80 mmHg, yielding a difference of 40 mmHg. 10 to 30% of this difference is 4 to 12 mmHg, so the pressure during tumor filling should be kept below 116 to 108 mmHg for optimal filling. The lowered pressure may be maintained by limiting the pressure and/or flow rate of the embolization agent. It should be noted that this pressure ceiling range also applies to dispensing other drugs in other procedures targeting certain target tissue and is not limited to dispensing embolization agent.

The following is a summary of an animal study conducted during the development of the methods and devices disclosed herein.

Animal Study Approach

FIGS. 70-72 show the in-vivo tumor flow model developed in Phase 1B of the testing. A capillary is inserted into a hepatic artery that has at least one or several branch hepatoenteric arteries, arterioles, anastomotic vessels and/or capillaries that normally flow away from the hepatic artery. The proximal end of the capillary is open producing a low pressure "pseudo-tumor". When particles are injected as in FIGS. 70-72, the blood and particles can be collected. FIG. 70 also illustrates a normal blood flow pattern in a patient with a tumor as indicated by arrows. Blood will flow away from higher pressure and toward lower pressure. Systolic pressure is higher than that of branch arteries, capillaries, and tumor, thereby blood flows both into the branch arteries toward healthy tissue and into the tumor.

Current Method:

Presently, standard delivery catheters are used for tumor embolization. Typically, the catheter tip is positioned in an artery proximal to both the tumor and one or several branch arteries and capillaries that flow away from the tumor as shown in FIG. 71. When embolic agents are injected, the flow pattern remains normal as in FIGS. 70 and 71 such that particles are distributed between the tumor feeder artery(s) and branch arteries that feed healthy tissues and organs. In addition, the right hepatic artery of FIG. 71 is flowing at about 2-4 ml/sec. The extensive capillary beds of the tumor can normally accept this high rate of flow. However, at the onset of embolization, larger tumor capillaries become blocked, high intra-tumor pressure causes tumor flow to be progressively and sharply reduced; this limiting the extent of embolization (analogous to filling a tea cup with a fire hose). For these reasons, efficacy and reproducibility of present embolization therapy are far from optimal.

Occlusive Method:

According to the method developed in Phase I and illustrated in FIG. 72, an occlusion balloon is expanded in the right hepatic artery to temporarily occlude flow. Immediately following the balloon inflation, the blood pressure distal to the balloon drops significantly and in the order of 10-50 mmHg. When the pressure is reduced distal to the occlusion, branch arteries and capillaries reverse flow, following the pressure gradient as in FIG. 72. Because the tumor has the lowest pressure, all blood flow is directed into the tumor whereby non-target flow into branch arteries no longer can occur. The tumor has extensive terminal capillary beds that exit into low pressure veins, thereby creating a sump-like effect that accepts the flow from the reversed side branches which have a much slower flow rate as compared to the unobstructed right hepatic artery. The net result is that all embolic agents are directed into the tumor at a reduced flow rate, whereby the tumor filling is improved while the surrounding non-cancerous tissue is protected.

Animal Study Protocol (Used for Phase IB and Phase II)

Using contrast injected through a guide catheter placed into the celiac artery and with fluoroscopic imaging, select locations for placement of the Inventive Occlusion Balloon Catheter and the AccuStick (Boston Scientific) Catheter as in FIG. 70.

Under fluoroscopic guidance, advance the Inventive Occlusion Balloon Catheter within hepatic artery to a position that is 2 to 6 cm proximal to the location selected for the AccuStick, making sure that there are branch arteries between the distal tip of the Inventive Catheter and the AccuStick.

Perform a laparotomy and use visual examination (with ultrasound assist), of the liver and associated arteries and identify the tip of the Inventive Catheter in the hepatic artery and the distal artery selected for insertion of the AccuStick.

Make a small incision in the arterial wall and insert the AccuStick into the artery. Secure with suture.

Connect the proximal end of the AccuStick to ⅛" tubing, including an adjustable stopcock, and extend the tubing to a blood collection vessel as in FIGS. 70-72.

Using a Pendotech in-line pressure transducer connected to the proximal injection lumen of the Inventive Occlusion Balloon Catheter (FIG. 76) measure blood pressure through the catheter with the balloon in the unexpanded configuration (P0, Standard Pressure).

Inflate the occlusion balloon and measure the pressure (P1) at the tip of the catheter, noting flow of branch arteries via contrast injection.

While measuring blood pressure, begin to open stopcock of AccuStick (or 19 gauge needle) until the pressure reading at the tip of the catheter is 10-30 mmHg lower than Standard Pressure while collecting blood in a flask as seen in FIGS. 70-72, noting flow of branch arteries via contrast injection. Measure blood pressure (P2).

Inject microparticles through the Inventive Occlusion Balloon Catheter while collecting blood.

Following the completion of microparticle injection, allow the blood to flow for an additional several minutes, and then close the stopcock.

Measure blood pressure (P3).

Repeat the microparticle injection 2 more times with the balloon in its expanded configuration, collecting blood in a new vessel for each replicate.

Repeat the microparticle injection 3 times with the balloon in its unexpanded configuration, collecting the blood in a new centrifuge tube each time.

Repeat steps 1 through 10 on a second pig.

Isolate the microparticles using filtration and suspend in 250 µL of saline. Determine yield by weight (Phase 1B) or particle count.

Compare results from inflated balloon and uninflated balloon. Improved particle recovery from the balloon up condition as compared to the balloon down condition is considered to be a validation of the theory.

Discussion

As in the Phase IB Project Description, 2 animals will be used to test the in-vivo tumor model design that is illustrated in FIGS. 70-72.

The Phase 1B pig study has been completed and the results shown in FIG's A, B and C (not adequately reproducible for patent application) which are contrast enhanced fluorographic images taken during the animal procedure.

Figure A (not in patent application) shows an angiogram of the vascular structure in the pig's liver showing artery 2 which is the right hepatic artery, artery 1, a branch off the right hepatic and arteries 3-5 which are other hepatic and hepatoenteric arteries. The marker bands of the Inventive Catheter are seen in the common hepatic artery. In this figure the, contrast was injected through the guide catheter with its [balloon] positioned proximal to the Inventive Catheter tip. The tip of the guide catheter is positioned in the celiac artery as it exits the aorta. This positioning is the reason that the entire vascular tree is visualized. Since the guide catheter used in this study had a 5 Fr inner diameter, contrast was injected at a high flow and the vascular tree is relatively dark.

Also noted in FIG B (not shown) is the placement site of the "pseudo-tumor" catheter in distal artery 3. The blood from the catheter placed in artery 3 was collected in a test tube as shown.

FIG B (not shown) is a fluorographic image of the Inventive Device placed in the common hepatic artery as evidenced by the marker bands. In this instance, the Inventive Balloon was down which is equivalent to a standard catheter that is currently used for tumor embolization. This time, contrast was injected through the Inventive Catheter and the angiogram (lighter because the slower contrast flow rate through a microcatheter) shows the same arterial tree as in FIG A (not shown) with arteries 1, 2, 3, 5 & 6 visible. Artery 4 could not be seen because the contrast concentration was insufficient to visualize this artery. FIG. C (not shown) illustrates what happens when the balloon is inflated. In this case only the tumor feeder artery 3 is visible. When contrast was injected using a power injector at about 3 ml/sec, contrast was forced up branch arteries 1, 2, 4 & 5, however once the contrast injection stopped, contrast in the branch arteries flushed back into the tumor feeder artery 3, this demonstrating flow reversal of these non-tumor arteries.

Particle Injection: Embolic particles (100-300µ, Merit Medical) were injected under the conditions seen in both FIG B (not shown—standard condition) and FIG C (not shown—inventive condition).

According to the method as stated above, blood pressure would drop immediately following balloon occlusion and stabilize in the vascular compartment distal to the occlusion. In fact, it is this pressure reduction that causes flow reversal of branch arteries and blood flow directed exclusively into the tumor. Pressure was measured through the catheter using an in-line pressure transducer located at the proximal end of the catheter. According to the Phase 1 theory, the pressure in the vascular compartment distal to the balloon occlusion would immediately drop to a pressure lower than systolic, but not to zero. The pressure is non-zero because of the flow reversal of branch arteries and capillaries which are part of arterial networks. These networks inherently have a pressure due to the multiple sources that are feeding the network. In this instance, the blood pressure in the networks is attenuated given the multitude of vessels in the network. As a point of interest, when the Inventive Catheter Balloon is up, the blood pressure that is measured is that of the arterial networks and inward flow of other vessels. In one experiment, the initial blood pressure is about 67 mmHg which rapidly drops when the balloon is inflated to below 35 mmHg, then stabilizes at about 48 mmHg, a pressure drop of 19 mmHg. During particle injection, the pressure reading is not attainable using this in-line sensor. Following injection, the pressure returns to about systolic. This data again meets the Phase 1 expectations.

The occlusion microcatheter of Phase 1 has been successfully developed and tested and is, at this point, clinically capable. In addition, it appears that the new animal study design is feasible and has already provided quantitative results that are consistent with the Phase 1 theory.

Phase IB Animal Study (for Set Up)

This study was used to test and optimize the proposed protocol prior to use in the final Phase I animal study. This study included 2 pigs and followed the protocol outlined above. For each animal there are 3 balloon up replicates and 3 balloon down replicates or 6 data points per animal. Following collection of the beads, the following table shows the data points from each animal averaged in the balloon up and balloon down cases:

| Animal # | Balloon Down | Balloon Up | Delta (g) | Fold increase in bead capture |
|---|---|---|---|---|
| 1 | 0.45 g | 0.92 g | 0.47 g | 2.04 |
| 2 | 0.15 g | 0.22 g | 0.07 g | 1.46 |

Discussion: The animal study of Phase IB showed a significant increase in particles collected when the balloon was up. This is consistent with the expected results and the theory set forth in the present project. However, as in FIGS. B and C (not shown), the difference between the balloon up and balloon down conditions appears to be visually greater than 2× and it was noted that weight differences are difficult to measure accurately since the cell strainer has a mass many times that of the beads. The total mass of beads that were injected was 1.0 g. It is noted that the total recovery in animal #1 is reasonable while that of animal #2 is low. It is believed that the tumor catheter leaked at the entry to the tumor artery due to an incomplete seal.

Conclusions: The animal protocol as in the Phase IB is shown to be quantitative and far better than that initially described. As such this new protocol will be used for the final Phase 1 study. The following improvements will be made:

Use particle count as a means to measure each condition rather than mass

Suture the tumor catheter in place and make sure there are no leaks throughout the study Phase 1 Animal Study (Aim #3 of the Phase I Project Description)
The Animal Study Protocol of Phase IB, will be used.
Materials and Methods
  Animals used: American Yorkshire Pigs, 75 Kg+15 Kg
  Microbeads: CeloNova Embozene® Microsphere
  400 µm—blue; REF 14020-S1
  250 µm—yellow; REF 12020-S1
  2 ml syringe reconstituted to 8 ml total with 100% contrast
  Excess fluid removed after beads settle in syringe
  Contrast (100%) added to help maintain bead constitution in fluid
  2 ml beads+6 ml contrast=8 ml total volume
  Split to (2) 1 ml samples of 4 ml each
  Injected via stopcock using 1 ml injection syringe
Study Algorithm
  24 data sets (12 pairs) Analyzed
  First Test Date:
  Pig 1: data rejected, abnormal vascular anatomy
  Pig 2: 8 data sets (4 pairs) 3 pair analyzed
  250 µm & 400 µm balloon up & down (×2)
    2nd 250 µm data set not analyzed—clot blocked blood flow proximal to catheter
  Pig 3: 6 data sets (3 pair) 3 pair analyzed
  250 µm balloon up & down (×2)
  400 µm balloon up & down (×2)
  Second Test Date:
  Pig 1: 6 data sets (3 pair) 1 pair analyzed
    250 µm balloon up & down (×2)
      1st 250 µm data set not analyzed—placement too close to tumor model; no branch arteries between catheters
    400 µm balloon up & down (×1)
      Note: 400 µm would not reconstitute after collection—data not analyzed
  Pig 2: 6 data sets (3 pair) 3 pair analyzed
    250 µm balloon up & down (×2)
    400 µm balloon up & down (×1)
  Pig 3: 4 data sets (2 pair) 2 pair analyzed
    Anatomy limited testing to 1 catheter location
    250 µm balloon up & down (×1)
    400 µm balloon up & down (×1)
Bead Count Methodology
  Beads Collected in Cell Filter
  Falcon, 70 µm filter
  Cleaned with water
  Beads mixed with 25 ml water
  Magnetic Mixer Homogenizes Beads
  250 µm analysis:
  100 µl pipette placed on slide
  400 µm analysis:
  250 µl pipette placed on slide
  3 samples taken for each collection
  Min/Mid/Max
  Counted under microscope
  Extrapolate to full 25 ml mix
  Ex: bead count/pipette volume*25 ml solution=beads collected
Discussion
The in-vivo model described herein is intended to emulate anatomical structure and flow dynamic properties associated with a tumor in the human liver. The low pressure pseudo-tumor described herein is characteristic of a tumor which functionally behaves like a sump since the vast capillary bed within a tumor empties directly into veins that have near zero pressure. Examination of contrast flow with the balloon down (straight tip catheter) and the balloon up (occlusive condition) demonstrate flow redistribution in favor of the pseudo-tumor when the balloon is occlusive. It is therefore not surprising that injection with the balloon up always resulted in a much higher (average 2.4 times) amount of beads collected. Furthermore, it is evident that when the balloon is down, fewer beads are collected and the balance of the beads are randomly distributed among the branch arteries and healthy tissues. The bead collection results of this study are summarized in the table of FIG. 73.

It is noted that Bead recovery may be impacted by multiple sequential bead injections in the same animal due to embolization of branch arteries. We believe that this favors the balloon down condition since non-target flow into occluded arteries cannot occur. In order to minimize this effect, the first injection was done at a location closest to the low pressure zone and the second injection furthest from the low pressure zone. It is likewise noted that the pseudo-tumor is never embolized and remains as a "sump". This too will impact the relative bead collection between the balloon up and balloon down conditions. Further study is needed to elucidate a broader understanding of embolization at a low pressure.

Conclusions of Animal Study
The in-vivo flow simulation of a liver tumor shows that balloon occlusion consistently results in a sizable increase in the quantity of embolic particles delivered to a "pseudo tumor". The explanation for this phenomenon is clearly a function of pressure gradients that result from blockage of the high pressure supply artery and redistribution of blood flow in favor of the tumor. Normal unoccluded flow is driven by the supply hepatic artery that has the highest pressure and flow rate. Thereby the normal flow is characterized by the following pressure gradient: hepatic artery pressure is greater than branch arterial network pressure which is greater than tumor pressure. In contrast, when the hepatic artery flow is stopped, the AP between the branch arterial networks and the tumor creates a flow from the capillary networks into the tumor. It follows that balloon occlusion produces a favorable flow pattern that directs injected agents exclusively into the tumor and an absence of embolic agent flow toward healthy tissues. It is also speculated that occlusion of the high flow supply artery and subsequent redirection of branch arteries results in a substantial reduction in the rate of flow into the tumor, this allowing an improvement in tumor filling. We conclude that the mechanism behind the observed improvement in tumor filling is directly related to a low distal pressure that results from balloon occlusion. Low Pressure Embolization will enable a new era of tumor embolization with improvements in both safety and efficacy. The method should also make tumor embolization to be less technique dependent and provide improved center to center reproducibility.

It is important to note that in some embodiments of the present disclosure the devices regulate flow and pressure in the arterial space distal to the partial occlusion balloon, significantly reducing flow rate and pressure in tumor capillaries and cause flow reversal of distal branch arteries. These devices and methods thereby enable substantial elimination of retrograde and antegrade flow to non-target sites and a more complete filling of the tumor vasculature with drug and or embolic agents and should improve efficacy and reduce complications over standard devices and methods.

What is claimed is:
1. A method of transarterial embolization agent delivery at a low pressure, the method comprising:

advancing a delivery device with an occlusion structure in a retracted non-occlusive configuration, through a supply artery having a plurality of collateral vessels that branch therefrom and being in fluid communication with a target anatomical structure, to a vascular position in the supply artery that is in the vicinity of the target anatomical structure, the target structure having terminal capillary beds;

expanding the occlusion structure from the retracted non-occlusive configuration to an expanded occlusive configuration;

lowering a mean arterial pressure in a vascular space distal to the expanded occlusion structure;

redirecting fluid flow from the collateral vessels toward the lowered pressure vascular space and into the target anatomical structure such that a fluid flow direction is reversed in at least some of the collateral vessels;

injecting an embolization agent through the delivery device and into the lowered pressure vascular space; and delivering the embolization agent from the lowered pressure vascular space into the target anatomical structure.

2. A method according to claim 1, wherein the mean arterial pressure in the lowered pressure vascular space is lowered during the lowering step to between 10% and 60% of a normal mean arterial pressure.

3. A method according to claim 1, wherein the lowering step comprises measuring a pressure in the vascular space after expanding the occlusion structure.

4. A method according to claim 3, wherein the lowering step further comprises ensuring the measured pressure is within a predetermined range before proceeding with the injecting step.

5. A method according to claim 1, wherein the lowering step comprises waiting a predetermined period of time before proceeding with the injecting step to ensure that a sufficient pressure drop has occurred.

6. A method according to claim 1, wherein the fluid is predominantly blood.

7. A method according to claim 1, wherein the fluid is predominantly interstitial fluid.

8. A method according to claim 1, wherein the embolization agent is injected with a flow rate in the range of 0.25 to 10 ml/minute.

9. A method according to claim 1, wherein the delivery device comprises a catheter.

10. A method according to claim 1, wherein the delivery device comprises a needle.

11. A method according to claim 1, wherein the delivery device comprises a cannula.

12. A method according to claim 1, wherein the occlusion structure allows a fluid flow of 5 to 25% of normal to bypass the occlusion structure after it has been expanded into the occlusive configuration.

13. A method according to claim 1, wherein the occlusion structure creates a substantially full occlusion having less than 2% bypass blood flow.

14. A method according to claim 1, wherein the occlusion structure comprises a balloon.

15. A method according to claim 14, wherein the balloon is provided with a generally v-shaped channel extending along a least a portion of its length, thereby providing a fluid bypass channel when the balloon is inflated.

16. A method according to claim 14, wherein the balloon is provided with a spiral channel extending from a proximal end of the balloon to a distal end, thereby providing a fluid bypass channel when the balloon is inflated.

17. A method according to claim 1, wherein the delivery device is provided with a pressure transducer located distal to the occlusion structure and configured to sense fluid pressure when located in the supply artery.

18. A method according to claim 1, wherein the target anatomical structure is a tumor.

19. A method according to claim 1, wherein the target anatomical structure is a prostate.

20. A method according to claim 1, wherein the target anatomical structure is a uterus.

21. The method of claim 1, further comprising maintaining antegrade flow in at least one vessel in the lowered pressure vascular space.

* * * * *